US011807851B1

(12) United States Patent
Lee et al.

(10) Patent No.: US 11,807,851 B1
(45) Date of Patent: Nov. 7, 2023

(54) MODIFIED POLYNUCLEOTIDES AND USES THEREOF

(71) Applicant: Ultima Genomics, Inc., Newark, CA (US)

(72) Inventors: Linda G. Lee, Palo Alto, CA (US); Steven Menchen, Fremont, CA (US)

(73) Assignee: Ultima Genomics, Inc., Newark, CA (US)

( * ) Notice: Subject to any disclaimer, the term of this patent is extended or adjusted under 35 U.S.C. 154(b) by 244 days.

(21) Appl. No.: 17/176,617

(22) Filed: Feb. 16, 2021

Related U.S. Application Data

(60) Provisional application No. 62/978,072, filed on Feb. 18, 2020.

(51) Int. Cl.
| | |
|---|---|
| *A61K 31/7072* | (2006.01) |
| *A61K 31/706* | (2006.01) |
| *C12N 15/113* | (2010.01) |
| *C07H 21/04* | (2006.01) |
| *A61K 47/65* | (2017.01) |
| *A61K 49/00* | (2006.01) |
| *C07H 19/14* | (2006.01) |
| *C12Q 1/6874* | (2018.01) |
| *C07K 5/02* | (2006.01) |
| *C07H 19/00* | (2006.01) |

(52) U.S. Cl.
CPC ............ *C12N 15/113* (2013.01); *A61K 47/65* (2017.08); *A61K 49/0021* (2013.01); *C07H 19/14* (2013.01); *C07H 21/04* (2013.01); *C07K 5/0205* (2013.01); *C12Q 1/6874* (2013.01); *C07H 19/00* (2013.01)

(58) Field of Classification Search
None
See application file for complete search history.

(56) References Cited

U.S. PATENT DOCUMENTS

| | | | |
|---|---|---|---|
| 4,772,691 | A | 9/1988 | Herman |
| 5,409,811 | A | 4/1995 | Tabor et al. |
| 5,641,658 | A | 6/1997 | Adams et al. |
| 5,652,099 | A | 7/1997 | Conrad |
| 5,674,716 | A | 10/1997 | Tabor et al. |
| 5,763,167 | A | 6/1998 | Conrad |
| 5,846,514 | A | 12/1998 | Foster et al. |
| 6,136,543 | A | 10/2000 | Anazawa et al. |
| 6,334,997 | B1 | 1/2002 | Foster et al. |
| 6,440,707 | B1 | 8/2002 | Kwok et al. |
| 6,664,079 | B2 | 12/2003 | Ju et al. |
| 6,982,146 | B1 | 1/2006 | Schneider et al. |
| 7,033,762 | B2 | 4/2006 | Nelson et al. |
| 7,041,812 | B2 | 5/2006 | Kumar et al. |
| 7,057,026 | B2 | 6/2006 | Barnes et al. |
| 7,244,566 | B2 | 7/2007 | Sood et al. |
| 7,297,518 | B2 | 11/2007 | Quake et al. |
| 7,405,281 | B2 | 7/2008 | Xu et al. |
| 7,452,698 | B2 | 11/2008 | Sood et al. |
| 7,485,424 | B2 | 2/2009 | Korlach et al. |
| 7,625,701 | B2 | 12/2009 | Williams et al. |
| 7,777,013 | B2 | 8/2010 | Xu et al. |
| 7,883,869 | B2 | 2/2011 | Ju et al. |
| 7,968,702 | B2 | 6/2011 | Wegener et al. |
| 7,973,146 | B2 | 7/2011 | Shen et al. |
| 7,994,304 | B2 | 8/2011 | Siddiqi et al. |
| 8,114,973 | B2 | 2/2012 | Siddiqi et al. |
| 8,133,702 | B2 | 3/2012 | Shen et al. |
| 8,148,516 | B2 | 4/2012 | Williams et al. |
| 8,158,444 | B2 | 4/2012 | Gaylord et al. |
| 8,192,961 | B2 | 6/2012 | Williams |
| 8,252,911 | B2 | 8/2012 | Bjornson et al. |
| 8,304,259 | B2 | 11/2012 | Isobe |
| 8,354,252 | B2 | 1/2013 | Wegener et al. |
| 8,399,188 | B2 | 3/2013 | Zhao et al. |
| 8,772,473 | B2 | 7/2014 | Huang et al. |
| 9,127,314 | B2 | 9/2015 | Liu et al. |
| 9,175,342 | B2 | 11/2015 | Ju et al. |
| 9,279,149 | B2 | 3/2016 | Efcavitch et al. |
| 9,670,539 | B2 | 6/2017 | Ju et al. |
| 9,708,358 | B2 | 7/2017 | Ju et al. |
| 9,777,320 | B2 | 10/2017 | Yue et al. |
| 10,240,195 | B2 | 3/2019 | Fuller et al. |
| 10,246,479 | B2 | 4/2019 | Ju et al. |
| 10,443,096 | B2 | 10/2019 | Ju et al. |
| 10,738,072 | B1 | 8/2020 | Graham et al. |
| 11,377,680 | B2 | 7/2022 | Lee et al. |
| 2006/0057565 | A1 | 3/2006 | Ju et al. |

(Continued)

FOREIGN PATENT DOCUMENTS

| | | |
|---|---|---|
| AU | 718610 B2 | 4/2000 |
| EP | 1291354 A2 | 3/2003 |

(Continued)

OTHER PUBLICATIONS

PCT/US2021/046344 International Search Report and Written Opinion dated Dec. 6, 2021.
U.S. Appl. No. 17/395,382 Notice of Allowance dated Feb. 24, 2022.
U.S. Appl. No. 17/395,382 Office Action dated Nov. 2, 2021.
Adessi et al. Solid phase DNA amplification: Charcterisation of primer attachment and amplification mechanisms, Nucl. Acids Res, 2000, 28(20):E87.
Brenner, et al. Gene expression analysis by massively parallel signature sequencing (MPSS) on microbead arrays. Nat Biotechnol. Jun. 2000;18(6):630-4.

(Continued)

*Primary Examiner* — Traviss C McIntosh, III
(74) *Attorney, Agent, or Firm* — Wilson Sonsini Goodrich & Rosati

(57) ABSTRACT

The present disclosure provides modified substrates such as modified polynucleotides, proteins, antibodies, lipids, and cells and uses thereof. Method of generating the modified substrates, which may comprise cleavage of a cleavable group linking the substrate to a labeling moiety, are also provided herein.

20 Claims, 30 Drawing Sheets

(56) References Cited

U.S. PATENT DOCUMENTS

| | | |
|---|---|---|
| 2007/0275387 A1 | 11/2007 | Ju |
| 2008/0132692 A1 | 6/2008 | Wu et al. |
| 2009/0170724 A1 | 7/2009 | Balasubramanian et al. |
| 2009/0207346 A1 | 8/2009 | Ohuchi et al. |
| 2009/0233302 A1 | 9/2009 | Wegener et al. |
| 2009/0246762 A1 | 10/2009 | Rosenblum et al. |
| 2009/0263791 A1 | 10/2009 | Ju et al. |
| 2009/0269759 A1 | 10/2009 | Menchen, Jr. et al. |
| 2010/0063743 A1 | 3/2010 | Gordon et al. |
| 2010/0330569 A1 | 12/2010 | Olejnik |
| 2011/0195408 A1 | 8/2011 | Isobe |
| 2011/0311964 A1 | 12/2011 | Wegener et al. |
| 2012/0064531 A1 | 3/2012 | Ahn |
| 2012/0156680 A1 | 6/2012 | Ju et al. |
| 2013/0053252 A1 | 2/2013 | Xie et al. |
| 2013/0078640 A1 | 3/2013 | Rabbani et al. |
| 2013/0264207 A1 | 10/2013 | Ju et al. |
| 2014/0162892 A1 | 6/2014 | Mir |
| 2015/0094457 A1 | 4/2015 | Miao et al. |
| 2016/0347907 A1 | 12/2016 | Dose |
| 2017/0029883 A1 | 2/2017 | Zhao et al. |
| 2017/0067104 A1* | 3/2017 | Balasubramanian ............ C12Q 1/6834 |
| 2020/0055896 A1 | 2/2020 | Bainbridge et al. |
| 2022/0282309 A1 | 9/2022 | Lee et al. |

FOREIGN PATENT DOCUMENTS

| | | |
|---|---|---|
| EP | 2436778 A2 | 4/2012 |
| EP | 2226330 B1 | 9/2013 |
| EP | 1497304 B1 | 6/2014 |
| EP | 2263087 B1 | 8/2017 |
| JP | 3435416 B2 | 8/2003 |
| JP | 4741170 B2 | 8/2011 |
| KR | 0156042 B1 | 10/1998 |
| WO | WO-9106678 A1 | 5/1991 |
| WO | WO-0053805 A1 | 9/2000 |
| WO | WO-0053812 A2 | 9/2000 |
| WO | WO-2007013601 A1 | 2/2007 |
| WO | WO-2009002993 A1 | 12/2008 |
| WO | WO-2010007114 A2 | 1/2010 |
| WO | WO-2017058953 A1 | 4/2017 |
| WO | WO-2017087823 A1 | 5/2017 |
| WO | WO-2018064311 A2 | 4/2018 |
| WO | WO-2019105421 A1 | 6/2019 |
| WO | WO-2020172197 A1 | 8/2020 |
| WO | WO-2022040213 A1 | 2/2022 |
| WO | WO-2022212408 A1 | 10/2022 |
| WO | WO-2023164003 A2 | 8/2023 |

OTHER PUBLICATIONS

Brenner, et al. In vitro cloning of complex mixtures of DNA on microbeads: physical separation of differentially expressed cDNAs. Proc Natl Acad Sci U S A. Feb. 15, 2000;97(4):1665-70.

Cahova, et al. 5-Substituted Pyrimidine and 7-Substituted 7-Deazapurine dNTPs as Substrates for DNA Polymerases in Competitive Primer Extension in the Presence of Natural dNTPs. ACS Chem Biol. Nov. 18, 2016;11(11):3165-3171. Epub Oct. 6, 2016.

Co-pending U.S. Application No. 202117395382, inventor Lee; Linda, filed on Aug. 5, 2021.

Dernburg, A.F. Fragmentation and labeling of probe DNA for whole-mount Fish in *Drosophila*. Cold Spring Harb Protoc. Dec. 1, 2011;2011(12):1527-30. doi: 10.1101/pdb.prot066886.

Dressman, et al. Transforming single DNA molecules into fluorescent magnetic particles for detection and enumeration of genetic variations. Proc Natl Acad Sci USA. 2003;100(15):8817-8822.

Dumousseau, et al. Melting, a flexible platform to predict the melting temperatures of nucleic acids. BMC Bioinformatics 13, 101 (2012). https://doi.org/10.1186/1471-2105-13-101.

Finn, et al. Efficient incorporation of positively charged 2', 3'-dideoxynucleoside-5'-triphosphates by DNA polymerases and their application in 'direct-load' DNA sequencing. Nucleic Acids Res. Aug. 15, 2003;31(16):4769-78.

Fuller et al. "Real-time single-molecule electronic DNA sequencing by synthesis using polymer-tagged nucleotides on a nanopore array" PNAS, Mar. 18, 2016 (Mar. 18, 2016); 113(19):5233-5238 (doi: 10.1073/pnas.1601782113) p. 5234, col. 1, para 1-3; p. 5235, col. 1, para 1; p. 5236, col. 1, para 1; Fig. 2.

Gothard, et al. Nanometer-Sized Amino Acids for the Synthesis of Nanometer-Scale Water-Soluble Molecular Rods of Precise Length. J Am Chem Soc. 2007;129(23):7272-7273. doi:10.1021/ja072648i.

Kumar, et al. Terminal phosphate labeled nucleotides: synthesis, applications, and linker effect on incorporation by DNA polymerases. Nucleosides Nucleotides Nucleic Acids. 2005;24(5-7):401-8.

Lizardi, et al. Mutation detection and single-molecule counting using isothermal rolling-circle amplification. Nat Genet. Jul. 1998;19(3):225-32.

Mitra, et al. Digital genotyping and haplotyping with polymerase colonies. Proc Natl Acad Sci USA. 2003.100(10):15926-5931.

Mitra et al. Fluorescent in situ sequencing on polymerase colonies, Anal. Biochem, 320:55-65. (2003).

PCT International Search Report and Written Opinion, PCT Application No. PCT/US20/20018699, dated May 11, 2020, 15 pages.

Pemov et al. DNA analysis with multiplex microarray-enhanced PCR, Nucl. Acids Res, 2005, 33(2):e11, pp. 1-9.

Reinartz, et al. Massively parallel signature sequencing (MPSS) as a tool for in-depth quantitative gene expression profiling in all organisms. Brief Funct Genomic Proteomic. Feb. 2002;1(1):95-104.

Schuler, et al. Polyproline and the "spectroscopic ruler" revisited with single-molecule fluorescence. Proc Natl Acad Sci U S A. 2005;102(8):2754-2759. doi:10.1073/pnas.0408164102.

Stryer, et al. Energy transfer: a spectroscopic ruler. Proc Natl Acad Sci U S A. Aug. 1967;58(2): 719-726. doi: 10.1073/pnas.58.2.719.

Tabor et al., A single residue in DNA polymerases of the *Escherichia coli* DNA polymerase I family is critical for distinguishing between deoxy- and dideoxyribonucleotides; PNAS, vol. 92, No. 14, pp. 6339-6343 (1995).

Tabor, et al., Effect of manganese ions on the incorporation of dideoxynucleotides by bacteriophage T7 DNA polymerase and *Escherichia coli* DNA polymerase I, Proc. Natl. Acad. Sci. USA, Jun. 1989, 86:4076-80.

Yu Jiang, et al. Cleavable Linkers in DNA Sequencing by Synthesis. Progress in Chemistry, 2016, 28(1): 58-66 (English abstract only).

Bowers, et al. Virtual Terminator nucleotides for next generation DNA sequencing, Nat Methods 6,8 (2009): 593-95.

He, et al. A traceless linker for aliphatic amines that rapidly and quantitatively fragments after reduction. Chemical Science 11.33 (2020): 8973-8980.

Knapp, Diana C. et al. Fluorescent labeling of (oligo) nucleotides by a new fluoride cleavable linker capable of versatile attachment modes. Bioconjugate chemistry vol. 21,6 (2010): 1043-55.

PCT/US22/22393 International Search Report and Written Opinion dated Aug. 19, 2022.

Thermo Fisher Scientific. Introduction to Thiol Modification and Detection—Section 2.1. Available at https://www.thermofisher.com/us/en/home/references/molecular-probes-the-handbook/thiol-reactive-probes/introduction-to-thiol-modification-and-detection. Accessed on Nov. 25, 2020.

Zalipsky, S et al. New detachable poly(ethylene glycol) conjugates: cysteine-cleavable lipopolymers regenerating natural phospholipid, diacyl phosphatidylethanolamine. Bioconjugate chemistry vol. 10,5 (1999): 703-7.

Chattopadhyay, et al. Brilliant violet fluorophores: a new class of ultrabright fluorescent compounds for immunofluorescence experiments. Cytometry Part A 81.6 (2012): 456-466.

Chen, et al. Mechanisms of quenching of Alexa fluorophores by natural amino acids.Journal of the American Chemical Society 132.21 (2010): 7244-7245.

Drmanac, et al. CoolMPS™: Advanced massively parallel sequencing using antibodies specific to each natural nucleobase.bioRxiv (2020).

Heinlein, et al. Photoinduced electron transfer between fluorescent dyes and guanosine residues in DNA-hairpins.The Journal of Physical Chemistry B 107.31 (2003): 7957-7964.

Co-pending U.S. Appl. No. 18/111,220, inventors Lee; Linda G. et al., filed Feb. 17, 2023.

(56) References Cited

OTHER PUBLICATIONS

EP20760212.9 Extended European Search Report dated Oct. 31, 2022.
Chen, X., et al. Fluorescence Polarization in Homogeneous Nucleic Acid Analysis. Genome 14 Research, vol. 9, No. 5, May 1999: pp. 492-498.
Finn, PJ., et al. Synthesis and Application of Charge-modified Dye-labeled Dideoxynucleoside-5'-triphosphates to 'direct-load' DNA Sequencing. Nucleic Acids Research. Vol. 30, No. 13, Jul. 1, 2002: pp. 2877-2885.
PCT/US2023/013634 International Search Report and Written Opinion dated Jul. 25, 2023.
Temimi, A.H.K.A., et al. Substrate Scope for Trimethyllysine Hydroxylase Catalysis. Chemical 85 Communications, (Camb), vol. 52, No. 87, Oct. 25, 2016: pp. 12849-12852.

\* cited by examiner

MODIFIED POLYNUCLEOTIDES AND USES THEREOF

CROSS REFERENCE

This application claims the benefit of U.S. Provisional Patent Application No. 62/978,072, filed Feb. 18, 2020, of which the application is entirely incorporated herein by reference.

BACKGROUND

The detection, quantification and sequencing of cells and biological molecules may be important for molecular biology and medical applications, such as diagnostics. Genetic testing may be useful for a number of diagnostic methods. For example, disorders that are caused by rare genetic alterations (e.g., sequence variants) or changes in epigenetic markers, such as cancer and partial or complete aneuploidy, may be detected or more accurately characterized with deoxyribonucleic acid (DNA) or ribonucleic acid (RNA) sequence information.

Nucleic acid sequencing is a process that can be used to provide sequence information for a nucleic acid sample. Such sequence information may be helpful in diagnosing and/or treating a subject with a condition. For example, the nucleic acid sequence of a subject may be used to identify, diagnose and potentially develop treatments for genetic diseases. As another example, research into pathogens may lead to treatment of contagious diseases.

Nucleic acid sequencing may comprise the use of labeled moieties, such as moieties may be labeled with fluorescent dyes. The sensitivity of a detection scheme can be improved by using dyes with both a high extinction coefficient and quantum yield, where the product of these characteristics may be termed the dye's "brightness." Dye brightness may be attenuated by quenching phenomena, including quenching by biological materials, quenching by proximity to other dyes, and quenching by solvent. Other routes to brightness loss include photobleaching, reactivity to molecular oxygen, and chemical decomposition.

Labeled moieties incorporated into polynucleotides during a sequencing application may impact the incorporation of additional nucleotides, including additional labeled nucleotides. Accordingly, labels may be removed during or after such an application to facilitate additional processing.

SUMMARY

The present disclosure provides compounds and compositions comprising chemical moieties comprising an alkynyl moiety and an amido moiety, as well as methods of preparing the same. The chemical moieties provided herein may be coupled to substrates such as nucleotides, nucleotide analogs, cells, proteins, antibodies, and lipids. The chemical moieties may comprise a ring structure such as an aromatic ring system. The chemical moieties (e.g., "scar" moieties) provided herein may be generated upon cleavage of a cleavable group (e.g., a disulfide moiety), such as upon contacting a substrate comprising such a chemical moiety with a cleavage reagent. For example, a chemical moiety coupled to a substrate (e.g., nucleotide or nucleotide analog) of the present disclosure may be generated subsequent to incorporation of the substrate into, e.g., a polynucleotide, such as during a sequencing process. The substrate may be coupled to a fluorescent labeling reagent (e.g., as described herein) at the time of its incorporation into the polynucleotide. The fluorescent labeling reagent may comprise a cleavable group (e.g., as described herein) that is configured to be cleaved upon contact with a cleavage reagent (e.g., as described herein). Subsequent processing, such as subsequent incorporation of additional nucleotides or nucleotide analogs in a sequencing process, may be more rapid upon generation of the chemical moiety coupled to the substrate (e.g., "scarred substrate") from the fluorescently labeled substrate than such processing would be in the absence of cleavage of the cleavable group to provide the polynucleotide comprising the scarred substrate. A "scar" moiety provided herein may be a "preferred scar" to one or more polymerase enzymes, such that a polymerase enzyme may be able to perform an incorporation process (e.g., as a step in an extension process) adjacent to or in the vicinity of such a scar as well as or better than it could perform such a process in the absence of the scar. In other words, the inclusion of a scar moiety provided herein in a polynucleotide undergoing an extension process may or may not affect the processivity of a polymerase enzyme performing the extension process. The inclusion of a scar moiety provided herein in a polynucleotide undergoing an extension process may or may not affect the tolerance in the incorporation reaction (e.g., as described herein). For example, the use of polynucleotides including nucleotides comprising such scar moieties may reduce context effects, which may have the effect of simplifying base determination in a sequencing process.

In an aspect, the present disclosure provides a compound of Formula (I):

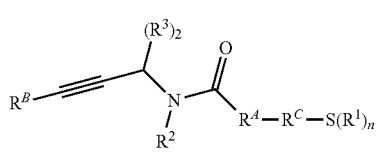

Formula (I)

or a salt thereof, wherein:
$R^A$ is an optionally substituted 5-12 membered ring system, wherein substituents on $R^A$ are independently selected from $R^4$;
$R^B$ is selected from (i) an optionally substituted monocyclic heterocycle comprising 2 or more heteroatoms and (ii) an optionally substituted bicyclic heterocycle, wherein substituents on $R^B$ are independently selected from $R^5$;
$R^C$ is selected from optionally substituted $C_{1-6}$ alkyl, optionally substituted $C_{2-6}$ alkenyl, and optionally substituted $C_{2-6}$ alkynyl, wherein substituents on $R^1$ are independently selected from $R^6$, or is absent;
$R^1$ is selected from hydrogen, halogen, —OH, —OR$^8$, =O, =S, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^1$ are independently selected from $R^6$;
$R^2$ is selected from hydrogen, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^2$ are independently selected from $R^6$;

each $R^3$ is independently selected from hydrogen, halogen, —CN, —OH, —OR$^8$, —C(=O)R$^8$, —CO$_2$R$^7$, —C(=O)N(R$^7$)$_2$, —N(R$^7$)$_2$, —NRC(=O)R$^7$, —NR$^7$C(=O)N(R$^7$)$_2$, —SR$^7$, —S(=O)R$^8$, —SO$_2$R$^8$, —SO$_2$N(R$^7$)$_2$, —NO$_2$, optionally substituted $C_1$-$C_6$ alkyl, optionally substituted $C_1$-$C_6$ alkenyl, optionally substituted $C_1$-$C_6$ alkynyl, optionally substituted monocyclic carbocycle, and optionally substituted monocyclic heterocycle, wherein optional substituents on $C_1$-$C_6$ alkyl, $C_1$-$C_6$ alkenyl, $C_1$-$C_6$ alkynyl, monocyclic carbocycle, and monocyclic heterocycle are independently selected from $R^6$;

or two $R^3$ are taken together with the atom to which they are attached to form an optionally substituted 3- to 6-membered heterocycle or carbocycle, wherein optional substituents on the 3- to 6-membered heterocycle or carbocycle are independently selected from $R^6$;

$R^4$ is selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —NR$^9$SO$_2$R$^9$, —SR$^9$, —S(=O)R$^{10}$, —SO$_2$R$^{10}$, or —SO$_2$N(R$^9$)$_2$, —NO$_2$, optionally substituted $C_1$-$C_6$ alkyl, optionally substituted $C_2$-$C_6$ alkenyl, optionally substituted $C_2$-$C_6$ alkynyl, an optionally substituted $C_3$-$C_{10}$ carbocycle, and an optionally substituted 3-10-membered heterocycle, wherein substituents on $R^4$ are independently selected from $R^6$;

$R^5$ is selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —NR$^9$SO$_2$R$^9$, —SR$^9$, —S(=O)R$^{10}$, —SO$_2$R$^{10}$, or —SO$_2$N(R$^9$)$_2$, —NO$_2$, optionally substituted $C_1$-$C_6$ alkyl, optionally substituted $C_2$-$C_6$ alkenyl, optionally substituted $C_2$-$C_6$ alkynyl, an optionally substituted $C_3$-$C_{10}$ carbocycle, and an optionally substituted 3-10-membered heterocycle, wherein substituents on $R^5$ are independently selected from $R^6$;

each $R^6$ is independently selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —SR$^9$, —S(=O)R$^{10}$, —SO$_2$R$^{10}$, —SO$_2$N(R$^9$)$_2$, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, optionally substituted monophosphate, optionally substituted diphosphate, optionally substituted triphosphate, and 3- to 6-membered heterocycle;

each $R^7$ is independently selected from hydrogen, optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;

or two $R^7$ are taken together with the atom(s) to which they are attached to form an optionally substituted 3- to 6-membered heterocycle, wherein optional substituents on the 3- to 6-membered heterocycle are independently selected from $R^6$;

each $R^8$ is independently selected from optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;

each $R^9$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle;

or two $R^9$ on the same nitrogen atom are taken together with the nitrogen to which they are attached to form a 3- to 6-membered heterocycle;

each $R^{10}$ is independently selected from $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle; and n is selected from 1, 2, 3, 4, and 5.

In some embodiments, $R^B$ is an optionally substituted bicyclic heterocycle. In some embodiments, the heteroatoms of $R^B$ are each N. In some embodiments, $R^B$ is an optionally substituted purine. In some embodiments, $R^B$ is selected from

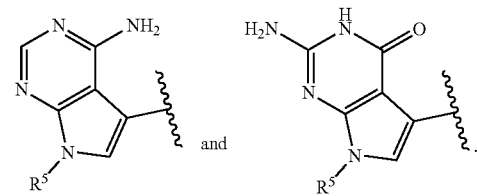

In some embodiments, $R^B$ is an optionally substituted monocyclic heterocycle comprising 2 or more heteroatoms. In some embodiments, each heteroatom of the 2 or more heteroatoms is N. In some embodiments, $R^B$ is an optionally substituted pyrimidine. In some embodiments, $R^B$ is selected from

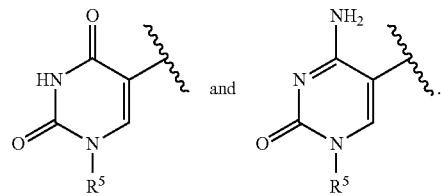

In some embodiments, $R^B$ is substituted with at least one $R^5$ selected from an optionally substituted $C_3$-$C_{10}$ carbocycle and an optionally substituted 3-10-membered heterocycle. In some embodiments, $R^B$ is substituted with at least one $R^5$ selected from an optionally substituted 5-6-membered heterocycle. In some embodiments, the optionally substituted 5-6-membered heterocycle is selected from optionally substituted ribose and deoxyribose. In some embodiments, the optionally substituted 5-6-membered heterocycle is substituted with one or more optionally substituted monophosphate, diphosphate, or triphosphate moieties.

In some embodiments, $R^A$ is an optionally substituted 5-12 membered carbocyclic ring system. In some embodiments, $R^A$ is an optionally substituted 5-12 membered heterocyclic ring system. In some embodiments, $R^A$ is an aromatic ring system. In some embodiments, $R^A$ is an optionally substituted 5-12 membered bicyclic ring system. In some embodiments, $R^A$ is an optionally substituted 5-8 membered monocyclic ring system. In some embodiments, $R^4$ is an optionally substituted phenyl moiety.

In some embodiments, each $R^4$ is independently selected from halogen, —OH, —$OR^{10}$, —$N(R^9)_2$, —$C(=O)R^9$, —$C(=O)OR^9$, —$OC(=O)R^9$, —$C(=O)N(R^9)_2$, —$NR^9C(=O)R^9$, —$NR^9C(=O)N(R^9)_2$, —$OC(=O)N(R^9)_2$, —$NR^9C(=O)OR^9$, —$OC(=O)OR^9$, and optionally substituted $C_1$-$C_6$ alkyl.

In some embodiments, $R^2$ is hydrogen.
In some embodiments, each $R^3$ is hydrogen.
In some embodiments, n is 1 and $R^1$ is hydrogen.
In some embodiments, $R^C$ is absent.
In some embodiments, the compound is a compound of Formula (II):

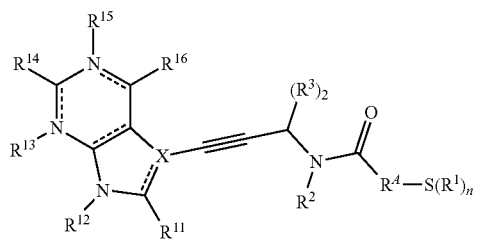

Formula (II)

or a salt thereof, wherein:
dotted lines represent bonds that may be present or absent;
X is selected from C and N;
$R^{11}$ is selected from hydrogen, halogen, —OH, —$OR^8$, —$N(R^7)_2$, —$SR^7$, =O, and optionally substituted $C_{1-6}$ alkyl;
$R^{12}$ is an optionally substituted 5-6 membered heterocycle;
$R^{13}$ is selected from hydrogen and optionally substituted $C_{1-6}$ alkyl, or is absent;
$R^{14}$ is selected from hydrogen, halogen, —OH, —$OR^8$, —$N(R^7)_2$, —$SR^7$, =O, and optionally substituted $C_{1-6}$ alkyl;
$R^{15}$ is selected from hydrogen and optionally substituted $C_{1-6}$ alkyl, or is absent; and
$R^{16}$ is selected from hydrogen, halogen, —OH, —$OR^8$, —$N(R^7)_2$, —$SR^7$, =O, and optionally substituted $C_{1-6}$ alkyl,
wherein optional substituents on $R^{11}$, $R^{13}$, $R^{14}$, $R^{15}$, and $R^{16}$ are selected from $R^{17}$; and
each $R^{17}$ is independently selected from halogen, —OH, —$OR^{10}$, —$N(R^9)_2$, —$C(=O)R^9$, —$C(=O)OR^9$, —$OC(=O)R^9$, —$C(=O)N(R^9)_2$, and —$NR^9C(=O)R^9$.

In some embodiments, X is C.
In some embodiments, $R^{12}$ is selected from optionally substituted ribose and deoxyribose. In some embodiments, $R^{12}$ is optionally substituted with an optionally substituted monophosphate, diphosphate, or triphosphate moiety.

In some embodiments, $R^2$ is hydrogen.
In some embodiments, each $R^3$ is hydrogen.
In some embodiments, $R^4$ is an optionally substituted 5-8 membered monocyclic ring system. In some embodiments, $R^4$ is an optionally substituted phenyl moiety.
In some embodiments, n is 1 and $R^1$ is hydrogen.
In some embodiments, the compound is a compound of Formula (III):

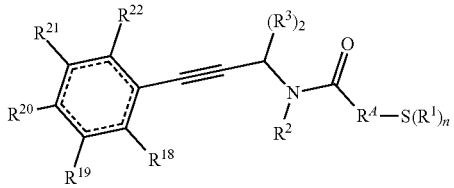

Formula (III)

or a salt thereof, wherein:
dotted lines represent bonds that may be present or absent;
$R^{18}$ is selected from hydrogen, halogen, —OH, —$OR^8$, —$N(R^7)_2$, —$SR^7$, =O, and optionally substituted $C_{1-6}$ alkyl;
$R^{19}$ is an optionally substituted 5-6 membered heterocycle;
$R^{20}$ is selected from hydrogen, halogen, —OH, —$OR^8$, —$N(R^7)_2$, —$SR^7$, =O, and optionally substituted $C_{1-6}$ alkyl;
$R^{21}$ is selected from hydrogen and optionally substituted $C_{1-6}$ alkyl, or is absent; and
$R^{22}$ is selected from hydrogen, halogen, —OH, —$OR^8$, —$N(R^7)_2$, —$SR^7$, =O, and optionally substituted $C_{1-6}$ alkyl,
wherein optional substituents on $R^{18}$, $R^{20}$, $R^{21}$, and $R^{22}$ are selected from $R^{23}$; and
each $R^{23}$ is independently selected from halogen, —OH, —$OR^{10}$, —$N(R^9)_2$, —$C(=O)R^9$, —$C(=O)OR^9$, —$OC(=O)R^9$, —$C(=O)N(R^9)_2$, and —$NR^9C(=O)R^9$.

In some embodiments, $R^{19}$ is selected from optionally substituted ribose and deoxyribose. In some embodiments, $R^{19}$ is optionally substituted with an optionally substituted monophosphate, diphosphate, or triphosphate moiety.

In some embodiments, $R^2$ is hydrogen.
In some embodiments, each $R^3$ is hydrogen.
In some embodiments, $R^4$ is an optionally substituted 5-8 membered monocyclic ring system. In some embodiments, $R^4$ is an optionally substituted phenyl moiety.
In some embodiments, n is 1 and $R^1$ is hydrogen.
In another aspect, the present disclosure provides a composition comprising a chemical moiety of Formula (IV):

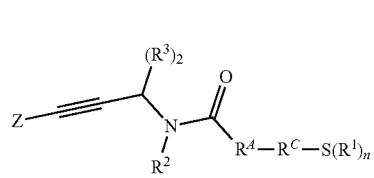

Formula (IV)

or a salt thereof, wherein:
$R^A$ is an optionally substituted 5-12 membered ring system, wherein substituents on $R^A$ are independently selected from $R^4$;
$R^C$ is selected from optionally substituted $C_{1-6}$ alkyl, optionally substituted $C_{2-6}$ alkenyl, and optionally substituted $C_{2-6}$ alkynyl, wherein substituents on $R^1$ are independently selected from $R^6$, or is absent;
$R^1$ is selected from hydrogen, halogen, —OH, —$OR^8$, =O, =S, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^1$ are independently selected from $R^6$;

$R^2$ is selected from hydrogen, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^2$ are independently selected from $R^6$;

each $R^3$ is independently selected from hydrogen, halogen, —CN, —OH, —$OR^8$, —C(=O)$R^8$, —$CO_2R^7$, —C(=O)N($R^7$)$_2$, —N($R^7$)$_2$, —NRC(=O)$R^7$, —$NR^7$C(=O)N($R^7$)$_2$, —$SR^7$, —S(=O)$R^8$, —$SO_2R^8$, —$SO_2$N($R^7$)$_2$, —$NO_2$, optionally substituted $C_1$-$C_6$ alkyl, optionally substituted $C_1$-$C_6$ alkenyl, optionally substituted $C_1$-$C_6$ alkynyl, optionally substituted monocyclic carbocycle, and optionally substituted monocyclic heterocycle, wherein optional substituents on $C_1$-$C_6$ alkyl, $C_1$-$C_6$ alkenyl, $C_1$-$C_6$ alkynyl, monocyclic carbocycle, and monocyclic heterocycle are independently selected from $R^6$;

or two $R^3$ are taken together with the atom to which they are attached to form an optionally substituted 3- to 6-membered heterocycle or carbocycle, wherein optional substituents on the 3- to 6-membered heterocycle or carbocycle are independently selected from $R^6$;

$R^4$ is selected from halogen, =O, =S, —CN, —OH, —$OR^{10}$, —N($R^9$)$_2$, —C(=O)$R^9$, —C(=O)$OR^9$, —OC(=O)$R^9$, —C(=O)N($R^9$)$_2$, —$NR^9$C(=O)$R^9$, —$NR^9$C(=O)N($R^9$)$_2$, —OC(=O)N($R^9$)$_2$, —$NR^9$C(=O)$OR^9$, —OC(=O)$OR^9$, —$NR^9SO_2R^9$, —$SR^9$, —S(=O)$R^{10}$, —$SO_2R^{10}$, or —$SO_2$N($R^9$)$_2$, —$NO_2$, optionally substituted $C_1$-$C_6$ alkyl, optionally substituted $C_2$-$C_6$ alkenyl, optionally substituted $C_2$-$C_6$ alkynyl, an optionally substituted $C_3$-$C_{10}$ carbocycle, and an optionally substituted 3-10-membered heterocycle, wherein substituents on $R^4$ are independently selected from $R^6$;

each $R^6$ is independently selected from halogen, =O, =S, —CN, —OH, —$OR^{10}$, —N($R^9$)$_2$, —C(=O)$R^9$, —C(=O)$OR^9$, —OC(=O)$R^9$, —C(=O)N($R^9$)$_2$, —$NR^9$C(=O)$R^9$, —$NR^9$C(=O)N($R^9$)$_2$, —OC(=O)N($R^9$)$_2$, —$NR^9$C(=O)$OR^9$, —OC(=O)$OR^9$, —$SR^9$, —S(=O)$R^{10}$, —$SO_2R^{10}$, —$SO_2$N($R^9$)$_2$, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, optionally substituted monophosphate, optionally substituted diphosphate, optionally substituted triphosphate, and 3- to 6-membered heterocycle;

each $R^7$ is independently selected from hydrogen, optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;

or two $R^7$ are taken together with the atom(s) to which they are attached to form an optionally substituted 3- to 6-membered heterocycle, wherein optional substituents on the 3- to 6-membered heterocycle are independently selected from $R^6$;

each $R^8$ is independently selected from optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;

each $R^9$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle;

or two $R^9$ on the same nitrogen atom are taken together with the nitrogen to which they are attached to form a 3- to 6-membered heterocycle;

each $R^{10}$ is independently selected from $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle;

n is selected from 1, 2, 3, 4, and 5; and

Z is a substrate selected from a nucleotide or nucleotide analog, cell, protein, lipid, and antibody.

In some embodiments, Z is a cell, protein, lipid, or antibody. In some embodiments, Z is a nucleotide or nucleotide analog. In some embodiments, the nucleotide or nucleotide analog is incorporated into a polynucleotide.

In some embodiments, $R^A$ is an optionally substituted 5-12 membered carbocyclic ring system. In some embodiments, $R^A$ is an optionally substituted 5-12 membered heterocyclic ring system. In some embodiments, $R^A$ is an aromatic ring system. In some embodiments, $R^A$ is an optionally substituted 5-12 membered bicyclic ring system. In some embodiments, $R^A$ is an optionally substituted 5-8 membered monocyclic ring system. In some embodiments, $R^A$ is an optionally substituted phenyl moiety.

In some embodiments, $R^C$ is absent.

In some embodiments, each $R^4$ is independently selected from halogen, —OH, —$OR^{10}$, —N($R^9$)$_2$, —C(=O)$R^9$, —C(=O)$OR^9$, —OC(=O)$R^9$, —C(=O)N($R^9$)$_2$, —$NR^9$C(=O)$R^9$, —$NR^9$C(=O)N($R^9$)$_2$, —OC(=O)N($R^9$)$_2$, —$NR^9$C(=O)$OR^9$, —OC(=O)$OR^9$, and optionally substituted $C_1$-$C_6$ alkyl.

In some embodiments, $R^2$ is hydrogen.

In some embodiments, each $R^3$ is hydrogen.

In some embodiments, n is 1 and $R^1$ is hydrogen.

In a further aspect, the present disclosure provides a modified polynucleotide comprising a compound described herein.

In some embodiments, the modified polynucleotide comprises two or more compounds described herein. In some embodiments, the two or more compounds have the same or different structures. In some embodiments, the two or more compounds are separated by at least one nucleotide. In some embodiments, the two or more compounds are included in a same strand of the modified polynucleotide.

In some embodiments, the modified polynucleotide comprises ribonucleic acid. In some embodiments, the modified polynucleotide comprises deoxyribonucleic acid.

In another aspect, the present disclosure provides a method of generating a compound described herein, comprising: (a) providing a labeled substrate comprising a substrate, a labeling moiety, and a linker coupling the labeling moiety to the substrate, wherein the linker comprises a cleavable group that is configured to be cleaved to separate the labeling moiety from the substrate; and (b) contacting the labeled substrate a cleavage reagent configured to cleave the cleavable group of the linker, thereby separating the labeling moiety and the substrate to provide the compound.

In some embodiments, the labeling moiety comprises a fluorescent label.

In some embodiments, the cleavable group comprises a disulfide bond.

In some embodiments, the cleavage reagent is selected from the group consisting of tris(2-carboxyethyl)phosphine (TCEP), dithiothreitol (DTT), tetrahydropyranyl (THP), ultraviolet (UV) light, and a combination thereof.

In some embodiments, the substrate is a nucleotide or nucleotide analog. In some embodiments, the labeled substrate is incorporated into a polynucleotide.

In a further aspect, the present disclosure provides a method of generating a composition described herein, comprising: (a) providing a labeled substrate comprising a substrate, a labeling moiety, and a linker coupling the labeling moiety to the substrate, wherein the linker comprises a cleavable group that is configured to be cleaved to separate the labeling moiety from the substrate; and (b) contacting the labeled substrate a cleavage reagent configured to cleave the cleavable group of the linker, thereby separating the labeling moiety and the substrate to provide the compound.

In some embodiments, the labeling moiety comprises a fluorescent label.

In some embodiments, the cleavable group comprises a disulfide bond.

In some embodiments, the cleavage reagent is selected from the group consisting of tris(2-carboxyethyl)phosphine (TCEP), dithiothreitol (DTT), tetrahydropyranyl (THP), ultraviolet (UV) light, and a combination thereof.

In some embodiments, the substrate is a nucleotide or nucleotide analog. In some embodiments, the labeled substrate is incorporated into a polynucleotide. In some embodiments, the substrate is a protein, lipid, cell, or antibody.

In another aspect, the present disclosure provides a method of generating a modified polynucleotide described herein, comprising: (a) providing a precursor of the compound and a template nucleic acid molecule coupled to a nucleic acid strand; (b) subjecting the template nucleic acid molecule and the precursor of the compound to conditions sufficient to incorporate the precursor of the compound into the nucleic acid strand coupled to the template nucleic acid molecule; and (c) subjecting the precursor of the compound to conditions sufficient to generate the compound from the precursor.

In some embodiments, (b) comprises using a polymerase enzyme to incorporate the compound into the nucleic acid strand. In some embodiments, the polymerase enzyme is a strand displacement polymerase enzyme.

In some embodiments, the template nucleic acid molecule comprises deoxyribonucleic acid. In some embodiments, the template nucleic acid molecule comprises ribonucleic acid.

In some embodiments, the template nucleic acid molecule is immobilized to a support.

In some embodiments, the precursor of the compound comprises a labeling moiety. In some embodiments, the labeling moiety comprises a fluorescent dye. In some embodiments, the precursor comprises the labeling moiety coupled to a substrate via linker.

In some embodiments, the substrate is a nucleotide or nucleotide analog. In some embodiments, the linker comprises a cleavable group configured to be cleaved to separate the labeling moiety from the substrate. In some embodiments, the cleavable group comprises a disulfide bond. In some embodiments, (c) comprises contacting the precursor of the compound with a cleavage reagent configured to cleave the cleavable group of the linker, thereby generating the compound.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1A:
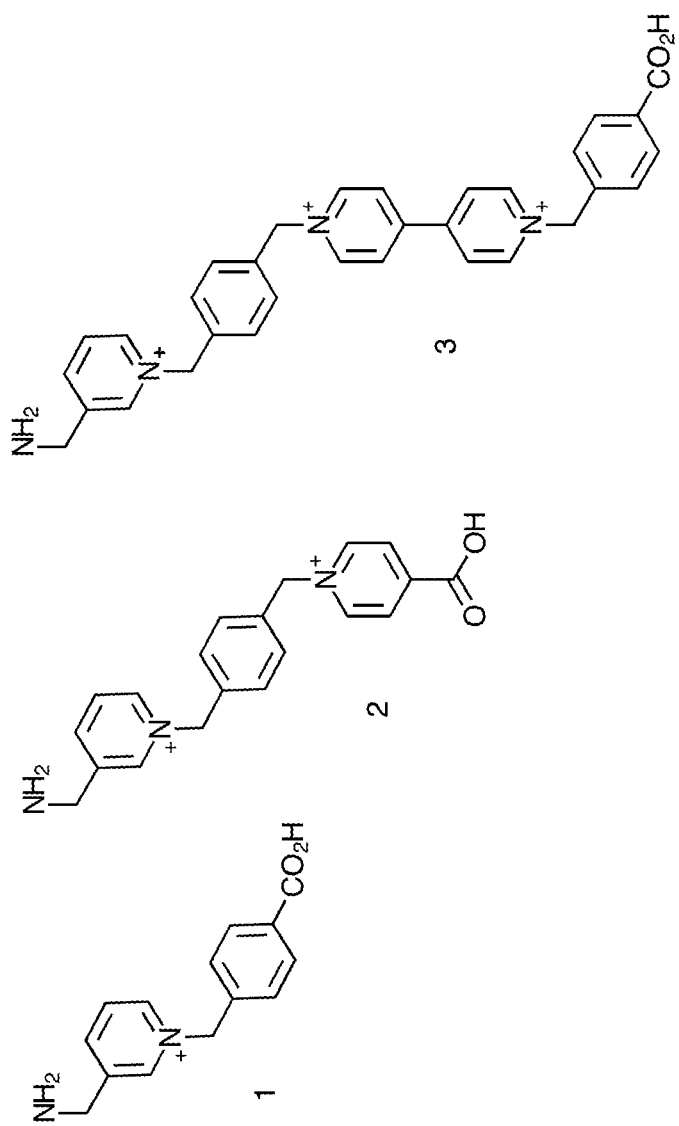
FIG. 1A shows examples of linkers of the present disclosure.
Figure 1B:
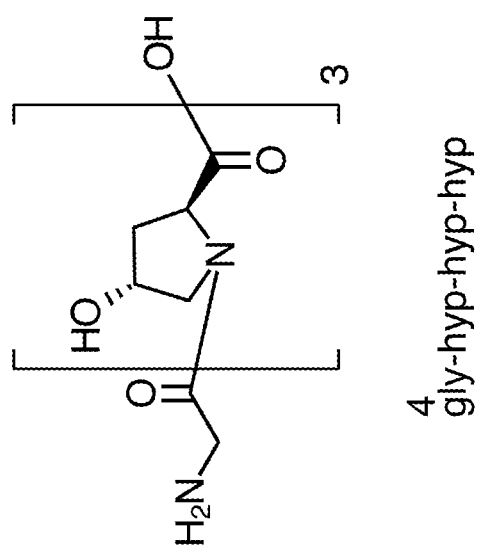
FIG. 1B shows an example of a linker of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The terms "about" and "approximately" shall generally mean an acceptable degree of error or variation for a given value or range of values, such as, for example, a degree of error or variation that is within 20 percent (%), within 15%, within 10%, or within 5% of a given value or range of values.

The term "subject," as used herein, generally refers to an individual or entity from which a biological sample (e.g., a biological sample that is undergoing or will undergo processing or analysis) may be derived. A subject may be an animal (e.g., mammal or non-mammal) or plant. The subject may be a human, dog, cat, horse, pig, bird, non-human primate, simian, farm animal, companion animal, sport animal, or rodent. A subject may be a patient. The subject may have or be suspected of having a disease or disorder, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. Alternatively or in addition to, a subject may be known to have previously had a disease or disorder. The subject may have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, *porphyria*, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease. A subject may be undergoing treatment for a disease or disorder. A subject may be symptomatic or asymptomatic of a given disease or disorder. A subject may be healthy (e.g., not suspected of having disease or disorder). A subject may have one or more risk factors for a given disease. A subject may have a given weight, height, body mass index, or other physical characteristic. A subject may have a given ethnic or racial heritage, place of birth or residence, nationality, disease or remission state, family medical history, or other characteristic.

As used herein, the term "biological sample" generally refers to a sample obtained from a subject. The biological sample may be obtained directly or indirectly from the subject. A sample may be obtained from a subject via any suitable method, including, but not limited to, spitting, swabbing, blood draw, biopsy, obtaining excretions (e.g., urine, stool, sputum, vomit, or saliva), excision, scraping, and puncture. A sample may be obtained from a subject by, for example, intravenously or intraarterially accessing the circulatory system, collecting a secreted biological sample (e.g., stool, urine, saliva, sputum, etc.), breathing, or surgically extracting a tissue (e.g., biopsy). The sample may be obtained by non-invasive methods including but not limited to: scraping of the skin or cervix, swabbing of the cheek, or collection of saliva, urine, feces, menses, tears, or semen. Alternatively, the sample may be obtained by an invasive procedure such as biopsy, needle aspiration, or phlebotomy. A sample may comprise a bodily fluid such as, but not limited to, blood (e.g., whole blood, red blood cells, leukocytes or white blood cells, platelets), plasma, serum, sweat, tears, saliva, sputum, urine, semen, mucus, synovial fluid, breast milk, colostrum, amniotic fluid, bile, bone marrow, interstitial or extracellular fluid, or cerebrospinal fluid. For example, a sample may be obtained by a puncture method to obtain a bodily fluid comprising blood and/or plasma. Such a sample may comprise both cells and cell-free nucleic acid material. Alternatively, the sample may be obtained from any other source including but not limited to blood, sweat, hair follicle, buccal tissue, tears, menses, feces, or saliva. The biological sample may be a tissue sample, such as a tumor biopsy. The sample may be obtained from any of the tissues provided herein including, but not limited to, skin, heart, lung, kidney, breast, pancreas, liver, intestine, brain, prostate, esophagus, muscle, smooth muscle, bladder, gall bladder, colon, or thyroid. The methods of obtaining provided herein include methods of biopsy including fine needle aspiration, core needle biopsy, vacuum assisted biopsy, large core biopsy, incisional biopsy, excisional biopsy, punch biopsy, shave biopsy or skin biopsy. The biological sample may comprise one or more cells. A biological sample may comprise one or more nucleic acid molecules such as one or more deoxyribonucleic acid (DNA) and/or ribonucleic acid (RNA) molecules (e.g., included within cells or not included within cells). Nucleic acid molecules may be included within cells. Alternatively or in addition to, nucleic acid molecules may not be included within cells (e.g., cell-free nucleic acid molecules). The biological sample may be a cell-free sample.

The term "cell-free sample," as used herein, generally refers to a sample that is substantially free of cells (e.g., less than 10% cells on a volume basis). A cell-free sample may be derived from any source (e.g., as described herein). For example, a cell-free sample may be derived from blood, sweat, urine, or saliva. For example, a cell-free sample may be derived from a tissue or bodily fluid. A cell-free sample may be derived from a plurality of tissues or bodily fluids. For example, a sample from a first tissue or fluid may be combined with a sample from a second tissue or fluid (e.g., while the samples are obtained or after the samples are obtained). In an example, a first fluid and a second fluid may be collected from a subject (e.g., at the same or different times) and the first and second fluids may be combined to provide a sample. A cell-free sample may comprise one or more nucleic acid molecules such as one or more DNA or RNA molecules.

A sample that is not a cell-free sample (e.g., a sample comprising one or more cells) may be processed to provide a cell-free sample. For example, a sample that includes one or more cells as well as one or more nucleic acid molecules (e.g., DNA and/or RNA molecules) not included within cells (e.g., cell-free nucleic acid molecules) may be obtained from a subject. The sample may be subjected to processing (e.g., as described herein) to separate cells and other materials from the nucleic acid molecules not included within cells, thereby providing a cell-free sample (e.g., comprising nucleic acid molecules not included within cells). The cell-free sample may then be subjected to further analysis and processing (e.g., as provided herein). Nucleic acid molecules not included within cells (e.g., cell-free nucleic acid molecules) may be derived from cells and tissues. For example, cell-free nucleic acid molecules may derive from a tumor tissue or a degraded cell (e.g., of a tissue of a body). Cell-free nucleic acid molecules may comprise any type of nucleic acid molecules (e.g., as described herein). Cell-free nucleic acid molecules may be double-stranded, single-stranded, or a combination thereof. Cell-free nucleic acid molecules may be released into a bodily fluid through secretion or cell death processes, e.g., cellular necrosis, apoptosis, or the like. Cell-free nucleic acid molecules may be released into bodily fluids from cancer cells (e.g., circulating tumor DNA (ctDNA)). Cell free nucleic acid molecules may also be fetal DNA circulating freely in a maternal blood stream (e.g., cell-free fetal nucleic acid molecules such as cffDNA). Alternatively or in addition to, cell-free nucleic acid molecules may be released into bodily fluids from healthy cells.

A biological sample may be obtained directly from a subject and analyzed without any intervening processing, such as, for example, sample purification or extraction. For example, a blood sample may be obtained directly from a subject by accessing the subject's circulatory system, removing the blood from the subject (e.g., via a needle), and transferring the removed blood into a receptacle. The receptacle may comprise reagents (e.g., anti-coagulants) such that the blood sample is useful for further analysis. Such reagents may be used to process the sample or analytes derived from the sample in the receptacle or another receptacle prior to analysis. In another example, a swab may be used to access epithelial cells on an oropharyngeal surface of the subject. Following obtaining the biological sample from the subject, the swab containing the biological sample may be contacted with a fluid (e.g., a buffer) to collect the biological fluid from the swab.

Any suitable biological sample that comprises one or more nucleic acid molecules may be obtained from a subject. A sample (e.g., a biological sample or cell-free biological sample) suitable for use according to the methods provided herein may be any material comprising tissues, cells, degraded cells, nucleic acids, genes, gene fragments, expression products, gene expression products, and/or gene expression product fragments of an individual to be tested. A biological sample may be solid matter (e.g., biological tissue) or may be a fluid (e.g., a biological fluid). In general, a biological fluid may include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, microbiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. Methods for determining sample suitability and/or adequacy are provided. A sample may include, but is not limited to, blood, plasma, tissue, cells, degraded cells, cell-free nucleic acid molecules, and/or biological material from cells or derived from cells of an individual such as cell-free nucleic acid molecules. The sample may be a heterogeneous or homogeneous population of cells, tissues, or cell-free biological material. The biological sample may be obtained using any method that can provide a sample suitable for the analytical methods described herein.

A sample (e.g., a biological sample or cell-free biological sample) may undergo one or more processes in preparation for analysis, including, but not limited to, filtration, centrifugation, selective precipitation, permeabilization, isolation, agitation, heating, purification, and/or other processes. For example, a sample may be filtered to remove contaminants or other materials. In an example, a sample comprising cells may be processed to separate the cells from other material in the sample. Such a process may be used to prepare a sample comprising only cell-free nucleic acid molecules. Such a process may consist of a multi-step centrifugation process. Multiple samples, such as multiple samples from the same subject (e.g., obtained in the same or different manners from the same or different bodily locations, and/or obtained at the same or different times (e.g., seconds, minutes, hours, days, weeks, months, or years apart)) or multiple samples from different subjects may be obtained for analysis as described herein. In an example, the first sample is obtained from a subject before the subject undergoes a treatment regimen or procedure and the second sample is obtained from the subject after the subject undergoes the treatment regimen or procedure. Alternatively or in addition to, multiple samples may be obtained from the same subject at the same or approximately the same time. Different samples obtained from the same subject may be obtained in the same or different manner. For example, a first sample may be obtained via a biopsy and a second sample may be obtained via a blood draw. Samples obtained in different manners may be obtained by different medical professionals, using different techniques, at different times, and/or at different locations. Different samples obtained from the same subject may be obtained from different areas of a body. For example, a first sample may be obtained from a first area of a body (e.g., a first tissue) and a second sample may be obtained from a second area of the body (e.g., a second tissue).

A biological sample as used herein (e.g., a biological sample comprising one or more nucleic acid molecules) may not be purified when provided in a reaction vessel. Furthermore, for a biological sample comprising one or more nucleic acid molecules, the one or more nucleic acid molecules may not be extracted when the biological sample is provided to a reaction vessel. For example, ribonucleic acid (RNA) and/or deoxyribonucleic acid (DNA) molecules of a biological sample may not be extracted from the biological sample when providing the biological sample to a reaction vessel. Moreover, a target nucleic acid (e.g., a target RNA or target DNA molecules) present in a biological sample may not be concentrated when providing the biological sample to a reaction vessel. Alternatively, a biological sample may be purified and/or nucleic acid molecules may be isolated from other materials in the biological sample.

A biological sample as described herein may contain a target nucleic acid. As used herein, the terms "template nucleic acid", "target nucleic acid", "nucleic acid molecule," "nucleic acid sequence," "nucleic acid fragment," "oligonucleotide," "polynucleotide," and "nucleic acid" generally refer to polymeric forms of nucleotides of any length, such as deoxyribonucleotides (dNTPs) or ribonucleotides (rNTPs), or analogs thereof, and may be used interchangeably. Nucleic acids may have any three-dimensional structure, and may perform any function, known or unknown. A nucleic acid molecule may have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Oligonucleotides may include one or more nonstandard nucleotide(s), nucleotide analog(s) and/or modified nucleotides. Non-limiting examples of nucleic acids include DNA, RNA, genomic DNA (e.g., gDNA such as sheared gDNA), cell-free DNA (e.g., cfDNA), synthetic DNA/RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, complementary DNA (cDNA), recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or following assembly of the nucleic acid. The sequence of nucleotides of a nucleic acid may be interrupted by non-nucleotide components. A nucleic acid may be further modified following polymerization, such as by conjugation or binding with a reporter agent.

A target nucleic acid or sample nucleic acid as described herein may be amplified to generate an amplified product. A target nucleic acid may be a target RNA or a target DNA. When the target nucleic acid is a target RNA, the target RNA may be any type of RNA, including types of RNA described elsewhere herein. The target RNA may be viral RNA and/or tumor RNA. A viral RNA may be pathogenic to a subject. Non-limiting examples of pathogenic viral RNA include human immunodeficiency virus I (HIV I), human immunodeficiency virus n (HIV 11), orthomyxoviruses, Ebola virus. Dengue virus, influenza viruses (e.g., H1N1, H3N2, H7N9, or H5N1), hepesvirus, hepatitis A virus, hepatitis B virus, hepatitis C (e.g., armored RNA-HCV virus) virus, hepatitis D virus, hepatitis E virus, hepatitis G virus, Epstein-Barr virus, mononucleosis virus, cytomegalovirus, SARS virus, West Nile Fever virus, polio virus, and measles virus.

A biological sample may comprise a plurality of target nucleic acid molecules. For example, a biological sample may comprise a plurality of target nucleic acid molecules from a single subject. In another example, a biological sample may comprise a first target nucleic acid molecule from a first subject and a second target nucleic acid molecule from a second subject.

The term "nucleotide," as used herein, generally refers to a substance including a base (e.g., a nucleobase), sugar moiety, and phosphate moiety. A nucleotide may comprise a free base with attached phosphate groups. A substance including a base with three attached phosphate groups may be referred to as a nucleoside triphosphate. When a nucleotide is being added to a growing nucleic acid molecule strand, the formation of a phosphodiester bond between the proximal phosphate of the nucleotide to the growing chain may be accompanied by hydrolysis of a high-energy phosphate bond with release of the two distal phosphates as a pyrophosphate. The nucleotide may be naturally occurring or non-naturally occurring (e.g., a modified or engineered nucleotide).

The term "nucleotide analog," as used herein, may include, but is not limited to, a nucleotide that may or may not be a naturally occurring nucleotide. For example, a nucleotide analog may be derived from and/or include structural similarities to a canonical nucleotide such as adenine-(A), thymine-(T), cytosine-(C), uracil-(U), or guanine-(G) including nucleotide. A nucleotide analog may comprise one or more differences or modifications relative to a natural nucleotide. Examples of nucleotide analogs include inosine, diaminopurine, 5-fluorouracil, 5-bromouracil, 5-chlorouracil, 5-iodouracil, hypoxanthine, xanthine, deazaxanthine, deazaguanine, isocytosine, isoguanine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-di-aminopurine, ethynyl nucleotide bases, 1-propynyl nucleotide bases, azido nucleotide bases, phosphoroselenoate nucleic acids, and modified versions thereof (e.g., by oxidation, reduction, and/or addition of a substituent such as an alkyl, hydroxyalkyl, hydroxyl, or halogen moiety). Nucleic acid molecules (e.g., polynucleotides, double-stranded nucleic acid molecules, single-stranded nucleic acid molecules, primers, adapters, etc.) may be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety, or phosphate backbone. In some cases, a nucleotide may include a modification in its phosphate moiety, including a modification to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates), and modifications with selenium moieties (e.g., phosphoroselenoate nucleic acids). A nucleotide or nucleotide analog may comprise a sugar selected from the group consisting of ribose, deoxyribose, and modified versions thereof (e.g., by oxidation, reduction, and/or addition of a substituent such as an alkyl, hydroxyalkyl, hydroxyl, or halogen moiety). A nucleotide analog may also comprise a modified linker moiety (e.g., in lieu of a phosphate moiety). Nucleotide analogs may also contain amine-modified groups, such as aminoallyl-dUTP (aa-dUTP) and aminohexylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure may provide, for example, higher density in bits per cubic mm, higher safety (resistant to accidental or purposeful synthesis of natural toxins), easier discrimination in photo-programmed polymerases, and/or lower secondary structure. Nucleotide analogs may be capable of reacting or bonding with detectable moieties for nucleotide detection.

The term "homopolymer," as used herein, generally refers to a polymer or a portion of a polymer comprising identical monomer units. A homopolymer may have a homopolymer sequence. A nucleic acid homopolymer may refer to a polynucleotide or an oligonucleotide comprising consecutive repetitions of a same nucleotide or any nucleotide variants thereof. For example, a homopolymer can be poly (dA), poly(dT), poly(dG), poly(dC), poly(rA), poly(U), poly (rG), or poly(rC). A homopolymer can be of any length. For example, the homopolymer can have a length of at least 2, 3, 4, 5, 10, 20, 30, 40, 50, 100, 200, 300, 400, 500, or more nucleic acid bases. The homopolymer can have from 10 to 500, or 15 to 200, or 20 to 150 nucleic acid bases. The homopolymer can have a length of at most 500, 400, 300, 200, 100, 50, 40, 30, 20, 10, 5, 4, 3, or 2 nucleic acid bases. A molecule, such as a nucleic acid molecule, can include one or more homopolymer portions and one or more non-homopolymer portions. The molecule may be entirely formed of a homopolymer, multiple homopolymers, or a combination of homopolymers and non-homopolymers. In nucleic acid sequencing, multiple nucleotides can be incorporated into a homopolymeric region of a nucleic acid strand. Such nucleotides may be non-terminated to permit incorporation of consecutive nucleotides (e.g., during a single nucleotide flow).

The terms "amplifying," "amplification," and "nucleic acid amplification" are used interchangeably and generally refer to generating one or more copies of a nucleic acid or a template. For example, "amplification" of DNA generally refers to generating one or more copies of a DNA molecule. An amplicon may be a single-stranded or double-stranded nucleic acid molecule that is generated by an amplification procedure from a starting template nucleic acid molecule. Such an amplification procedure may include one or more cycles of an extension or ligation procedure. The amplicon may comprise a nucleic acid strand, of which at least a portion may be substantially identical or substantially complementary to at least a portion of the starting template. Where the starting template is a double-stranded nucleic acid molecule, an amplicon may comprise a nucleic acid strand that is substantially identical to at least a portion of one strand and is substantially complementary to at least a portion of either strand. The amplicon can be single-stranded or double-stranded irrespective of whether the initial template is single-stranded or double-stranded. Amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR and touchdown PCR. Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C.C. PNAS, 1989, 86, 4076-4080 and U.S. Pat. Nos. 5,409, 811 and 5,674,716, each of which is herein incorporated by reference in its entirety.

Amplification may be clonal amplification. The term "clonal," as used herein, generally refers to a population of nucleic acids for which a substantial portion (e.g., greater than about 50%, 60%, 70%, 80%, 90%, 95%, or 99%) of its members have sequences that are at least about 50%, 60%, 70%, 80%, 90%, 95%, or 99% identical to one another. Members of a clonal population of nucleic acid molecules may have sequence homology to one another. Such members may have sequence homology to a template nucleic acid molecule. The members of the clonal population may be double stranded or single stranded. Members of a population may not be 100% identical or complementary, e.g., "errors" may occur during the course of synthesis such that a minority of a given population may not have sequence homology with a majority of the population. For example, at least 50% of the members of a population may be substantially identical to each other or to a reference nucleic acid molecule (i.e., a molecule of defined sequence used as a basis for a sequence comparison). At least 60%, at least 70%, at least 80%, at least 90%, at least 95%, at least 99%, or more of the members of a population may be substantially identical to the reference nucleic acid molecule. Two molecules may be considered substantially identical (or homologous) if the percent identity between the two molecules is at least 60%, 70%, 75%, 80%, 85%, 90%, 95%, 98%, 99%, 99.9% or greater. Two molecules may be considered substantially complementary if the percent complementarity between the two molecules is at least 60%, 70%, 75%, 80%, 85%, 90%, 95%, 98%, 99%, 99.9% or greater. A low or insubstantial level of mixing of non-homologous nucleic acids may occur, and thus a clonal population may contain a minority of diverse nucleic acids (e.g., less than 30%, e.g., less than 10%).

Useful methods for clonal amplification from single molecules include rolling circle amplification (RCA) (Lizardi et al., Nat. Genet. 19:225-232 (1998), which is incorporated herein by reference), bridge PCR (Adams and Kron, Method for Performing Amplification of Nucleic Acid with Two Primers Bound to a Single Solid Support, Mosaic Technologies, Inc. (Winter Hill, Mass.); Whitehead Institute for Biomedical Research, Cambridge, Mass., (1997); Adessi et al., Nucl. Acids Res. 28:E87 (2000); Pemov et al., Nucl. Acids Res. 33:e11(2005); or U.S. Pat. No. 5,641,658, each of which is incorporated herein by reference), polony generation (Mitra et al., Proc. Natl. Acad. Sci. USA 100:5926-5931 (2003); Mitra et al., Anal. Biochem. 320:55-65(2003), each of which is incorporated herein by reference), and clonal amplification on beads using emulsions (Dressman et al., Proc. Natl. Acad. Sci. USA 100:8817-8822 (2003), which is incorporated herein by reference) or ligation to bead-based adapter libraries (Brenner et al., Nat. Biotechnol. 18:630-634 (2000); Brenner et al., Proc. Natl. Acad. Sci. USA 97:1665-1670 (2000)); Reinartz, et al., Brief Funct. Genomic Proteomic 1:95-104 (2002), each of which is incorporated herein by reference). The enhanced signal-to-noise ratio provided by clonal amplification more than outweighs the disadvantages of the cyclic sequencing requirement.

The term "polymerizing enzyme" or "polymerase," as used herein, generally refers to any enzyme capable of catalyzing a polymerization reaction. A polymerizing enzyme may be used to extend a nucleic acid primer paired with a template strand by incorporation of nucleotides or nucleotide analogs. A polymerizing enzyme may add a new strand of DNA by extending the 3' end of an existing nucleotide chain, adding new nucleotides matched to the template strand one at a time via the creation of phosphodiester bonds. The polymerase used herein can have strand displacement activity or non-strand displacement activity. Examples of polymerases include, without limitation, a nucleic acid polymerase. An example polymerase is a Φ29 DNA polymerase or a derivative thereof. A polymerase can be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, *E. coli* DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfu-turbo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some cases, the polymerase is a single subunit polymerase. The polymerase can have high processivity, namely the capability of the polymerase to consecutively incorporate nucleotides into a nucleic acid template without releasing the nucleic acid template. In some cases, a polymerase is a polymerase modified to accept dideoxynucleotide triphosphates, such as for example, Taq polymerase having a 667Y mutation (see e.g., Tabor et al, PNAS, 1995, 92, 6339-6343, which is herein incorporated by reference in its entirety for all purposes). In some cases, a polymerase is a polymerase having a modified nucleotide binding, which may be useful for nucleic acid sequencing, with non-limiting examples that include ThermoSequenas polymerase (GE Life Sciences), AmpliTaq FS (ThermoFisher) polymerase and Sequencing Pol polymerase (Jena Bioscience). In some cases, the polymerase is genetically engineered to have discrimination against dideoxynucleotides, such as for example, Sequenase DNA polymerase (ThermoFisher).

A polymerase may be Family A polymerase or a Family B DNA polymerase. Family A polymerases include, for example, Taq, Klenow, and Bst polymerases. Family B polymerases include, for example, Vent(exo-) and Therminator polymerases. Family B polymerases are known to accept more varied nucleotide substrates than Family A polymerases. Family A polymerases are used widely in sequencing by synthesis methods, likely due to their high processivity and fidelity.

The term "complementary sequence," as used herein, generally refers to a sequence that hybridizes to another sequence. Hybridization between two single-stranded nucleic acid molecules may involve the formation of a double-stranded structure that is stable under certain conditions. Two single-stranded polynucleotides may be considered to be hybridized if they are bonded to each other by two or more sequentially adjacent base pairings. A substantial proportion of nucleotides in one strand of a double-stranded structure may undergo Watson-Crick base-pairing with a nucleoside on the other strand. Hybridization may also include the pairing of nucleoside analogs, such as deoxyinosine, nucleosides with 2-aminopurine bases, and the like, that may be employed to reduce the degeneracy of probes, whether or not such pairing involves formation of hydrogen bonds.

The term "denaturation," as used herein, generally refers to separation of a double-stranded molecule (e.g., DNA) into single-stranded molecules. Denaturation may be complete or partial denaturation. In partial denaturation, a single-stranded region may form in a double-stranded molecule by denaturation of the two deoxyribonucleic acid (DNA) strands flanked by double-stranded regions in DNA.

The term "melting temperature" or "melting point," as used herein, generally refers to the temperature at which at least a portion of a strand of a nucleic acid molecule in a sample has separated from at least a portion of a complementary strand. The melting temperature may be the temperature at which a double-stranded nucleic acid molecule has partially or completely denatured. The melting temperature may refer to a temperature of a sequence among a plurality of sequences of a given nucleic acid molecule, or a temperature of the plurality of sequences. Different regions of a double-stranded nucleic acid molecule may have different melting temperatures. For example, a double-stranded nucleic acid molecule may include a first region having a first melting point and a second region having a second melting point that is higher than the first melting point. Accordingly, different regions of a double-stranded nucleic acid molecule may melt (e.g., partially denature) at different temperatures. The melting point of a nucleic acid molecule or a region thereof (e.g., a nucleic acid sequence) may be determined experimentally (e.g., via a melt analysis or other procedure) or may be estimated based upon the sequence and length of the nucleic acid molecule. For example, a software program such as MELTING may be used to estimate a melting temperature for a nucleic acid sequence (Dumousseau M, Rodriguez N, Juty N, Le Novere N, MELTING, a flexible platform to predict the melting temperatures of nucleic acids. BMC Bioinformatics. 2012 May 16; 13:101. doi: 10.1186/1471-2105-13-101). Accordingly, a melting point as described herein may be an estimated melting point. A true melting point of a nucleic acid sequence may vary based upon the sequences or lack thereof adjacent to the nucleic acid sequence of interest as well as other factors.

The term "sequencing," as used herein, generally refers to a process for generating or identifying a sequence of a biological molecule, such as a nucleic acid molecule or a polypeptide. Such sequence may be a nucleic acid sequence, which may include a sequence of nucleic acid bases (e.g., nucleobases). Sequencing may be, for example, single molecule sequencing, sequencing by synthesis, sequencing by hybridization, or sequencing by ligation. Sequencing may be performed using template nucleic acid molecules immobilized on a support, such as a flow cell or one or more beads. A sequencing assay may yield one or more sequencing reads corresponding to one or more template nucleic acid molecules.

The term "read," as used herein, generally refers to a nucleic acid sequence, such as a sequencing read. A sequencing read may be an inferred sequence of nucleic acid bases (e.g., nucleotides) or base pairs obtained via a nucleic acid sequencing assay. A sequencing read may be generated by a nucleic acid sequencer, such as a massively parallel array sequencer (e.g., Illumina or Pacific Biosciences of California). A sequencing read may correspond to a portion, or in some cases all, of a genome of a subject. A sequencing read may be part of a collection of sequencing reads, which may be combined through, for example, alignment (e.g., to a reference genome), to yield a sequence of a genome of a subject.

The term "detector," as used herein, generally refers to a device that is capable of detecting or measuring a signal, such as a signal indicative of the presence or absence of an incorporated nucleotide or nucleotide analog. A detector may include optical and/or electronic components that may detect and/or measure signals. Non-limiting examples of detection methods involving a detector include optical detection, spectroscopic detection, electrostatic detection, and electrochemical detection. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

The term "support", as used herein, generally refers to any solid or semi-solid article on which reagents such as nucleic acid molecules may be immobilized. Nucleic acid molecules may be synthesized, attached, ligated, or otherwise immobilized. Nucleic acid molecules may be immobilized on a support by any method including, but not limited to, physical adsorption, by ionic or covalent bond formation, or combinations thereof. A support may be 2-dimensional (e.g., a planar 2D support) or 3-dimensional. In some cases, a support may be a component of a flow cell and/or may be included within or adapted to be received by a sequencing instrument. A support may include a polymer, a glass, or a metallic material. Examples of supports include a membrane, a planar support, a microtiter plate, a bead (e.g., a magnetic bead), a filter, a test strip, a slide, a cover slip, and a test tube. A support may comprise organic polymers such as polystyrene, polyethylene, polypropylene, polyfluoroethylene, polyethyleneoxy, and polyacrylamide (e.g., polyacrylamide gel), as well as co-polymers and grafts thereof. A support may comprise latex or dextran. A support may also be inorganic, such as glass, silica, gold, controlled-pore-glass (CPG), or reverse-phase silica. The configuration of a support may be, for example, in the form of beads, spheres, particles, granules, a gel, a porous matrix, or a support. In some cases, a support may be a single solid or semi-solid article (e.g., a single particle), while in other cases a support may comprise a plurality of solid or semi-solid articles (e.g., a collection of particles). Supports may be planar, substantially planar, or non-planar. Supports may be porous or non-porous, and may have swelling or non-swelling characteristics. A support may be shaped to comprise one or more wells, depressions, or other containers, vessels, features, or locations. A plurality of supports may be configured in an array at various locations. A support may be addressable (e.g., for robotic delivery of reagents), or by detection approaches, such as scanning by laser illumination and confocal or deflective light gathering. For example, a support may be in optical and/or physical communication with a detector. Alternatively, a support may be physically separated from a detector by a distance. An amplification support (e.g., a bead) can be placed within or on another support (e.g., within a well of a second support).

The term "label," as used herein, generally refers to a moiety that is capable of coupling with a species, such as, for example a nucleotide analog. A label may include an affinity moiety. In some cases, a label may be a detectable label that emits a signal (or reduces an already emitted signal) that can be detected. In some cases, such a signal may be indicative of incorporation of one or more nucleotides or nucleotide analogs. In some cases, a label may be coupled to a nucleotide or nucleotide analog, which nucleotide or nucleotide analog may be used in a primer extension reaction. In some cases, the label may be coupled to a nucleotide analog after a primer extension reaction. The label, in some cases, may be reactive specifically with a nucleotide or nucleotide analog. Coupling may be covalent or non-covalent (e.g., via ionic interactions, Van der Waals forces, etc.). In some cases, coupling may be via a linker, which may be cleavable, such as photo-cleavable (e.g., cleavable under ultra-violet light), chemically-cleavable (e.g., via a reducing agent, such as dithiothreitol (DTT), tris(2-carboxyethyl)phosphine (TCEP), tris(hydroxypropyl)phosphine (THP) or enzymatically cleavable (e.g., via an esterase, lipase, peptidase or protease). In some cases, the label may be luminescent; that is, fluorescent or phosphorescent. For example, the label may be or comprise a fluorescent moiety (e.g., a dye). Dyes and labels may be incorporated into nucleic acid sequences. Dyes and labels may also be incorporated into or attached to linkers, such as linkers for linking one or more beads to one another. For example, labels such as fluorescent moieties may be linked to nucleotides or nucleotide analogs via a linker (e.g., as described herein). Non-limiting examples of dyes include SYBR green, SYBR blue, DAPI, propidium iodine, Hoechst, SYBR gold, ethidium bromide, acridine, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, propidium iodide, hexidium iodide, dihydroethidium, ethidium homodimer-1 and -2, ethidium monoazide, ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, OBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO labels (e.g., SYTO-40, -41, -42, -43, -44, and -45 (blue); SYTO-13, -16, -24, -21, -23, -12, -11, -20, -22, -15, -14, and -25 (green); SYTO-81, -80, -82, -83, -84, and -85 (orange); and SYTO-64, -17, -59, -61, -62, -60, and -63 (red)), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor labels (e.g., AlexaFluor 350, 405, 430, 488, 532, 546, 555, 568, 594, 610, 633, 635, 647, 660, 680, 700, 750, and 790 dyes), DyLight labels (e.g., DyLight 350, 405, 488, 550, 594, 633, 650, 680, 755, and 800 dyes), Black Hole Quencher Dyes (Biosearch Technologies) (e.g., BH1-0, BHQ-1, BHQ-3, and BHQ-10), QSY Dye fluorescent quenchers (Molecular Probes/Invitrogen) (e.g., QSY7, QSY9, QSY21, and QSY35), Dabcyl, Dabsyl, Cy5Q, Cy7Q, Dark Cyanine dyes (GE Healthcare), Dy-Quenchers (Dyomics) (e.g., DYQ-660 and DYQ-661), ATTO fluorescent quenchers (ATTO-TEC GmbH) (e.g., ATTO 540Q, ATTO 580Q, ATTO 612Q, Atto532 [e.g., Atto 532 succinimidyl ester], and Atto633), and other fluorophores and/or quenchers. Additional examples are included in structures provided herein. Dyes included in structures provided herein are contemplated for use in combination with any linker and substrate described herein. A fluorescent dye may be excited by application of energy corresponding to the visible region of the electromagnetic spectrum (e.g., between about 430-770 nanometers (nm)). Excitation may be done using any useful apparatus, such as a laser and/or light emitting diode. Optical elements including, but not limited to, mirrors, waveplates, filters, monochromaters, gratings, beam splitters, and lenses may be used to direct light to or from a fluorescent dye. A fluorescent dye may emit light (e.g., fluoresce) in the visible region of the electromagnetic spectrum ((e.g., between about 430-770 nm). A fluorescent dye may be excited over a single wavelength or a range of wavelengths. A fluorescent dye may be excitable by light in the red region of the visible portion of the electromagnetic spectrum (about 625-740 nm) (e.g., have an excitation maximum in the red region of the visible portion of the electromagnetic spectrum). Alternatively or in addition to, fluorescent dye may be excitable by light in the green region of the visible portion of the electromagnetic spectrum (about 500-565 nm) (e.g., have an excitation maximum in the green region of the visible portion of the electromagnetic spectrum). A fluorescent dye may emit signal in the red region of the visible portion of the electromagnetic spectrum (about 625-740 nm) (e.g., have an emission maximum in the red region of the visible portion of the electromagnetic spectrum). Alternatively or in addition to, fluorescent dye may emit signal in the green region of the visible portion of the electromagnetic spectrum (about 500-565 nm) (e.g., have an emission maximum in the green region of the visible portion of the electromagnetic spectrum).

Labels may be quencher molecules. The term "quencher," as used herein, generally refers to molecules that may be energy acceptors. A quencher may be a molecule that can reduce an emitted signal. For example, a template nucleic acid molecule may be designed to emit a detectable signal. Incorporation of a nucleotide or nucleotide analog comprising a quencher can reduce or eliminate the signal, which reduction or elimination is then detected. Luminescence from labels (e.g., fluorescent moieties, such as fluorescent moieties linked to nucleotides or nucleotide analogs) may also be quenched (e.g., by incorporation of other nucleotides that may or may not comprise labels). In some cases, as described elsewhere herein, labelling with a quencher can occur after nucleotide or nucleotide analog incorporation (e.g., after incorporation of a nucleotide or nucleotide analog comprising a fluorescent moiety). In some cases, the label may be a type that does not self-quench or exhibit proximity quenching. Non-limiting examples of a label type that does not self-quench or exhibit proximity quenching include Bimane derivatives such as Monobromobimane. The term "proximity quenching," as used herein, generally refers to a phenomenon where one or more dyes near each other may exhibit lower fluorescence as compared to the fluorescence they exhibit individually. In some cases, the dye may be subject to proximity quenching wherein the donor dye and acceptor dye are within 1 nm to 50 nm of each other. Examples of quenchers include, but are not limited to, Black Hole Quencher Dyes (Biosearch Technologies) (e.g., BH1-0, BHQ-1, BHQ-3, and BHQ-10), QSY Dye fluorescent quenchers (Molecular Probes/Invitrogen) (e.g., QSY7, QSY9, QSY21, and QSY35), Dabcyl, Dabsyl, Cy5Q, Cy7Q, Dark Cyanine dyes (GE Healthcare), Dy-Quenchers (Dyomics) (e.g., DYQ-660 and DYQ-661), and ATTO fluorescent quenchers (ATTO-TEC GmbH) (e.g., ATTO 540Q, ATTO 580Q, and ATTO 612Q). Fluorophore donor molecules may be used in conjunction with a quencher. Examples of fluorophore donor molecules that can be used in conjunction with quenchers include, but are not limited to, fluorophores such as Cy3B, Cy3, or Cy5; Dy-Quenchers (Dyomics) (e.g., DYQ-660 and DYQ-661); and ATTO fluorescent quenchers (ATTO-TEC GmbH) (e.g., ATTO 540Q, 580Q, and 612Q).

The term "labeling fraction," as used herein, generally refers to the ratio of dye-labeled nucleotide or nucleotide analog to natural/unlabeled nucleotide or nucleotide analog of a single canonical type in a flow solution. The labeling fraction can be expressed as the concentration of the labeled nucleotide or nucleotide analog divided by the sum of the concentrations of labeled and unlabeled nucleotide or nucleotide analog. The labeling fraction may be expressed as a % of labeled nucleotides included in a solution (e.g., a nucleotide flow). The labeling fraction may be at least about 0.5%, 1%, 2%, 3%, 4%, 5, 10, 15%, 20%, 30%, 40%, 50%, 60%, 70%, 80%, 90%, or higher. For example, the labeling fraction may be at least about 20%. The labeling fraction may be about 100%. The labeling fraction may also be expressed as a ratio of labeled nucleotides to unlabeled nucleotides included in a solution. For example, the ratio of labeled nucleotides to unlabeled nucleotides may be at least about 1:5, 1:4, 1:3, 1:2, 1:1, 2:1, 3:1, 4:1, 5:1, or higher. For example, the ratio of labeled nucleotides to unlabeled nucleotides may be at least about 1:4. For example, the ratio of labeled nucleotides to unlabeled nucleotides may be at least about 1:1. For example, the ratio of labeled nucleotides to unlabeled nucleotides may be at least about 5:1.

The term "labeled fraction," as used herein, generally refers to the actual fraction of labeled nucleic acid (e.g., DNA) resulting after treatment of a primer-template with a mixture of the dye-labeled and natural nucleotide or nucleotide analog. The labeled fraction may be about the same as the labeling fraction. For example, if 20% of nucleotides in a nucleotide flow are labeled, about 20% of nucleotides incorporated into a growing nucleic acid strand (e.g., during nucleic acid sequencing) may be labeled. Alternatively, the labeled fraction may be greater than the labeled fraction. For example, if 20% of nucleotides in a nucleotide flow are labeled, greater than 20% of nucleotides incorporated into a growing nucleic acid strand (e.g., during nucleic acid sequencing) may be labeled. Alternatively, the labeled fraction may be less than the labeled fraction. For example, if 20% of nucleotides in a nucleotide flow are labeled, less than 20% of nucleotides incorporated into a growing nucleic acid strand (e.g., during nucleic acid sequencing) may be labeled.

When a solution including less than 100% labeled nucleotides or nucleotide analogs is used in an incorporation process such as a sequencing process (e.g., as described herein), both labeled ("bright") and unlabeled ("dark") nucleotides or nucleotide analogs may be incorporated into a growing nucleic acid strand. The term "tolerance," as used herein, generally refers to the ratio of the labeled fraction (e.g., "bright" incorporated fraction) to the labeling fraction (e.g., "bright" fraction in solution). For example, if a labeling fraction of 0.2 is used resulting in a labeled fraction of 0.4 the tolerance is 2. Similarly, if an incorporation process such as a sequencing process is performed using 2.5% labeled fraction in solution ($b_f$, bright solution fraction) and 5% is labeled ($b_i$, bright incorporated fraction), the tolerance may be 2 (e.g., tolerance). This model may be linear for low labeling fractions (e.g., 10% or lower labeling fraction). For higher labeling fractions, tolerance may take into account competing dark incorporation. Tolerance may refer to a comparison of the ratio of bright incorporated fraction to dark incorporated fraction ($b_i/d_i$) to the ratio of bright solution fraction to dark solution fraction ($b_f/d_f$):

Tolerance=$b_i/d_i/b_f/d_f$ where $d_i$=1−$b_i$ (e.g., dark incorporated fraction and bright incorporated fraction sum to 1 assuming 100% bright fraction is normalized to 1)

Though $d_i$ cannot easily be measured, $b_i$, the bright incorporated fraction, can be measured (e.g., as described herein) and used to determine tolerance by fitting a curve of bright solution fraction ($b_f$) vs. bright incorporated fraction ($b_i$):

$$b_i = \frac{tol(b_f/d_f)}{1 + tol(b_f/d_f)}$$

A "positive" tolerance number (>1) indicates that at 50% labeling fraction, more than 50% is labeled. A "negative" tolerance number (<1) indicates that at 50% labeling fraction, less than 50% is labeled.

The term "context," as used herein, generally refers to the sequence of the neighboring nucleotides, or context, has been observed to affect the tolerance in an incorporation reaction. The nature of the enzyme, the pH and other factors may also affect the tolerance. Reducing context effects to a minimum greatly simplifies base determination.

The term "scar," as used herein, generally refers to a residue left on a previously labeled nucleotide or nucleotide analog after cleavage of an optical (e.g., fluorescent) dye and, optionally, all or a portion of a linker attaching the optical dye to the nucleotide or nucleotide analog. Examples of scars include, but are not limited to, hydroxyl moieties (e.g., resulting from cleavage of an azidomethyl group, hydrocarbyldithiomethyl linkage, or 2-nitrobenzyloxy linkage), thiol moieties (e.g., resulting from cleavage of a disulfide linkage), and benzyl moieties. For example, a scar may comprise an aromatic group such as a phenyl or benzyl group. The size and nature of a scar may affect subsequent incorporations.

The term "misincorporation," as used herein, generally refers to occurrences when the DNA polymerase incorporates a nucleotide, either labeled or unlabeled, that is not the correct Watson-Crick partner for the template base. Misincorporation can occur more frequently in methods that lack competition of all four bases in an incorporation event, and leads to strand loss, and thus limits the read length of a sequencing method.

The term "mispair extension", as used herein, generally refers to occurrences when the DNA polymerase incorporates a nucleotide, either labeled or unlabeled, that is not the correct Watson-Crick partner for the template base, then subsequently incorporates the correct Watson-Crick partner for the following base. Mispair extension generally results in lead phasing and limits the read length of a sequencing method.

Regarding quenching, dye-dye quenching between two dye moieties linked to different nucleotides (e.g., adjacent nucleotides in a growing nucleic acid strand, or nucleotides in a nucleic acid strand that are separated by one or more other nucleotides) may be strongly dependent on the distance between the two dye moieties. The distance between two dye moieties may be at least partially dependent on the properties of linkers connecting the two dye moieties to respective nucleotides or nucleotide analogs, including the linker compositions and functional lengths. Features of the linkers, including composition and functional length, may be affected by temperature, solvent, pH and salt concentration (e.g., within a solution). Quenching may also vary based on the nature of the dyes used. Quenching may also take place between dye moieties and nucleobase moieties (e.g., between a fluorescent dye and a nucleobase of a nucleotide with which it is associated). Controlling quenching phenomena may be a key feature of the methods described herein.

Regarding flows, a nucleotide flow can consist of a mixture of labeled and unlabeled nucleotides or nucleotide analogs (e.g., nucleotides or nucleotide analogs of a single canonical type). For example, a solution comprising a plurality of optically (e.g., fluorescently) labeled nucleotides and a plurality of unlabeled nucleotides may be contacted with, e.g., a sequencing template (as described herein). The plurality of optically labeled nucleotides and a plurality of unlabeled nucleotides may each comprise the same canonical nucleotide or nucleotide analog. A flow may include only labeled nucleotides or nucleotide analogs. Alternatively, a flow may include only unlabeled nucleotides or nucleotide analogs. A flow may include a mixture of nucleotide or nucleotide analogs of different types (e.g., A and G).

A wash flow (e.g., a solution comprising a buffer) may be used to remove any nucleotides that are not incorporated into a nucleic acid complex (e.g., a sequencing template, as described herein). A cleavage flow (e.g., a solution comprising a cleavage reagent) may be used to remove dye moieties (e.g., fluorescent dye moieties) from optically (e.g., fluorescently) labeled nucleotides or nucleotide analogs. In some cases, different dyes (e.g., fluorescent dyes) may be removable using different cleavage reagents. In other cases, different dyes (e.g., fluorescent dyes) may be removable using the same cleavage reagents. Cleavage of dye moieties from optically labeled nucleotides or nucleotide analogs may comprise cleavage of all or a portion of a linker connecting a nucleotide or nucleotide analog to a dye moiety.

The term "cycle," as used herein, generally refers to a process in which a nucleotide flow, a wash flow, and a cleavage flow corresponding to each canonical nucleotide (e.g., dATP, dCTP, dGTP, and dTTP or dUTP, or modified versions thereof) are used (e.g., provided to a sequencing template, as described herein). Multiple cycles may be used to sequence and/or amplify a nucleic acid molecule. The order of nucleotide flows can be varied.

Phasing can be lead or lag phasing. Lead phasing generally refers to the phenomenon in which a population of strands show incorporation of a nucleotide a flow ahead of the expected cycle (e.g., due to contamination in the system). Lag phasing refers to the phenomenon in which a population of strands shows incorporation of a nucleotide a flow behind the expected cycle (e.g., due to incompletion of extension in an earlier cycle).

Compounds and chemical moieties described herein, including linkers, may contain one or more asymmetric centers and thus give rise to enantiomers, diastereomers, and other stereoisomeric forms that are defined, in terms of absolute stereochemistry, as (R)- or (S)-, and, in terms of relative stereochemistry, as (D)- or (L)-. The D/L system relates molecules to the chiral molecule glyceraldehyde and is commonly used to describe biological molecules including amino acids. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a phenyl ring. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley and Sons, Inc., 1981, herein incorporated by reference for this disclosure). Stereoisomers may also be obtained by stereoselective synthesis.

Compounds and chemical moieties described herein, including linkers, may exist as tautomers. A "tautomer" refers to a molecule wherein a proton shift from one atom of a molecule to another atom of the same molecule is possible. In circumstances where tautomerization is possible, a chemical equilibrium of the tautomers will exist. Unless otherwise stated, chemical structures depicted herein are intended to include structures which are different tautomers of the structures depicted. For example, the chemical structure depicted with an enol moiety also includes the keto tautomer form of the enol moiety. The exact ratio of the tautomers depends on several factors, including physical state, temperature, solvent, and pH. Some examples of tautomeric equilibrium include:

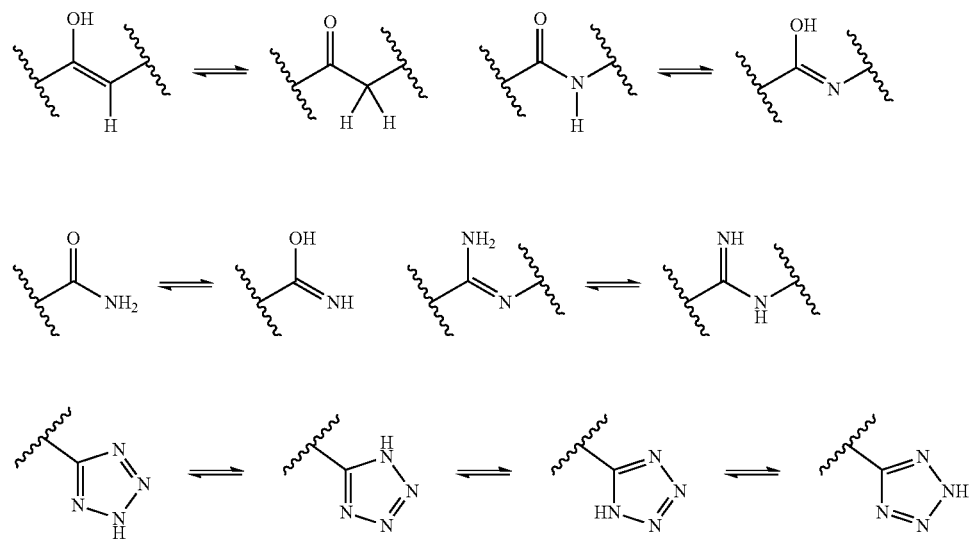

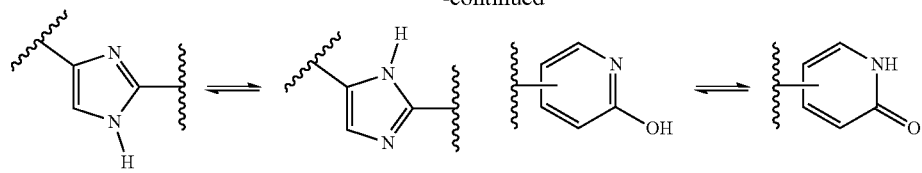

Compounds and chemical moieties described herein, including linkers and dyes, may be provided in different enriched isotopic forms. For example, compounds may be enriched in the content of $^2H$, $^3H$, $^{11}C$, $^{13}C$ and/or $^{14}C$. For example, a linker, substrate (e.g., nucleotide or nucleotide analog), or dye may be deuterated in at least one position. In some examples, a linker, substrate (e.g., nucleotide or nucleotide analog), or dye may be fully deuterated. Such deuterated forms can be made by the procedure described in U.S. Pat. Nos. 5,846,514 and 6,334,997, each of which are herein incorporated by reference in their entireties. As described in U.S. Pat. Nos. 5,846,514 and 6,334,997, deuteration can improve the metabolic stability and or efficacy, thus increasing the duration of action of drugs.

Unless otherwise stated, structures depicted and described herein are intended to include compounds which differ only in the presence of one or more isotopically enriched atoms. For example, compounds and chemical moieties having the present structures except for the replacement of a hydrogen by a deuterium or tritium, or the replacement of a carbon by $^{13}C$- or $^{14}C$-enriched carbon are within the scope of the present disclosure.

The compounds and chemical moieties of the present disclosure may contain unnatural proportions of atomic isotopes at one or more atoms that constitute such compounds. For example, a compound or chemical moiety such as a linker, substrate (e.g., nucleotide or nucleotide analog), or dye, or a combination thereof, may be labeled with one or more isotopes, such as deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$ $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}C_1$, $^{37}C_1$, $^{79}Br$, $^{81}Br$, and $^{125}I$ are all contemplated. All isotopic variations of the compounds and chemical moieties described herein, whether radioactive or not, are encompassed within the scope of the present disclosure.

Linkers for Optical Detection

The present disclosure provides an optical (e.g., fluorescent) labeling reagent comprising a dye (e.g., fluorescent dye) and a linker that is connected to the dye and capable of associating with a substrate to be optically (e.g., fluorescently) labeled. The substrate can be any suitable molecule, analyte, cell, tissue or surface that is to be optically labeled. Examples include cells, including eukaryotic cells, prokaryotic cells, healthy cells, and diseased cells; cellular receptors; antibodies; proteins; lipids; metabolites; probes; reagents; nucleotides and nucleotide analogs; and nucleic acid molecules. The association between the linker and the substrate can be any suitable association including a covalent or non-covalent bond, such as an association between a purine-containing nucleotide and a pyrimidine-containing nucleotide in a nucleic acid molecule. In some cases, such an association may be a biotin-avidin interaction. In other cases, the association between the linker and the substrate may be via a propargylamino moiety. In some cases, the association between the linker and the substrate may be via an amide bond (e.g., a peptide bond).

A linker can be semi-rigid. The semi-rigid nature of the linker can be most readily achieved by use of structure that comprises a series of ring systems (e.g., aliphatic and aromatic rings). As used herein, a ring (e.g., ring structure) is a cyclic moiety comprising any number of atoms connected in a closed, essentially circular fashion, as used in the field of organic chemistry. A ring may be defined by any number of atoms. For example, a ring may include between 3-12 atoms, such as between 3-12 carbon atoms. In certain examples, a ring may be a five-membered ring (i.e., a pentagon) or a six-membered ring (i.e., a hexagon). A ring can be aromatic or non-aromatic. A ring may be aliphatic. A ring may comprise one or more double bonds.

A ring (e.g., ring structure) may be a component of a ring system that may comprise one or more ring structures (e.g., a multi-cycle system). For example, a ring system may comprise a monocycle. In another example, a ring system may be a bicycle or bridged system. A ring structure may be a carbocycle or component thereof formed of carbon atoms. A carbocycle may be a saturated, unsaturated, or aromatic ring in which each atom of the ring is carbon. A carbocycle includes 3- to 10-membered monocyclic rings, 4- to 12-membered bicyclic rings (e.g., 6- to 12-membered bicyclic rings), and 5- to 12-membered bridged rings. Each ring of a bicyclic carbocycle may be selected from saturated, unsaturated, and aromatic rings. For example, a bicyclic carbocycle may include an aromatic ring (e.g., phenyl) fused to a saturated or unsaturated ring (e.g., cyclohexane, cyclopentane, or cyclohexene). A bicyclic carbocycle may include any combination of saturated, unsaturated, and aromatic bicyclic rings, as valence permits. A bicyclic carbocycle may include any combination of ring sizes such as 4-5 fused ring systems, 5-5 fused ring systems, 5-6 fused ring systems, and 6-6 fused ring systems. A carbocycle may be, for example, cyclopropyl, cyclobutyl, cyclopentyl, cyclohexyl, cyclohexenyl, adamantyl, phenyl, indanyl, or naphthyl. A saturated carbocycle includes no multiple bonds (e.g., double or triple bonds). A saturated carbocycle may be, for example, cyclopropane, cyclobutane, cyclopentane, or cyclohexane. An unsaturated carbocycle includes at least one multiple bond (e.g., double or triple bond) but is not an aromatic carbocycle. An unsaturated carbocycle may be, for example, cyclohexadiene, cyclohexene, or cyclopentene. Other examples of carbocycles include, but are not limited to, cyclopropane, cyclobutane, cyclopentane, cyclopentadiene, cyclohexane, cycloheptane, cycloheptene, naphthalene, and adamantine. An aromatic carbocycle (e.g., aryl moiety) may be, for example, phenyl, naphthyl, or dihydronaphthyl.

In some cases, a ring may include one or more heteroatoms, such as one or more oxygen, nitrogen, silicon, phosphorous, boron, or sulfur atoms. A ring may be a heterocycle or component thereof including one or more heteroatoms. A heterocycle may be a saturated, unsaturated, or aromatic ring in which at least one atom is a heteroatom. A heteroatom includes 3- to 10-membered monocyclic rings, 6- to 12-membered bicyclic rings, and 6- to 12-membered bridged rings. A bicyclic heterocycle may include any combination of saturated, unsaturated and aromatic bicyclic rings, as valence permits. For example, a heteroaromatic ring (e.g., pyridyl) may be fused to a saturated or unsaturated ring (e.g., cyclohexane, cyclopentane, morpholine, piperidine or cyclohexene). A bicyclic heterocycle may include any combination of ring sizes such as 4-5 fused ring systems, 5-5 fused ring systems, 5-6 fused ring systems, and 6-6 fused ring systems. An unsaturated heterocycle includes at least one multiple bond (e.g., double or triple bond) but is not an aromatic heterocycle. An unsaturated heterocycle may be, for example, dihydropyrrole, dihydrofuran, oxazoline, pyrazoline, or dihydropyridine. Additional examples of heterocycles include, but are not limited to, indole, benzothiophene, benzthiazole, benzoxazole, benzimidazole, oxazolopyridine, imidazopyridine, thiazolopyridine, furan, oxazole, pyrrole, pyrazole, imidazole, thiophene, thiazole, isothiazole, and isoxazole. A heteroaryl moiety may be an aromatic single ring structure, such as a 5- to 7-membered ring, including at least one heteroatom, such as one to four heteroatoms. Alternatively, a heteroaryl moiety may be a polycyclic ring system having two or more cyclic rings in which two or more atoms are common to two adjoining rings wherein at least one of the rings is heteroaromatic. Heteroaryl groups include, for example, pyrrole, furan, thiophene, imidazole, oxazole, thiazole, pyrazole, pyridine, pyrazine, pyridazine, and pyrimidine, and the like.

A ring can be substituted or un-substituted. A substituent replaces a hydrogen atom on one or more atoms of a ring or a substitutable heteroatom of a ring (e.g., NH or $NH_2$). Substitution is in accordance with permitted valence of the various components of the ring system and provides a stable compound (e.g., a compound that does not undergo spontaneous transformation by, for example, rearrangement, elimination, or cyclization). A substituent may replace a single hydrogen atom or multiple hydrogen atoms (e.g., on the same ring atom or different ring atoms). A substituent on a ring may be, for example, halogen, hydroxy, oxo, thioxo, thiol, amido, amino, carboxy, nitrilo, cyano, nitro, imino, oximo, hydrazino, alkoxy, alkenyl, alkynyl, aryl, aralkyl, aralkenyl, aralkynyl, cycloalkyl, cycloalkylalkyl, alkylcycloalkyl, heterocycloalkyl, heterocycyl, alkylheterocycyl, or any other useful substituent. A substituent may be water-soluble. Examples of water-soluble substituents include, but are not limited to, a pyridinium, an imidazolium, a quaternary ammonium group, a sulfonate, a phosphate, an alcohol, an amine, an imine, a nitrile, an amide, a thiol, a carboxylic acid, a polyether, an aldehyde, a boronic acid, and a boronic ester.

A linker can have any number of rings, including at least 1, 2, 3, 4, 5, 6, 7, 8, 9, 10, 11, 12, 13, 14, 15, 16, 17, 18, 19, 20, or more rings. The rings can share an edge in some cases (e.g., be components of a bicyclic ring system). In general, the ring portion of the linker can provide a degree of physical rigidity to the linker and/or can serve to physically separate the dye (e.g., fluorescent dye) on one end of the linker from the substrate to be labeled and/or from a second dye (e.g., fluorescent dye) associated with the substrate and/or associated with the linker. A ring can be a component of an amino acid (e.g., a non-proteinogenic amino acid, as described herein).

In some cases, a linker may be "fully rigid" (e.g., substantially inflexible). For example, ring systems of the linker may not be separated by any $sp^2$ or $sp^3$ carbon atoms. In general, $sp^2$ and $sp^3$ carbon atoms (e.g., between ring systems) provide the linker with a degree of physical flexibility. $sp^3$ carbon atoms in particular can confer significant flexibility. Without limitation, flexibility can allow a polymerase to accept a substrate (e.g., a nucleotide or nucleotide analog) modified with the linker and the dye (e.g., fluorescent dye), or otherwise improve the performance of a labeled system. However, in a multiple dye system (e.g., a system comprising multiple fluorescent labeling reagents, such as a polynucleotide including two or more nucleotides coupled to two or more fluorescent labeling reagents), an overly flexible linker may defeat the feature of rigidity and allow two dyes (e.g., fluorescent dyes) to come into close association and be quenched. Accordingly, ring systems of a linker may be connected to each other by a limited number of $sp^3$ bonds, such as by no more than two $sp^3$ bonds (e.g., 0, 1, or 2 $sp^3$ bonds). For example, at least two ring systems of a linker may be connected to each other by no more than two $sp^3$ bonds (e.g., by 0, 1, or 2 $sp^3$ bonds). For example, at least two ring systems of a linker may be connected to each other by a no more than two $sp^2$ bonds, such as by no more than 1 $sp^2$ bond. Ring systems of a linker may be connected to each other by a limited number of atoms, such as by no more than 2 atoms. For example, at least two ring systems of a linker may be connected to each other by no more than 2 atoms, such as by only 1 atom or by no atoms (e.g., directly connected).

The series of ring systems of a linker may comprise aromatic and/or aliphatic rings. At least two ring systems of a linker may be connected to each other directly without an intervening carbon atom. A linker may comprise at least one amino acid that may comprise a ring system. For example, a linker may comprise at least one non-proteinogenic amino acid (e.g., as described herein), such as a hydroxyproline.

Many applications of optical (e.g., fluorescent) labeling reagents (e.g., nucleic acid sequencing reactions) can be performed in aqueous solutions. In some cases, a linker that has too high of a proportion of carbon and hydrogen atoms and/or a lack of charged chemical groups can be insufficiently water-soluble to be useful in an aqueous solution. Therefore, the linkers described herein can have a water-soluble group or groups.

A linker may include a water-soluble group at any useful position. For example, a linker may comprise a water-soluble group at or near a point of attachment to a label (e.g., dye, as described herein). Alternatively or in addition to, a linker may comprise a water-soluble group at or near a point of attachment to a substrate (e.g., a protein or a nucleotide or nucleotide analog). Alternatively or in addition to, a linker may comprise a water-soluble group between points of attachment to a label (e.g., dye, as described herein) and a substrate (e.g., a protein or a nucleotide or nucleotide analog). One or more rings of a linker may comprise a water-soluble group. For example, each of the rings may comprise a water-soluble group, two or more rings may comprise a water-soluble group, only one of the rings may comprise a water-soluble group, or anywhere there between. A given ring may comprise one or more water-soluble moieties. For example, a ring of a linker may comprise two water-soluble moieties. The water-soluble group(s) can be a constituent part of the backbone of a ring of a linker or can be appended to a ring of a linker (e.g., as a substituent). Each water-soluble moiety of a linker may be different. Alternatively, one or more water-soluble moieties of a linker may be the same. For example, each water-soluble moiety of a linker may be the same. In some cases, the water-soluble group is positively charged. Examples of suitable water-soluble groups include, but are not limited to, a pyridinium, an imidazolium, a quaternary ammonium group, a sulfonate, a phosphate, an alcohol, an amine, an imine, a nitrile, an amide, a thiol, a carboxylic acid, a polyether, an aldehyde, and a boronic acid or boronic ester.

A water-soluble group can be any functional group that decreases (including making more negative) the log P of the optical (e.g., fluorescent) labeling reagent. Log P is the partition coefficient for a molecule between water and n-octanol. A greasy molecule is more likely to partition into octanol, giving a positive and large log P value. A formula for Log P can be represented as log $P_{octanol/water}$=log ([solute]$_{octanol}$/[solute]$_{water}$), where [solute]$_{octanol}$ is the concentration of the solute (i.e., the labeling reagent) in octanol and [solute]$_{water}$ is the concentration of the solute in water. Therefore, the more a compound partitions into water compared to octanol, the more negative the log P. Log P can be measured experimentally or predicted using software algorithms. The water-soluble group can have any suitable Log P value. In some cases, the Log P is less than about 2, less than about 1.5, less than about 1, less than about 0.5, less than about 0, less than about −0.5, less than about −1, less than about −1.5, less than about −2, or lower. In some cases, the Log P is between about 2.0 and about −2.0.

A linker may include one or more asymmetric (e.g., chiral) centers (e.g., as described herein). All stereochemical isomers of linkers are contemplated, including racemates and enantiomerically pure linkers.

A linker, and/or a substrate (e.g., protein or nucleotide or nucleotide analog) or dye to which it may be attached, may include one or more isotopic (e.g., radio) labels (e.g., as described herein). All isotopic variations of linkers are contemplated.

The structural features of a linker, including the number of rings, the rigidity of the linker, and the like, can combine to establish a functional distance between a dye (e.g., fluorescent) dye and a substrate (e.g., protein or nucleotide or nucleotide analog) that are linked by the linker. In some cases, the distance corresponds to the length (and/or the functional length) of the linker. In some cases, the functional length varies based on the temperature, solvent, pH, and/or salt concentration of the solution in which the length is measured or estimated. The functional length can be measured in a solution in which an optical (e.g., fluorescent) signal from the substrate is measured. The functional length may an average or ensemble value of a distribution of functional lengths (e.g., over rotational, vibrational, and translational motions) and may differ based on, e.g., temperature, solvent, pH, and/or salt concentrations. The functional length may be estimated (e.g., based on bond lengths and steric considerations, such as by use of a chemical drawing or modeling program) and/or measured (e.g., using molecular imaging and/or crystallographic techniques).

A linker can establish any suitable functional length between a dye (e.g., fluorescent dye) and a substrate (e.g., protein or nucleotide or nucleotide analog). In some cases, the functional length is at most about 500 nanometers (nm), about 200 nm, about 100 nm, about 75 nm, about 50 nm, about 40 nm, about 30 nm, about 20 nm, about 10 nm, about 5 nm, about 2 nm, about 1.0 nm, about 0.5 nm, about 0.3 nm, about 0.2 nm, or less. In some instances, the functional length is at least about 0.2 nanometers (nm), at least about 0.3 nm, at least about 0.5 nm, at least about 1.0 nm, at least about 2 nm, at least about 5 nm, at least about 10 nm, at least about 20 nm, at least about 30 nm, at least about 40 nm, at least about 50 nm, at least about 75 nm, at least about 100 nm, at least about 200 nm, at least about 500 nm, or more. In some instances, the functional length is between about 0.5 nm and about 50 nm.

In some cases, the linker forms a straight and/or contiguous chain. In some instances, the linker is branched. The linker can be capable of forming a bond with a plurality of dyes (e.g., fluorescent dyes) and/or substrates (e.g., nucleotides and/or nucleotide analogs).

A linker may be a polymer having a regularly repeating unit. Alternatively, a linker may be a co-polymer without a regularly repeating unit. In some cases, the linker is not the result of a polymerization process. In general, a polymerization process can generate products having a variety of degrees of polymerization and molecular weights. In contrast, in some cases, the linkers described herein have a defined (i.e., known) molecular weight.

A linker may be constructed from one or more amino acids. For example, a linker may be constructed from two or more amino acids. An amino acid may be a natural amino acid or a non-natural amino acid. An amino acid may be a proteinogenic amino acid or a non-proteinogenic amino acid. A "proteinogenic amino acid," as used herein, generally refers to a genetically encoded amino acid that may be incorporated into a protein during translation. Proteinogenic amino acids include arginine, histidine, lysine, aspartic acid, glutamic acid, serine, threonine, asparagine, glutamine, cysteine, selenocysteine, glycine, proline, alanine, isoleucine, leucine, methionine, phenylalanine, tryptophan, tyrosine, valine, selenocysteine, and pyrrolysine. A "non-proteinogenic amino acid," as used herein, is an amino acid that is not a proteinogenic amino acid. A non-proteinogenic amino acid may be a naturally occurring amino acid or a non-naturally occurring amino acid. Non-proteinogenic amino acids include amino acids that are not found in proteins and/or are not naturally encoded or found in the genetic code of an organism. Examples of non-proteinogenic amino acids include, but are not limited to, hydroxyproline, selenomethionine, hypusine, 2-aminoisobutyric acid, ay-aminobutyric acid, ornithine, citrulline, β-alanine (3-aminopropanoic acid), δ-aminolevulinic acid, 4-aminobenzoic acid, dehydroalanine, carboxyglutamic acid, pyroglutamic acid, norvaline, norleucine, alloisoleucine, t-leucine, pipecolic acid, allothreonine, homocysteine, homoserine, α-amino-n-heptanoic acid, α,β-diaminopropionic acid, α,γ-diaminobutyric acid, β-amino-n-butyric acid, β-aminoisobutyric acid, isovaline, sarcosine, N-ethyl glycine, N-propyl glycine, N-isopropyl glycine, N-methyl alanine, N-ethyl alanine, N-methyl β-alanine, N-ethyl β-alanine, isoserine, and α-hydroxy-γ-aminobutyric acid. Additional examples of non-proteinogenic amino acids include the non-natural amino acids described herein. A non-proteinogenic amino acid may comprise a ring structure. For example, a non-proteinogenic amino acid may be trans-4-aminomethylcyclohexane carboxylic acid or 4-hydrazinobenzoic acid. Such compounds may be FMOC-protected with FMOC (fluorenylmethyloxycarbohyl chloride) and utilized in solid-phase peptide synthesis. The structures of these compounds are shown below:

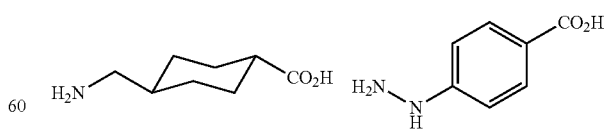

Where a linker comprises multiple amino acids, such as multiple non-proteinogenic amino acids, an amine moiety adjacent to a ring moiety (e.g., the amine moiety in the hydrazine moiety) can function as a water-solubilizing group. To synthesize a water-soluble peptide, a hybrid linker can be made that comprises alternating non-water-soluble amino acids and water-soluble amino acids (e.g., hydroxyproline). Other moieties can be used to increase water-solubility. For example, linking amino acids with oxamate moieties can provide water-solubility through the additional hydrogen bonding without adding any sp$^3$ linkages. The structure of the oxamate precursor 2-amino-2-oxoacetic acid is shown below:

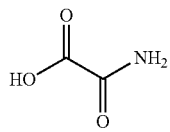

In some cases, a component (e.g., a monomer unit) of a linker may have an amino group, a carboxy group, and a water-solubilizing moiety. In some cases, a monomer may be deconstructed as two "half-monomers." That is, by using two different units, one that contains two amino groups and another that contains two carboxy groups, an amino acid moiety can be constructed, which amino acid moiety may be a unit (e.g., a repeated unit) of a linker. One or both units may include one or more water solubilizing moieties. For example, at least one unit may include a water-soluble group (e.g., as described herein). For example, 2,5-diaminohydroquinone can be one half-monomer (A), and 2,5-dihydroxy-terephthalic acid may be the other half-monomer (B). Such a scheme is shown below:

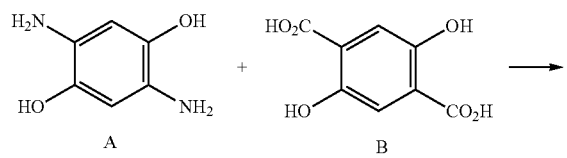

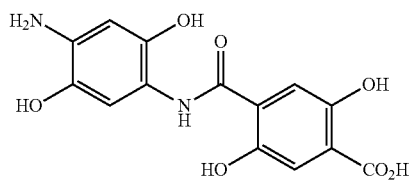

As shown above, A is a diamine and B is a diacid. Accordingly, non-proteinogenic (e.g., non-natural) amino acids may be constructed from diamines and diacids. An additional example of such a construction is shown below:

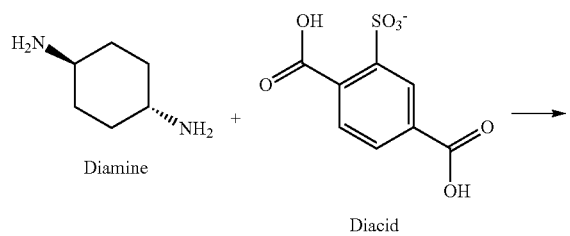

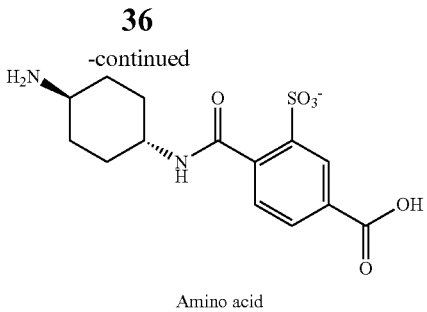

Amino acid

A polymer based on two half-monomers (e.g., as shown above) can be constructed via solid phase synthesis. Because the half-monomers can be homobifunctional in the linking moiety, in some cases no FMOC protection is required. For example, the dicarboxylic acid can be appended to the solid support, then an excess of the diamine added with appropriate coupling reagent (HBTU/HOBT/collidine). After washing away excess reagent, an excess of the dicarboxylic acid can be added with the coupling reagent. Side-products consisting of one molecule of the fluid phase reagent reacting with two solid-phase attached reagent can result in truncation of the synthesis. These side products can be separated from a product after cleavage from the support and purification by HPLC.

An advantage of the half-monomers approach can be increased flexibility in creating polymers. The diamine (A) can be replaced in a subsequent step by a different diamine (A') to change the properties of the polymer, in a repeating or non-repeating manner. Such a scheme may facilitate construction of a polymer such as ABA'BABA'B.

Additional examples of half-monomers for use according to the schemes described above include 2,5-diaminopyridine and 2,5-dicarboxypyridine, both of which are shown below, as well as the other moieties shown below:

Diamines

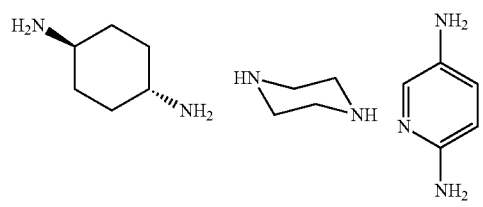

Dicarboxylic acids

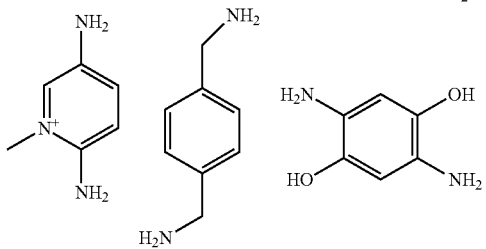

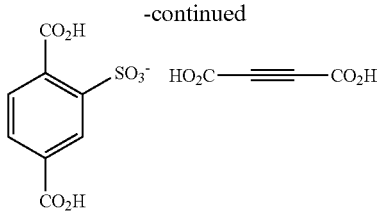
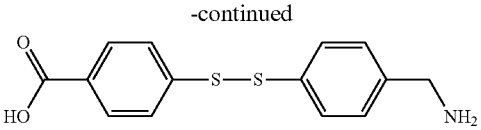

As described above, an amino acid (e.g., a non-proteinogenic amino acid that may be a non-natural amino acid) may be constructed from a diamine and a dicarboxylic acid. An amino acid (e.g., a non-proteinogenic amino acid that may be a non-natural amino acid) may also be constructed from an amino thiol and a thiol carboxylic acid. Examples of amino thiols and thiol carboxylic acids are shown below:

Amino thiols

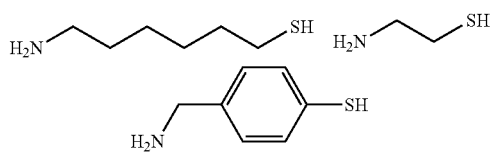

Thiol carboxylic acids

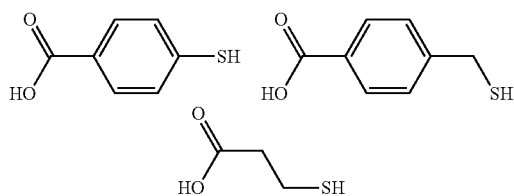

Examples of amino acids (e.g., non-natural amino acids) constructed from an amino thiol and a thiol carboxylic acid are shown below:

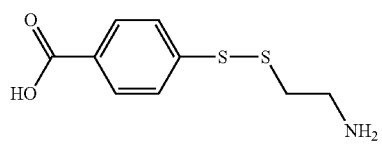

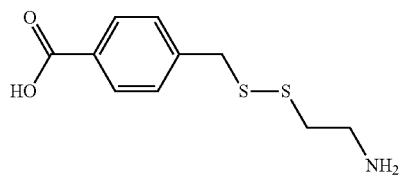

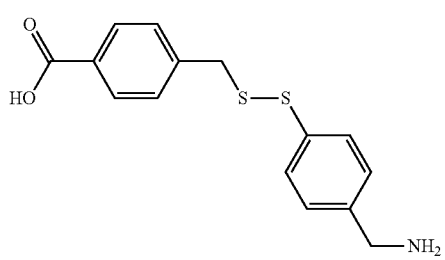

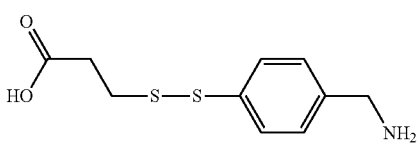

As shown above, amino acids constructed using an amino thiol and a thiol carboxylic acid may include a disulfide bond. As described elsewhere herein, a disulfide bond may be cleavable using a cleavage reagent (e.g., as described herein). Accordingly, an amino acid constructed from an amino thiol and a thiol carboxylic acid may serve as a cleavable portion of a linker. An amino acid constructed from an amino thiol and a carboxylic acid may be a component of a linker (e.g., as described herein) that may couple labeling moiety (e.g., a fluorescent dye) to a substrate (e.g., a nucleotide or nucleotide analog). The various structures allow different hydrophobicities for incorporation and may provide different "scar" moieties subsequent to interaction with a cleavage reagent (e.g., as described herein). Two or more amino acids, such as two or more amino acids constructed from an amino thiol and a thiol carboxylic acid, may be included in a linker. For example, two or more amino acids may be included in a linker and separated by no more than 2 $sp^3$ carbon atoms, such as by no more than 2 $sp^2$ carbon atoms or by no more than 2 atoms. Where two or more amino acids formed of amino thiols and thiol carboxylic acids are connected to one another within a linker, cleavage may be more rapid as there will be multiple possible sites for cleavage. An example of a portion of a linker including such a component is shown below:

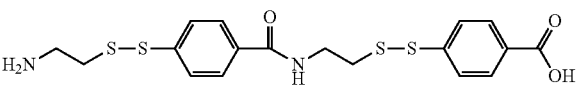 [SMILES: NCCSSc1ccc(C(=O)NCCSSc2ccc(C(=O)O)cc2)cc1]

As described above, two half-monomers may combine to provide an amino acid (e.g., a non-proteinogenic amino acid, such as a non-natural amino acid). Accordingly, a non-natural amino acid may include any known non-natural amino acid, as well as any non-natural amino acid that may be constructed as described herein.

Half-monomers such as those described herein can be constructed into polypeptide polymers. An example of a nucleotide constructed with two repeating units of an amino acid is shown below:

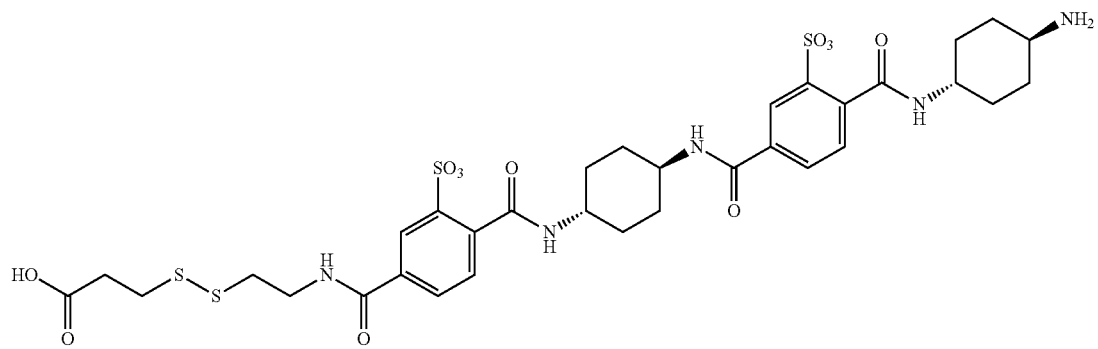

In some cases, before or after peptide coupling, the nitrogen in a nitrogen-containing ring can be quaternized to provide pyridinium moieties, thereby improving water-solubility of the final product. An example linker sequence generated in this manner is shown below:

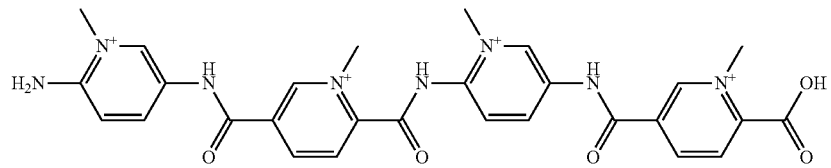

Water-solubilizing linkages that can work with the half-monomer method include, for example, those that have symmetrical functional groups, such as secondary amides, bishydrazides, and ureas. Examples of such moieties are shown below:

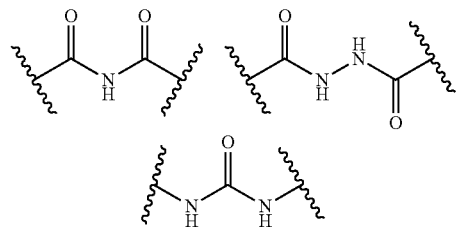

Amino acid linker subunits may be assembled into polymers by peptide synthesis methods. For example, a solid support method known as SPPS (Solid Phase Peptide Synthesis) or by liquid-phase synthesis may be used to assemble amino acids into a linker. SPPS methods can use a solid phase bead where the initial step is attachment of the C-terminal amino acid via its carboxylic acid moiety, leaving its free amine ready for coupling. Peptide synthesis can be initiated by flowing FMOC amine-protected monomers with peptide coupling reagents such as HBTU and an organic base. Excess reagent can be washed away and the next monomer is introduced. After one or more amino acids have been appended the final peptide can be cleaved from the beads and purified by HPLC. Liquid phase synthesis can use the same reagents (except the beads) but purification occurs after each step. The advantage of either stepwise polymerization process is that the resultant linkers can have a defined molecular weight that may be confirmed by mass spectrometry.

A linker may include one or more components. For example, a linker may include a first component that includes a polymeric region (e.g., that includes a repeating unit) and a second unit that does not include a polymeric region. The second component may include a cleavable component (e.g., as described herein). Examples of cleavable linkers include, but are not limited to, the structures E and B shown below:

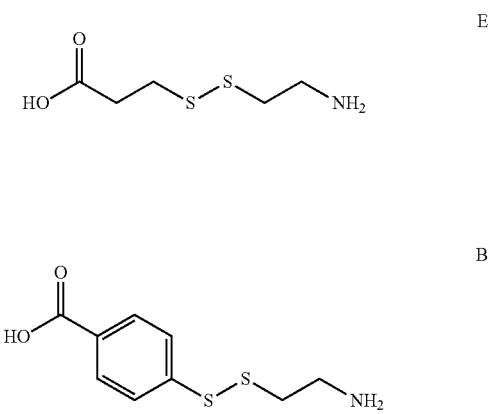

In the structures shown above, the disulfide moieties may be cleaved (e.g., as described herein) to provide thiol scars. The cleavable linkers may be attached to substrates upon reaction between a carboxyl moiety of the linker moiety and an amine moiety attached to a substrate (e.g., protein or nucleotide or nucleotide analog) to provide the substrate attached to the cleavable linker via an amide moiety. For example, the substrate may be a nucleotide or nucleotide analog including a propargylamino moiety, and a fluorescent labeling reagent comprising a dye and a linker described herein may be configured to associate with the substrate via the propargylamino moiety. Examples of such substrates are shown below:

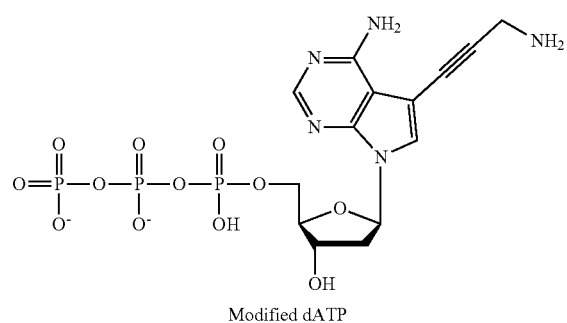

Modified dATP

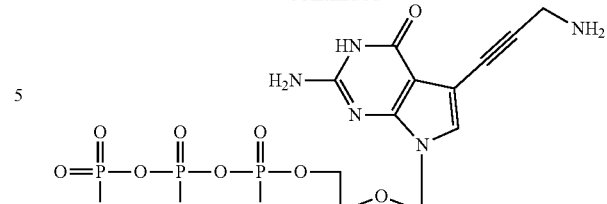

Modified dGTP

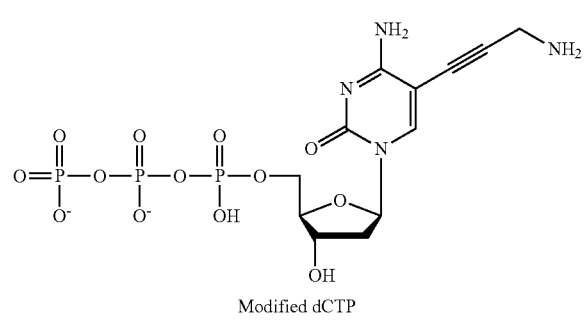

Modified dCTP

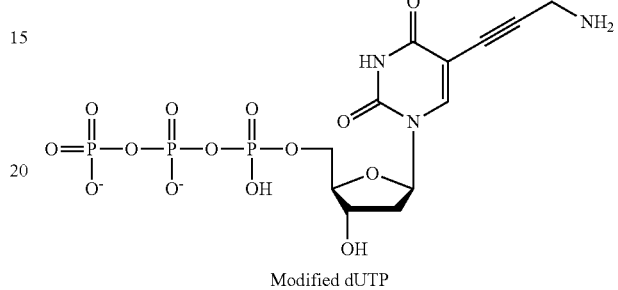

Modified dUTP

The first component of a linker including first and second components may include a repeating unit. For example, the linker may include a first component including one or more hydroxyproline moieties. An example of such a linker component is shown below:

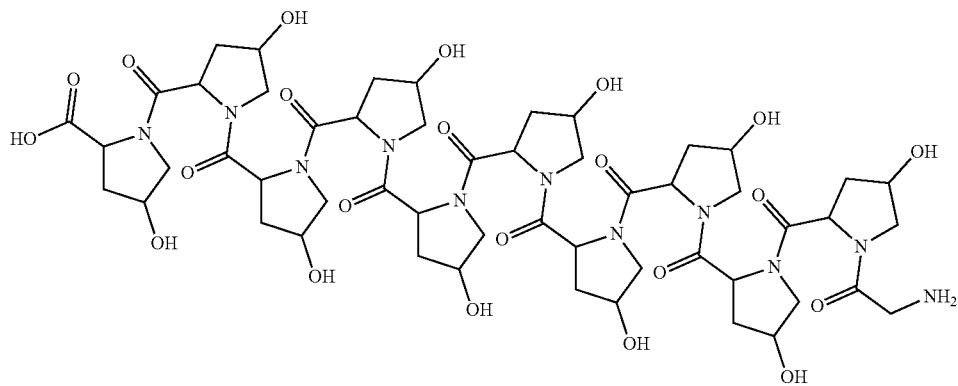

hyp10

The linker shown above includes 10 hydroxyproline moieties and a glycine moiety and is referred to herein as "H" or "hyp10". An alternate version of the linker above includes 20 hydroxyproline moieties and a glycine moiety and is referred to herein as "hyp20". As described herein, all stereoisomers of hyp10 and hyp20, as well as combinations thereof, are contemplated. A linker component such as hyp10 can be linked to a cleavable linker via reaction between a free carboxyl moiety of the linker component and an amino moiety of a cleavable linker. A linker component such as hyp10 can be linked to a dye via the free amino moiety of the linker component. Examples of optical labeling reagent including a first linker component including a repeating unit (e.g., hyp10) and a second linker component including a cleavable linker are provided elsewhere herein.

Linkers may provide linkages between fluorescent moieties (e.g., dyes, as described herein) and substrates (e.g., proteins or nucleotides or nucleotide analogs). For example, an optical (e.g., fluorescent) labeling reagent may comprise an optical dye (e.g., fluorescent dye) attached to a linker (e.g., as described herein). Non-limiting examples of dyes (e.g., fluorescent dyes) include SYBR green, SYBR blue, DAPI, propidium iodine, Hoechst, SYBR gold, ethidium bromide, acridine, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, propidium iodide, hexidium iodide, dihydroethidium, ethidium homodimer-1 and -2, ethidium monoazide, ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO dyes (e.g., SYTO-40, -41, -42, -43, -44, and -45 (blue); SYTO-13, -16, -24, -21, -23, -12, -11, -20, -22, -15, -14, and -25 (green); SYTO-81, -80, -82, -83, -84, and -85 (orange); SYTO-64, -17, -59, -61, -62, -60, and -63 (red)), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), VIC, 5- (or 6-) iodoacetamidofluorescein, 5-{[2(and 3)-5-(Acetyl-mercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor dyes (e.g., AlexaFluor 350, 405, 430, 488, 532, 546, 555, 568, 594, 610, 633, 635, 647, 660, 680, 700, 750, and 790 dyes), DyLight dyes (e.g., DyLight 350, 405, 488, 550, 594, 633, 650, 680, 755, and 800 dyes), Black Hole Quencher Dyes (Biosearch Technologies) (e.g., BH1-0, BHQ-1, BHQ-3, and BHQ-10), QSY Dye fluorescent quenchers (from Molecular Probes/Invitrogen)(e.g., QSY7, QSY9, QSY21, and QSY35), Dabcyl, Dabsyl. Cy5Q, Cy7Q, Dark Cyanine dyes (GE Healthcare), Dy-Quenchers (Dyomics) (e.g., DYQ-660 and DYQ-661), ATTO fluorescent quenchers (ATTO-TEC GmbH) (e.g., ATTO 540Q, 580Q, 612Q, 532, and 633), and other fluorophores and quenchers (e.g., as described herein). In some cases, the label may be a type that does not self-quench or exhibit proximity quenching. Non-limiting examples of a label type that does not self-quench or exhibit proximity quenching include Bimane derivatives such as Monobromobimane. Additional dyes included in structures provided herein may also be utilized in combination with any of the linkers provided herein, and with any substrate described herein, regardless of the context of their disclosure.

An optical (e.g., fluorescent) labeling reagent comprising an optical dye (e.g., fluorescent dye) and a linker can further comprise a cleavable group that is capable of being cleaved to separate the optical dye from a substrate with which the optical labeling reagent is associated. All or a portion of the linker may be part of the cleavable group. In some cases, cleaving a cleavable group may leave a scar group associated with substrate. The cleavable group can be, for example, an azidomethyl group capable of being cleaved by tris(2-carboxyethyl)phosphine (TCEP), dithiothreitol (DTT), or tetrahydropyranyl (THP) to leave a hydroxyl scar group. The cleavable group can be, for example, a disulfide bond capable of being cleaved by TCEP, DTT or THP to leave a thiol scar group. The cleavable group can be, for example, a hydrocarbyldithiomethyl group capable of being cleaved by TCEP, DTT or THP to leave a hydroxyl scar group. The cleavable group can be, for example, a 2-nitrobenzyloxy group capable of being cleaved by ultraviolet (UV) light to leave a hydroxyl scar group. A scar may also be, for example, an aromatic group such as a phenyl or benzyl moiety.

An optical (e.g., fluorescent) labeling reagent may be configured to associate with a substrate such as a nucleotide or nucleotide analog (e.g., as described herein). Alternatively or in addition to, an optical (e.g., fluorescent) labeling reagent may be configured to associate with a substrate such as a protein, cell, lipid, or antibody. For example, the optical labeling reagent may be configured to associate with a protein. A protein substrate may be any protein, and may include any useful modification, mutation, or label, including any isotopic label. For example, a protein may be an antibody such as a monoclonal antibody. A protein associated with one or more optical (e.g., fluorescent) labeling reagents (e.g., as described herein) may be, for example, an antibody (e.g., a monoclonal antibody) useful for labeling a cell, which labeled cell may be analyzed and sorted using flow cytometry.

An optical (e.g., fluorescent) labeling reagent (e.g., as described herein) can decrease quenching (e.g., between dyes coupled to nucleotides or nucleotide analogs incorporated into a growing nucleic acid strand, such as during nucleic acid sequencing). For example, an optical (e.g., fluorescent) signal emitted by a substrate (e.g., a nucleotide or nucleotide analog that may be incorporated into a growing nucleic acid strand) can be proportional to the number of optical (e.g., fluorescent) labels associated with the substrate (e.g., to the number of optical labels incorporated adjacent or in proximity to the substrate). For example, multiple optical labeling reagents including substrates of the same or different types (e.g., nucleotides or nucleotide analogs of a same or different type) may be incorporated in proximity to one another in a growing nucleic acid strand (e.g., during nucleic acid sequencing). In such a system, signal emitted by the collective substrates may be approximately proportional (e.g., linearly proportional) to the number of dye-labeled substrates incorporated. In other words, quenching may not significantly impact the signal emitted. This may be observable in a system in which 100% labeling fractions are used. Where less than 100% of substrates are labeled (e.g., less than 100% of nucleotides in a nucleotide flow are labeled), an optical (e.g., fluorescent) signal emitted by substrates (e.g., nucleotides or nucleotide analogs) incorporated into a plurality of growing nucleic acid strands (e.g., a plurality of growing nucleic acid strands coupled to sequencing templates coupled to a support, as described herein) may be proportional to the length of a homopolymer region of the growing nucleic acid strands. Similarly, where less than 100% of substrates are labeled (e.g., less than 100% of nucleotides in each of successive nucleotide flows are labeled), an optical (e.g., fluorescent) signal emitted by substrates (e.g., nucleotides or nucleotide analogs) incorporated into a plurality of growing nucleic acid strands (e.g., a plurality of growing nucleic acid strands coupled to sequencing templates coupled to a support, as described herein) may be proportional to the length of a heteropolymeric and/or homopolymer region of the growing nucleic acid strands. In some such cases, the intensity of a measured optical (e.g., fluorescent) signal may be linearly proportional to the length of a heteropolymeric and/or homopolymeric region into which substrates have incorporated. For example, a measured optical (e.g., fluorescent) signal may be linearly proportional with a slope of approximately 1.0 when optical (e.g., fluorescent) signal is plotted against the length in substrates of a heteropolymeric and/or homopolymeric region into which substrates have incorporated.

An optical (e.g., fluorescent) labeling reagent (e.g., as described herein) can decrease quenching in a protein system. When labeling proteins, quenching may start to happen at a fluorophore to protein ratio (F/P) of around 3. Using optical labeling reagents provided herein, higher F/P ratios, and thus brighter reagents, may be obtained. This may be useful for analyzing proteins (e.g., using imaging) and/or for analyzing cells labeled with proteins (e.g., antibodies) associated with one or more optical (e.g., fluorescent) labeling reagents.

Figure 1C:
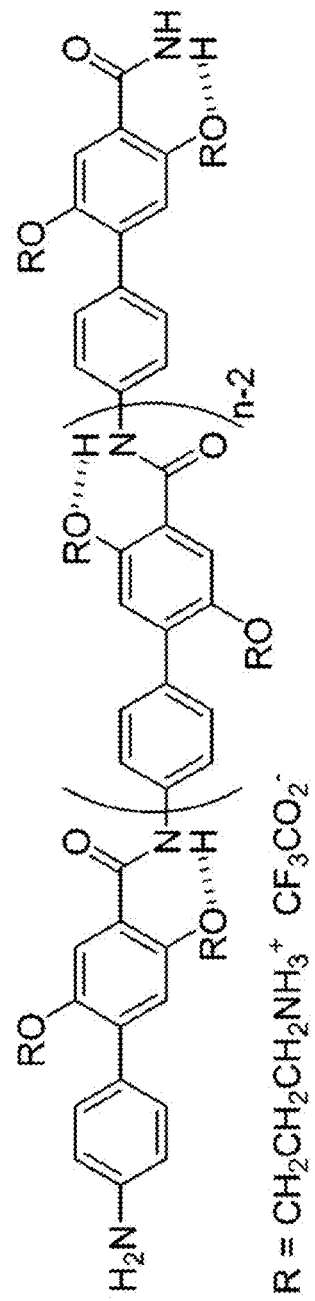
FIG. 1C shows an example of a linker of the present disclosure, where R is a water solubilizing group.

Examples of the linkers described herein are found, e.g., in FIGS. 1A-1C, 2A, 4, 5A, 5B, 6, 7, 8, 13A-13C, 14A, 14B, 16, and 17. In some cases, the R group included in these linkers (e.g., as in FIG. 1C) confers sufficient water solubility on the labeling reagent. Additional examples are included elsewhere herein, including in the Examples below.

In as aspect, the present disclosure provides an oligonucleotide molecule comprising a fluorescent labeling reagent or derivative thereof (e.g., as described herein). The oligonucleotide molecule may comprise one or more additional fluorescent labeling reagents of a same type (e.g., comprising linkers having the same chemical structure, dyes comprising the same chemical structure, and/or associated with substrates (e.g., nucleotides) of a same type). The fluorescent labeling reagent and one or more additional fluorescent labeling reagents of the oligonucleotide molecule may be associated with nucleotides. For example, the fluorescent labeling reagents may be connected to nucleobases of nucleotides of the oligonucleotide molecule. A fluorescent labeling reagent and one or more additional fluorescent labeling reagent may be connected to adjacent nucleotides of the oligonucleotide molecule. Alternatively or in addition to, the fluorescent labeling reagent and the one or more additional fluorescent labeling reagents may be connected to nucleotides of the oligonucleotide molecule that are separated by one or more nucleotides that are not connected to fluorescent labeling reagents. The oligonucleotide molecule may be a single-stranded molecule. Alternatively, the oligonucleotide molecule may be a double-stranded or partially double-stranded molecule. A double-stranded or partially double-stranded molecule may comprise fluorescent labeling reagents associated with a single strand or both strands. The oligonucleotide molecule may be a deoxyribonucleic acid molecule. The oligonucleotide molecule may a ribonucleic acid molecule. The oligonucleotide molecule may be generated and/or modified via a nucleic acid sequencing process (e.g., as described herein).

The linker of the fluorescent labeling reagent may comprise a cleavable group that is configured to be cleaved to separate the fluorescent dye of the fluorescent labeling reagent from a substrate (e.g., nucleotide) with which it is associated. For example, the linker may comprise a cleavable group comprising an azidomethyl group, a disulfide bond, a hydrocarbyldithiomethyl group, or a 2-nitrobenzyloxy group. The cleavable group may be configured to be cleaved by application of one or more members of the group consisting of tris(2-carboxyethyl)phosphine (TCEP), dithiothreitol (DTT), tetrahydropyranyl (THP), ultraviolet (UV) light, and a combination thereof. The oligonucleotide molecule comprising a fluorescent labeling reagent may be configured to emit a fluorescent signal (e.g., upon excitation at an appropriate range of energy, as described herein).

In another aspect, the present disclosure provides a kit comprising a plurality of linkers (e.g., as described herein). A linker of the plurality of linkers may comprise (i) one or more water soluble groups and (ii) two or more ring systems. At least two of the two or more ring systems may be connected to each other by no more than two sp$^3$ carbon atoms. For example, at least two of the two or more ring systems may be connected to each other by an sp$^2$ carbon atom. At least two of the two or more ring systems may be connected to each other by no more than two atoms. The linker may comprise a non-proteinogenic amino acid (e.g., as described herein) comprising a ring system of the two or more ring systems. For example, the linker may comprise a hydroxyproline or an amino acid constructed from, e.g., a diamine and a dicarboxylic acid or an amino thiol and a thiol carboxylic acid. The linker may be connected to a fluorescent dye (e.g., as described herein) and/or associated with a substrate. For example, the linker may be connected to a fluorescent dye and coupled to a substrate selected from a nucleotide, a protein, a lipid, a cell, and an antibody. For example, the linker may be connected to a fluorescent dye and a nucleotide.

The linker may comprise a plurality of amino acids, such as a plurality of non-proteinogenic (e.g., non-natural) amino acids. For example, the linker may comprise a plurality of hydroxyprolines (e.g., a hyp10 moiety). At least one water-soluble group of the one or more water-soluble groups may be appended to a ring structure of the two or more ring systems. The one or more water soluble groups may be selected from the group consisting of a pyridinium, an imidazolium, a quaternary ammonium group, a sulfonate, a phosphate, an alcohol, an amine, an imine, a nitrile, an amide, a thiol, a carboxylic acid, a polyether, an aldehyde, a boronic acid, and a boronic ester. The linker may comprise a cleavable group that is configured to be cleaved to separate a first portion of the linker from a second portion of the linker. The cleavable group may be selected from the group consisting of an azidomethyl group, a disulfide bond, a hydrocarbyldithiomethyl group, and a 2-nitrobenzyloxy group. The cleavable group may be cleavable by application of one or more members of the group consisting of tris(2-carboxyethyl)phosphine (TCEP), dithiothreitol (DTT), tetrahydropyranyl (THP), ultraviolet (UV) light, and a combination thereof. The linker may comprise a moiety selected from the group consisting of

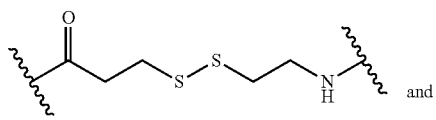 and

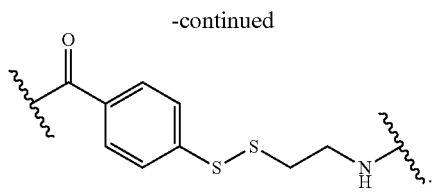

These moieties both comprise disulfide groups and so may be considered cleavable groups.

The plurality of linkers of the kit may comprise a first linker associated with a first substrate (e.g., a first nucleotide) and a second linker associated with a second substrate (e.g., a second nucleotide). The first substrate and the second substrate may be of different types (e.g., different canonical nucleotides). The first substrate and the second substrate may be nucleotides comprising nucleobases of different types (e.g., A, C, G, U, and T). The first linker and the second linker may comprise the same chemical structure. Similarly, the first linker may be connected to a first fluorescent dye and the second linker may be connected to a second fluorescent dye. The first fluorescent dye and the second fluorescent dye may be of different types. For example, the first and second fluorescent dyes may fluoresce at different wavelengths and/or have different maximum excitation wavelengths. The first and second fluorescent dyes may fluoresce at similar wavelengths and/or have similar maximum excitation wavelengths regardless of whether they share the same chemical structure.

The plurality of linkers of the kit may further comprise a third linker associated with a third substrate and a fourth linker associated with a fourth substrate. The first substrate, the second substrate, the third substrate, and the fourth substrate may be of different types. For example, the first substrate, the second substrate, the third substrate, and the fourth substrate may be nucleotides comprising nucleobases of different types (e.g., A, C, G, and U/T). The first linker and the third linker may comprise different chemical structures. The first and third linker may comprise a same chemical group, such as a same cleavable group (e.g., as described herein). For example, the first linker and the third linker may each comprise a moiety comprising a disulfide bond. Similarly, the first linker and the fourth linker may comprise different chemical structures. The first and fourth linker may comprise a same chemical group, such as a same cleavable group (e.g., as described herein). For example, the first linker and the fourth linker may each comprise a moiety comprising a disulfide bond.

In an example, the first linker comprises a hyp10 moiety and a first cleavable moiety, the second linker comprises a hyp10 moiety and a second cleavable moiety, the third linker comprises a third cleavable moiety and does not comprise a hyp10 moiety, and the fourth linker comprises a fourth cleavable moiety and does not comprise a hyp10 moiety. The second cleavable moiety may have a chemical structure that is different than the first cleavable moiety. Alternatively, the second cleavable moiety and the first cleavable moiety may have the same chemical structures. The third cleavable moiety and the fourth cleavable moiety may have the same chemical structure. Alternatively, the third cleavable moiety and the fourth cleavable moiety may have different chemical structures. In an example, the first linker and the second linker each have a first chemical structure and the third linker and the fourth linker each have a second chemical structure, which second structure is different than the first chemical structure. In another example, the first linker, the second linker, the third linker, and the fourth linker all have the same chemical structure. In another example, the first linker, the second linker, the third linker, and the fourth linker all have different chemical structures.

Methods for Using the Optical Labeling Reagents

There are several different types of quenching that can be reduced and different types of applications that can be performed using the optical (e.g., fluorescent) labeling reagents described herein.

The methods described herein can be used to reduce quenching, including G-quenching. Attachment of dyes (e.g., fluorescent dyes) to nucleotides (e.g., via a linker provided herein) can result in dye-quenching for many dyes, particularly when the dye is attached to a guanosine nucleotide. Dye quenching may take place between a dye and a nucleotide with which it is associated, as well as between dye moieties, such as between dye moieties coupled to different nucleotides (e.g., adjacent nucleotides or nucleotides separated by one or more other nucleotides). Use of the linkers provided herein can alleviate the quenching allowing more sensitive detection of sequences containing G. In addition, a dye-labeled nucleotide in proximity to a G-homopolymer region may show reduced fluorescence. Any nucleic acid sequencing method that requires attachment of a dye to dGTP may benefit from these linkers, including single molecule detection, sequencing using 3'-blocked nucleotides, and sequencing by hybridization.

The methods described herein can be used to reduce dye-dye quenching on adjacent or neighboring nucleotides (e.g., nucleotides separated by one, two, or more other nucleotides) on the same DNA strand. Methods that require dyes on adjacent or neighboring nucleotides can result in proximity quenching; that is, two dyes next to each other are less bright than twice the brightness of one dye, or often, less bright than even a single dye. Use of the linkers provided herein may alleviate the quenching, allowing quantitative detection of multiple dyes. For example, in sequencing methods such as mostly natural nucleotide flow sequencing, the fraction of labeled dye is typically less than 5%, since homopolymers are not linear in signal to homopolymer length at higher fractions due to the quenching problem. The reagents described herein can allow more (e.g., more than 5%, in some cases up to 100%) of the nucleotides to be labeled while facilitating sensitive and accurate detection of incorporated nucleotides.

The use of a dye-linker-nucleotide provided herein may result in more efficient incorporation into a growing nucleic acid strand (e.g., increased tolerance) by a polymerase (e.g., as described herein), compared to a dye-nucleotide lacking the linker (e.g., during nucleic acid sequencing). The result may be that a lower amount of the dye-labeled nucleotide is used to achieve the same signal.

The use of a dye-linker-nucleotide provided herein may result in less misincorporation by a polymerase (e.g., as described herein) (e.g., during nucleic acid sequencing). The result may be less loss of template strands, and thus longer sequencing reads.

The use of a dye-linker-nucleotide provided herein may result in less mispair extension (e.g., during nucleic acid sequencing), and thus reduced lead phasing.

The methods described herein can be used to reduce dye-dye quenching in multi-dye applications. Hybridization assays can also benefit from linkers that prevent quenching. Quenching effects may result in non-linearity of target to signal.

The methods described herein can be used in combination with oligomers and dendrimers for signal amplification.

Non-quenching linkers may allow the synthesis of very bright polymers for antibody labeling. These bright antibodies may be used for cell-surface labeling in flow cytometry or for antigen detection methods such as lateral flow tests and fluorescent immunoassays.

The optical (e.g., fluorescent) labeling reagent of the present disclosure may be used as a molecular ruler. The substrate can be a fluorescence quencher, a fluorescence donor, or a fluorescence acceptor. In some cases, the substrate is a nucleotide. The linker can be attached to the nucleotide on the nucleobase as shown below, where the dye is Atto633:

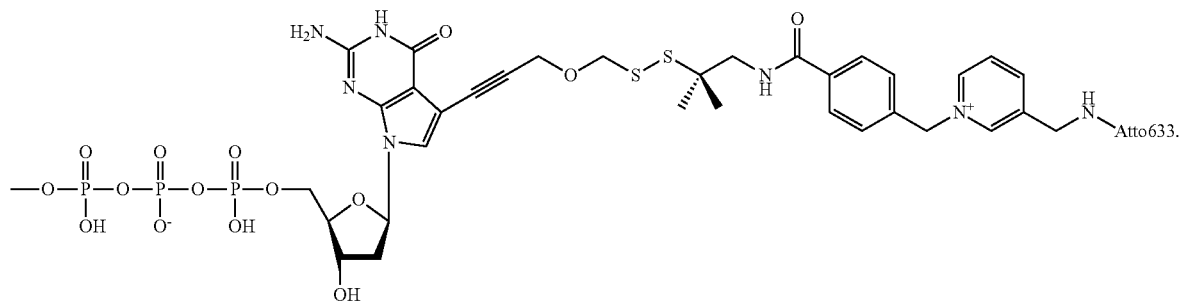

The structure shown above is an optical (e.g., fluorescent) labeling reagent comprising a cleavable (via the disulfide bond) moiety and a fluorescent dye attached via a pyridinium linker to a dGTP analog (dGTP-SS-py-Atto633). Additional examples of optical labeling reagents are provided throughout the disclosure.

The dye-labeled nucleotides described herein can be used in a sequencing by synthesis method using a mixture of dye-labeled and natural nucleotides in a flow-based scheme. Such methods often use a low percentage of labeled nucleotides compared to natural nucleotides. However, using a low percentage of labeled nucleotides compared to natural nucleotides in flow mixtures (e.g., less than 20%) can have multiple drawbacks: (a) since a small fraction of the template provides sequence information, the method requires a high template copy number; (b) variability in DNA polymerase extension rates between labeled and unlabeled nucleotides can result in context-dependent labeling fractions, thus increasing the difficulty of distinguishing a single base incorporation from multiple base incorporations; and (c) the low fraction of labeling moieties can result in high binomial noise in the populations of labeled product. Methods for flow-based sequencing using mostly natural nucleotides are further described in U.S. Pat. No. 8,772,473, which is incorporated herein by reference in its entirety for all purposes.

The semi-rigid linkers provided herein may allow a labeled fraction of dye-labeled nucleotide to natural nucleotide in each flow to be sufficiently high (e.g., 20-100% labeling) to avoid or reduce the effect of the aforementioned disadvantages of such schemes. This higher percentage labeling can result in greater optical (e.g., fluorescent) signal and thus a lower template requirement. If 100% labeling is used, the binomial noise and context variation may be essentially eliminated. The key technical barrier overcome by the solution described herein is that the dye-labeled nucleotides on adjacent or nearby nucleotides must show minimal quenching. The overall result of the combined advantages may be more accurate DNA sequencing.

The present disclosure provides a method for sequencing a nucleic acid molecule. The method can comprise contacting the nucleic acid molecule with a primer under conditions sufficient to hybridize the primer to the nucleic acid molecule, thereby generating a sequencing template. The sequencing template may then be contacted with a polymerase (e.g., as described herein) and a solution (e.g., a nucleotide flow) comprising a plurality of optically (e.g., fluorescently) labeled nucleotides (e.g., as described herein). Each optically (e.g., fluorescently) labeled nucleotide of the plurality of optically (e.g., fluorescently) labeled nucleotides may comprise the same chemical structure (e.g., each labeled nucleotide may comprise a dye of a same type, a linker of a same type, and a nucleotide or nucleotide analog of a same type). An optically labeled nucleotide of the plurality of optically labeled nucleotides may be complementary to the nucleic acid molecule at a plurality of positions adjacent to the primer hybridized to the nucleic acid molecule. Accordingly, one or more optically labeled nucleotides of the plurality of optically labeled nucleotides may be incorporated into the sequencing template. Where the nucleic acid molecule includes a homopolymeric region, multiple nucleotides (e.g., labeled and unlabeled nucleotides) may be incorporated. Incorporation of multiple nucleotides adjacent to one another may be facilitated by the use of non-terminated nucleotides. The solution comprising the plurality of optically labeled nucleotides may then be washed away from the sequencing template (e.g., using a wash flow, as described herein). An optical (e.g., fluorescent) signal from the sequencing template may be measured. Where two or more labeled nucleotides are incorporated into a homopolymeric region, the intensity of the measured optical (e.g., fluorescent) signal may be greater than an optical (e.g., fluorescent) signal that may be measured if a single optically (e.g., fluorescently) labeled nucleotide of the plurality of optically (e.g., fluorescently) labeled nucleotides had been incorporated into the sequencing template. Such a method may be particularly useful for sequencing of homopolymers or portions of nucleic acids that are homopolymeric (i.e., have a plurality of the same base in a row). An optically labeled nucleotide of the plurality of optically labeled nucleotides may comprise a dye (e.g., fluorescent dye) and a linker connected to the dye and a nucleotide (e.g., as described herein). The linker may comprise (i) one or more water soluble groups and (ii) two or more ring systems, wherein at least two of the two or more ring systems are connected to each other by no more than two $sp^3$ carbon atoms, such as by no more than two atoms. The linker may comprise a non-proteinogenic amino acid comprising a ring system of the two or more ring systems. For example, the linker may comprise a hydroxyproline or an amino acid constructed from, e.g., a diamine and a dicarboxylic acid or an amino thiol and a thiol carboxylic acid. The linker may be configured to establish a functional length between the dye and the nucleotide of at least about 0.5 nanometers.

The intensity of the measured optical (e.g., fluorescent) signal may be proportional to the number of optically (e.g., fluorescently) labeled nucleotides incorporated into the sequencing template (e.g., where 100% labeling fraction is used). In other words, quenching may not significantly impact the signal emitted. For example, the intensity may be linearly proportional to the number of optically (e.g., fluorescently) labeled nucleotides incorporated into the sequencing template. The intensity of the measured optical (e.g., fluorescent) signal may be linearly proportional with a slope of approximately 1.0 when plotted against the number of optically (e.g., fluorescently) labeled nucleotides incorporated into the sequencing template. Where less than 100% of substrates are labeled (e.g., less than 100% of nucleotides in a nucleotide flow are labeled), an optical (e.g., fluorescent) signal emitted by substrates (e.g., nucleotides or nucleotide analogs) incorporated into a plurality of growing nucleic acid strands (e.g., a plurality of growing nucleic acid strands coupled to sequencing templates coupled to a support, as described herein) may be proportional to the length of a homopolymer region of the growing nucleic acid strands. Similarly, where less than 100% of substrates are labeled (e.g., less than 100% of nucleotides in each of successive nucleotide flows are labeled), an optical (e.g., fluorescent) signal emitted by substrates (e.g., nucleotides or nucleotide analogs) incorporated into a plurality of growing nucleic acid strands (e.g., a plurality of growing nucleic acid strands coupled to sequencing templates coupled to a support, as described herein) may be proportional to the length of a heteropolymeric and/or homopolymer region of the growing nucleic acid strands. In some such cases, the intensity of a measured optical (e.g., fluorescent) signal may be linearly proportional to the length of a heteropolymeric and/or homopolymeric region into which substrates have incorporated. For example, a measured optical (e.g., fluorescent) signal may be linearly proportional with a slope of approximately 1.0 when optical (e.g., fluorescent) signal is plotted against the length in substrates of a heteropolymeric and/or homopolymeric region into which substrates have incorporated The solution comprising the plurality of optically (e.g., fluorescently) labeled nucleotides may also contain un-labeled nucleotides (e.g., the labeling fraction may be less than 100%). For example, at least about 20% of nucleotides in the solution may be optically labeled, and at least about 80% of nucleotides in the solution may not be optically labeled. In some cases, the majority of the nucleotides in the solution may be optically labeled (e.g., between about 50-100%).

In some cases, two or more optically (e.g., fluorescently) labeled nucleotides of the plurality of optically (e.g., fluorescently) labeled nucleotides are incorporated into the sequencing template (e.g., into a homopolymeric region). In some cases, three or more optically (e.g., fluorescently) labeled nucleotides of the plurality of optically (e.g., fluorescently) labeled nucleotides are incorporated into the sequencing template. The number of optically labeled nucleotides incorporated into the sequencing template during a given nucleotide flow may depend on the homopolymeric nature of the nucleic acid molecule. In some cases, a first optically (e.g., fluorescently) labeled nucleotide of the plurality of optically (e.g., fluorescently) labeled nucleotides is incorporated within four positions of a second optically (e.g., fluorescently) labeled nucleotide of the plurality of optically (e.g., fluorescently) labeled nucleotides.

An optically (e.g., fluorescently) labeled nucleotide may comprise a cleavable group to facilitate cleavage of the optical (e.g., fluorescent) label (e.g., as described herein). In some cases, a method may further comprise, subsequent to incorporation of the one or more optically (e.g., fluorescently) labeled nucleotides and washing away of residual solution, cleaving optical (e.g., fluorescent) labels of the one or more optically (e.g., fluorescently) labeled nucleotides incorporated into the sequencing template (e.g., as described herein). The cleavage flow may be followed by an additional wash flow.

In some cases, a nucleotide flow and wash flow may be followed by a "chase" flow comprising unlabeled nucleotides and no labeled nucleotides. The chase flow may be used to complete the sequencing reaction for a given nucleotide position or positions of the sequencing template (e.g., across a plurality of such templates immobilized to a support). The chase flow may precede detection of an optical signal from a template. Alternatively, the chase flow may follow detection of an optical signal from a template. The chase flow may precede a cleavage flow. Alternatively, the chase flow may follow a cleavage flow. The chase flow may be followed by a wash flow.

The methods provided herein can also be used to sequence heteropolymers and/or heteropolymeric regions of a nucleic acid molecule (i.e., portions that are not homopolymeric). Accordingly, the methods described herein can be used to sequence a nucleic acid molecule having any degree of heteropolymeric or homopolymeric nature.

Regarding homopolymers, a nucleotide flow at a homopolymer region may incorporate several nucleotides in a row. Contacting a sequencing template comprising a nucleic acid molecule (e.g., a nucleic acid molecule hybridized to an unextended primer) comprising a homopolymer region with a solution comprising a plurality of nucleotides (e.g., labeled and unlabeled nucleotides), where each nucleotide of the plurality of nucleotides is of a same type, may result in multiple nucleotides of the plurality of nucleotides being incorporated into the sequencing template. In some cases, at least 2, at least 3, at least 4, at least 5, at least 6, at least 7, at least 8, at least 9, or at least 10 nucleotides are incorporated (i.e., in a homopolymeric region of a nucleic acid molecule). The plurality of nucleotides incorporated into the sequencing template may comprise a plurality of labeled nucleotides (e.g., optically labeled, such as fluorescently labeled), as described herein. In such an instance, one or more of said nucleotides incorporated into a homopolymer region may be labeled, and may either occupy adjacent or non-adjacent positions to other labeled nucleotides incorporated into the homopolymeric region. The intensity of a signal obtained from a nucleic acid molecule may be proportional to the number of incorporated labeled nucleotides (e.g., where a labeling fraction of 100% is used). For example, the intensity of an optical signal (e.g., fluorescent signal) obtained from a nucleic acid molecule containing two labeled nucleotides may be of greater intensity than the optical signal obtained from a nucleic acid molecule containing one labeled nucleotide. Furthermore, the intensity of a signal obtained from a nucleic acid molecule may depend on the relative positioning of labeled nucleotides within a nucleic acid molecule. For example, a nucleic acid molecule containing two labeled nucleotides in non-adjacent positions may provide a different signal intensity than a nucleic acid molecule containing two labeled nucleotides in adjacent positions. Quenching in such systems may be optimized by careful selection of linkers and dyes (e.g., fluorescent dyes). In some cases, a plot of optical signal (e.g., fluorescence) vs. homopolymer length can be linear. For example, measured optical signal for an ensemble of growing nucleic acid strands including homopolymeric regions into which labeled nucleotides are incorporated may be approximately linearly proportional to the nucleotide length of the homopolymeric region.

In another aspect, the present disclosure provides a method for sequencing a nucleic acid molecule. The method can comprise contacting the nucleic acid molecule with a primer under conditions sufficient to hybridize the primer to the nucleic acid molecule, thereby generating a sequencing template. The may then be contacted with a polymerase and a first solution comprising a plurality of first optically (e.g., fluorescently) labeled nucleotides (and, optionally, a plurality of first unlabeled nucleotides). Each first optically (e.g., fluorescently) labeled nucleotide of the plurality of first optically (e.g., fluorescently) labeled nucleotides is of a same type. A first optically (e.g., fluorescently) labeled nucleotide of the plurality of first optically (e.g., fluorescently) labeled nucleotides may be complementary to the nucleic acid molecule to be sequenced at a position adjacent to the primer. A first optically (e.g., fluorescently) labeled nucleotide of the plurality of first optically (e.g., fluorescently) labeled nucleotides may thus be incorporated into the sequencing template to generate an extended primer. The first solution comprising the plurality of first optically (e.g., fluorescently) labeled nucleotides may then be washed away from the sequencing template (e.g., using a wash solution). A first optical (e.g., fluorescent) signal emitted by the sequencing template may then be measured (e.g., as described herein). The sequencing template may then be contacted with a polymerase and a second solution comprising a plurality of second optically (e.g., fluorescently) labeled nucleotides (and, optionally, a plurality of second unlabeled nucleotides). Each second optically (e.g., fluorescently) labeled nucleotide of the plurality of second optically (e.g., fluorescently) labeled nucleotides may be of a same type. A second optically (e.g., fluorescently) labeled nucleotide of the plurality of second optically (e.g., fluorescently) labeled nucleotides may be complementary to the nucleic acid molecule to be sequenced at a position adjacent to the extended primer. A second optically (e.g., fluorescently) labeled nucleotide of the plurality of second optically (e.g., fluorescently) labeled nucleotides may thus be incorporated into the sequencing template. The second solution comprising the plurality of second optically (e.g., fluorescently) labeled nucleotides may then be washed away from the sequencing template. A second optical (e.g., fluorescent) signal emitted by the sequencing template may then be measured. In some cases, the intensity of the second optical (e.g., fluorescent) signal may be greater than the intensity of the first optical (e.g., fluorescent) signal.

A first optically labeled nucleotide of the plurality of first optically labeled nucleotides may comprise a first dye (e.g., fluorescent dye) and a first linker connected to the first dye and a first nucleotide (e.g., as described herein). Similarly, a second optically labeled nucleotide of the plurality of second optically labeled nucleotides may comprise a second dye (e.g., fluorescent dye) and a second linker connected to the second dye and a second nucleotide (e.g., as described herein). The first linker may comprise (i) one or more water soluble groups and (ii) two or more ring systems, wherein at least two of the two or more ring systems are connected to each other by no more than two $sp^3$ carbon atoms, such as by no more than two atoms. For example, at least two of the two or more ring systems may be connected to each other by an $sp^2$ carbon atom. The linker may comprise a non-proteinogenic amino acid comprising a ring system of the two or more ring systems. For example, the first linker may comprise one or more hydroxyproline moieties (e.g., as described herein). The first linker may be configured to establish a functional length between the first dye and the first nucleotide of at least about 0.5 nanometers. Similarly, the second linker may comprise (i) one or more water soluble groups and (ii) two or more ring systems, wherein at least two of the two or more ring systems are connected to each other by no more than two $sp^3$ carbon atoms, such as by no more than two atoms. For example, at least two of the two or more ring systems may be connected to each other by an $sp^2$ carbon atom. The linker may comprise a non-proteinogenic amino acid comprising a ring system of the two or more ring systems. For example, the second linker may comprise one or more hydroxyproline moieties (e.g., as described herein). The second linker may be configured to establish a functional length between the second dye and the second nucleotide of at least about 0.5 nanometers. The first linker and the second linker may have the same structure. Alternatively, the first linker and the second linker may have different structures. The first linker and the second linker may comprise a shared structural motif, such as a shared cleavable component (e.g., as described herein). The first linker and/or the second linker may comprise a cleavable group configured to be cleaved with a cleavage reagent (e.g., as described herein).

The first solution comprising the plurality of first optically (e.g., fluorescently) labeled nucleotides may also contain first un-labeled nucleotides. For example, about 20% of the nucleotides of the first solution may be un-labeled. In some cases, at least 20% of the nucleotides of the first solution may be optically labeled, such as at least 50% or at least 80%. The un-labeled nucleotides may comprise the same nucleotide moiety (e.g., canonical nucleotide moiety) as the optically labeled nucleotides. Similarly, the second solution comprising the plurality of first optically labeled nucleotides may also contain second un-labeled nucleotides. For example, about 20% of the nucleotides of the second solution may be un-labeled. In some cases, at least 20% of the nucleotides of the second solution may be optically labeled, such as at least 50% or at least 80%. The un-labeled nucleotides may comprise the same nucleotide moiety (e.g., canonical nucleotide moiety) as the optically labeled nucleotides.

The plurality of first optically (e.g., fluorescently) labeled nucleotides may be different than the plurality of second optically (e.g., fluorescently) labeled nucleotides. For example, the plurality of first optically (e.g., fluorescently) labeled and the plurality of second optically (e.g., fluorescently) labeled nucleotides may comprise the same optical (e.g., fluorescent) label (e.g., the same dye) and different nucleotides. Alternatively, the plurality of first optically (e.g., fluorescently) labeled and the plurality of second optically (e.g., fluorescently) labeled nucleotides may comprise different optical (e.g., fluorescent) labels (e.g., different dyes) and the same nucleotides. In some cases, the plurality of first optically (e.g., fluorescently) labeled and the plurality of second optically (e.g., fluorescently) labeled nucleotides may comprise different optical (e.g., fluorescent) labels (e.g., different dyes) and different nucleotides. The first dye of the first plurality of optically labeled nucleotides and the second dye of the second plurality of optically labeled nucleotides may emit signal at approximately the same wavelength or range of wavelengths (e.g., whether the first and second dyes have the same or different chemical structures). For example, the first dye and the second dye may both emit signal in the green region of the visible portion of the electromagnetic spectrum.

In some cases, two or more first optically (e.g., fluorescently) labeled nucleotides may be incorporated into the sequencing template (e.g., in a homopolymeric region of the nucleic acid molecule). In some cases, two or more second optically (e.g., fluorescently) labeled nucleotides may be incorporated into the sequencing template.

Additional optically (e.g., fluorescently) labeled nucleotides may also be provided and incorporated into the sequencing template (e.g., in successive nucleotide flows, as described herein). For example, the method may further comprise contacting the sequencing template with a polymerase and a third solution comprising a plurality of third optically (e.g., fluorescently) labeled nucleotides, wherein each third optically (e.g., fluorescently) labeled nucleotide of the plurality of third optically (e.g., fluorescently) labeled nucleotides is of a same type, and wherein a third optically (e.g., fluorescently) labeled nucleotide of the plurality of third optically (e.g., fluorescently) labeled nucleotides is complementary to the nucleic acid molecule at a position adjacent to the further extended primer hybridized to the nucleic acid molecule, thereby incorporating a third optically (e.g., fluorescently) labeled nucleotide of the plurality of third optically (e.g., fluorescently) labeled nucleotides into the sequencing template; washing the third solution comprising the plurality of third optically (e.g., fluorescently) labeled nucleotides away from the sequencing template; and measuring a third optical (e.g., fluorescent) signal emitted by the sequencing template. In some cases, the intensity of the third optical signal may be greater than the intensity of the first optical (e.g., fluorescent) signal and the intensity of the second optical (e.g., fluorescent) signal. This process may be repeated with a fourth solution, etc. The third and fourth solutions may comprise optically (e.g., fluorescently) labeled nucleotides having different nucleotides than the first and second solutions, such that each canonical nucleotide (A, C, G, and U/T) may be provided in sequence to the sequencing template. A cycle in which each canonical nucleotide is provided to the sequencing template may be repeated one or more times to sequence and/or amplify the nucleic acid molecule.

A third optically labeled nucleotide of the plurality of third optically labeled nucleotides may comprise a third dye (e.g., fluorescent dye) and a third linker connected to the third dye and a third nucleotide (e.g., as described herein). The third linker may comprise (i) one or more water soluble groups and (ii) two or more ring systems, wherein at least two of the two or more ring systems are connected to each other by no more than two $sp^3$ carbon atoms, such as by no more than two atoms. For example, at least two of the two or more ring systems may be connected to each other by an $sp^2$ carbon atom. The linker may comprise a non-proteinogenic amino acid comprising a ring system of the two or more ring systems. For example, the third linker may comprise one or more hydroxyproline moieties (e.g., as described herein). The third linker may be configured to establish a functional length between the third dye and the third nucleotide of at least about 0.5 nanometers. The third linker and the first linker may have the same or different structures. Similarly, the third linker and the second linker may have the same or different structures. The third dye may have the same or a different structure as the first dye. Similarly, the third dye may have the same or a different structure as the second dye. The third dye and the first and/or second dye may emit at approximately the same wavelength or range of wavelengths (e.g., whether these dyes have the same or different chemical structures). Further, the third nucleotide may be of a same or different type as the first nucleotide, or the third nucleotide may be of a same or different type as the second nucleotide.

The method may further comprise, subsequent to washing a given solution (e.g., nucleotide flow) away (e.g., using a wash solution), cleaving the optical (e.g., fluorescent) label of its respective nucleotides. For example, after the first solution is washed away, the optical (e.g., fluorescent) label of the first optically (e.g., fluorescently) labeled nucleotide incorporated into the sequencing template may be cleaved (e.g., using a cleavage reagent to cleave a cleavable group of a linker of the first optically labeled nucleotide, as described herein). For example, the fluorescent dye(s) of the first optically labeled nucleotide(s) incorporated into the sequencing template may be cleaved prior to contacting the sequencing template with second optically labeled nucleotides (e.g., in a second nucleotide flow, as described herein). Accordingly, signal may be detected from one or more first optically labeled nucleotides prior to incorporation of one or more second optically labeled nucleotides into the sequencing template. Separation of the fluorescent dye (s) of the first optically labeled nucleotide(s) incorporated into the sequencing template may provide a scarred nucleotide(s) comprising a portion of the linker of the first optically labeled nucleotide, or a derivative thereof. Similarly, after the second solution (e.g., second nucleotide flow) is washed away, the optical (e.g., fluorescent) label of the second optically (e.g., fluorescently) labeled nucleotide incorporated into the sequencing template may be cleaved. All of a portion of the first and second linkers may be cleaved during the respective cleaving processes.

In another aspect, provided herein is a method for sequencing a nucleic acid molecule. The method can comprise providing a solution comprising a plurality of optically (e.g., fluorescently) labeled nucleotides, wherein each optically (e.g., fluorescently) labeled nucleotide of the plurality of optically (e.g., fluorescently) labeled nucleotides is of a same type. A given optically (e.g., fluorescently) labeled nucleotide of the plurality of fluorescently labeled nucleotides may comprise an optical (e.g., fluorescent) dye that is connected to a nucleotide via a semi-rigid water-soluble linker having a defined molecular weight. The linker connecting the dye and nucleotide may provide a functional length of at least about 0.5 nanometers (nm) between the dye and nucleotide. The nucleic acid molecule may then be contacted with a primer under conditions sufficient to hybridize the primer to a nucleic acid molecule to be sequenced to generate a sequencing template. The sequencing template may then be contacted with a polymerase and the solution containing the plurality of optically (e.g., fluorescently) labeled nucleotides, wherein an optically (e.g., fluorescently) labeled nucleotide of the plurality of optically (e.g., fluorescently) labeled nucleotides is complementary to the nucleic acid molecule to be sequenced at a position adjacent to the primer. One or more optically (e.g., fluorescently) labeled nucleotides of the plurality of optically (e.g., fluorescently) labeled nucleotides may thus be incorporated into the sequencing template. The solution comprising the plurality of optically (e.g., fluorescently) labeled nucleotides may be washed away from the sequencing template (e.g., using a wash solution). An optical (e.g., fluorescent) signal emitted by the sequencing template may then be measured.

The linker may comprise (i) one or more water soluble groups and (ii) two or more ring systems, wherein at least two of the two or more ring systems are connected to each other by no more than two $sp^3$ carbon atoms, such as by no more than two atoms (e.g., as described herein). For example, at least two of the two or more ring systems may be connected to each other by an $sp^2$ carbon atom. The linker may comprise a non-proteinogenic amino acid comprising a ring system of the two or more ring systems. For example, the linker may comprise one or more hydroxyproline moieties (e.g., as described herein). The linker may establish a functional length between the fluorescent dye and the nucleotide of at least about 0.5 nanometers (e.g., as described herein).

The measured optical (e.g., fluorescent) signal may be proportional to the number of optically (e.g., fluorescently) labeled nucleotides that were incorporated into the sequencing template. For example, where 100% labeling fraction is used (e.g., all nucleotides in the solution are labeled), quenching may not diminish the emitted signal. In such a system, the measured optical (e.g., fluorescent) signal can be linearly proportional to the number of optically (e.g., fluorescently) labeled nucleotides that were incorporated into the sequencing template. The measured optical (e.g., fluorescent) signal may be linearly proportional with a slope of approximately 1.0 when plotted against the number of optically (e.g., fluorescently) labeled nucleotides that were incorporated into the sequencing template. Where less than 100% of nucleotides are labeled (e.g., less than 100% of nucleotides in the solution are labeled), an optical (e.g., fluorescent) signal emitted by nucleotides incorporated into a plurality of growing nucleic acid strands (e.g., a plurality of growing nucleic acid strands coupled to sequencing templates coupled to a support, as described herein) may be proportional to the length of a homopolymer region of the growing nucleic acid strands. Similarly, where less than 100% of nucleotides are labeled, an optical (e.g., fluorescent) signal emitted by nucleotides incorporated into a plurality of growing nucleic acid strands (e.g., a plurality of growing nucleic acid strands coupled to sequencing templates coupled to a support, as described herein) may be proportional to the length of a heteropolymeric and/or homopolymer region of the growing nucleic acid strands. In some such cases, the intensity of a measured optical (e.g., fluorescent) signal may be linearly proportional to the length of a heteropolymeric and/or homopolymeric region into which nucleotides have incorporated. For example, a measured optical (e.g., fluorescent) signal may be linearly proportional with a slope of approximately 1.0 when optical (e.g., fluorescent) signal is plotted against the length in nucleotides of a heteropolymeric and/or homopolymeric region into which nucleotides have incorporated In some cases, the solution containing an optically (e.g., fluorescently) labeled nucleotide also contains un-labeled nucleotides. The un-labeled nucleotides may comprise the same nucleotide moiety (e.g., the same canonical nucleotide). In some embodiments, about 5%, about 10%, about 20%, about 30%, about 40%, about 50%, about 60%, about 70%, about 80%, about 90%, or about 100% of nucleotides in the solution are fluorescently labeled. In some cases, at least about 5%, at least about 10%, at least about 20%, at least about 30%, at least about 40%, at least about 50%, at least about 60%, at least about 70%, at least about 80%, at least about 90%, or more of nucleotides in the solution are fluorescently labeled. In some cases, at least about 5%, at least about 10%, at least about 20%, at least about 30%, at least about 40%, at least about 50%, at least about 60%, at least about 70%, at least about 80%, at least about 90%, or more of nucleotides in the solution are not fluorescently labeled.

A plurality of labeled nucleotides can be incorporated at locations along a nucleic acid molecule in proximity to each other. In some cases, a first optically (e.g., fluorescently) labeled nucleotide is incorporated within 4 positions, within 3 positions, within 2 positions, or next to a second optically (e.g., fluorescently) labeled nucleotide (e.g., a second optically labeled nucleotide of a same or different nucleotide type). In some cases, the method further comprises cleaving the optical (e.g., fluorescent) labels from the nucleotides after measuring the optical (e.g., fluorescent) signal (e.g., as described herein). Cleaving an optical (e.g., fluorescent) label may leave behind a scar (e.g., as described herein). A nucleic acid sequencing assay may be used to evaluate dye-labeled nucleotides. The assay may use a nucleic acid template having a known sequence, which sequence may include one or more homopolymeric regions. The template may be immobilized to a support (e.g., as described herein) via an adapter. A primer having a sequence at least partly complementary to the adapter or a portion thereof may hybridize to the adapter or portion thereof and provide a starting point for generation of a nucleic acid strand having a sequence complementary to that of the template via incorporation of labeled and unlabeled nucleotides (e.g., as described herein). The sequencing assay may use four distinct four nucleotide flows including different canonical nucleobases that may be repeated in cyclical fashion (e.g., cycle 1: A, G, C, U; cycle 2 A, G, C, U; etc.). Each nucleotide flow may include nucleotides including nucleobases of a single canonical type (or analogs thereof), some of which may be include optical labeling reagents provided herein. The labeling fraction (e.g., % of nucleotides included in the flow that are attached to an optical labeling reagent) may be varied between, e.g., 0.5% to 100%. Labeling fractions may be different for different nucleotide flows. Nucleotides may not be terminated to facilitate incorporation into homopolymeric regions. The template may be contacted with a nucleotide flow, followed by one or more wash flows (e.g., as described herein). The template may also be contacted with a cleavage flow (e.g., as described herein) including a cleavage reagent configured to cleave a portion of the optical labeling reagents attached to labeled nucleotides incorporated into the growing nucleic acid strand. A wash flow may be used to remove cleavage reagent and prepare the template for contact with a subsequent nucleotide flow. Emission may be detected from labeled nucleotides incorporated into the growing nucleic acid strand after each nucleotide flow.

Figure 18:
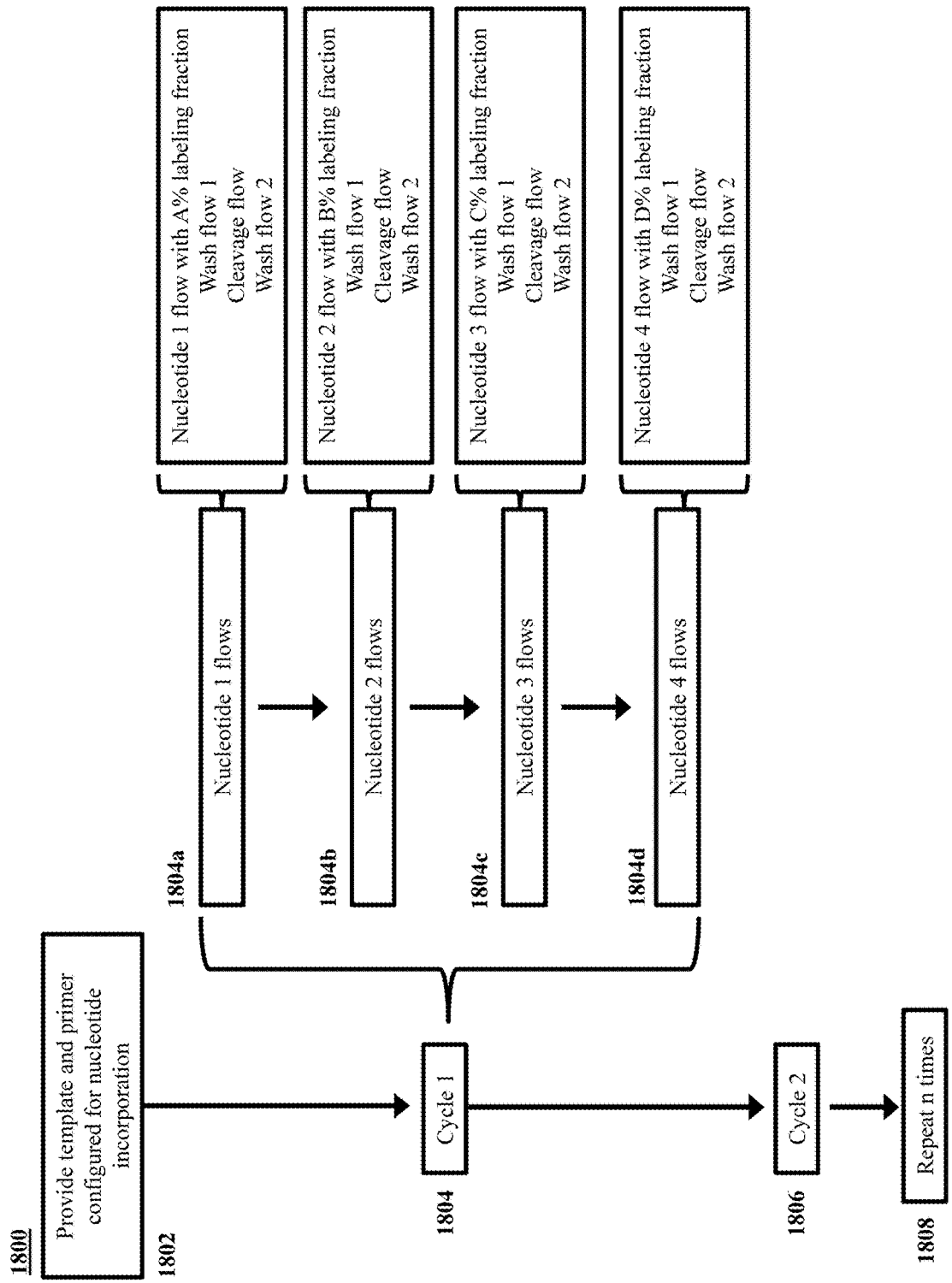
FIG. 18 shows an example sequencing procedure.

An example sequencing procedure 1800 is provided in FIG. 18. In process 1802, a template and primer configured for nucleotide incorporation are provided. A first sequencing cycle 1804 is subsequently performed. First sequencing cycle 1804 includes four flow processes 1804a, 1804b, 1804c, and 1804d, each of which multiple flows. Nucleotides 1, 2, 3, and 4 may each include nucleobases of different canonical types (e.g., A, G, C, and U). A given nucleotide flow may include both labeled nucleotides (e.g., nucleotides labeled with an optical labeling reagent provided herein) and unlabeled nucleotides. The labeling fraction of each nucleotide flow may be different. That is, A, B, C, and D in FIG. 18 may be the same or different and may range from 0% to 100% (e.g., as described herein). Labels and linkers used to label nucleotides 1, 2, 3, and 4 may be of the same or different types. For example, nucleotide 1 may have a linker including a cleavable linker and a hyp10 linker and a first green dye, and nucleotide 2 may have a linker including a cleavable linker but not a hyp10 linker and a second green dye. The first green dye may be the same as or different than the first green dye. The cleavable linkers associated with the different nucleotides may be the same or different. Flow process 1804a may include a nucleotide flow (e.g., a flow including a plurality of nucleotides of type Nucleotide 1, A % of which may be labeled). During this flow, labeled and unlabeled nucleotides may be incorporated into the growing strand (e.g., using a polymerase enzyme). A first wash flow ("wash flow 1") may be used to remove unincorporated nucleotides and associated reagents. A cleavage flow including a cleavage reagent may be provided to all or portions of the optical labeling reagents attached to incorporated nucleotides. For example, labeled nucleotides may include a cleavable linker portion that may by cleaved upon contact with the cleavage reagent to provide a scarred nucleotide. A second wash flow ("wash flow 2") may be used to remove the cleavage reagent and cleaved materials. Nucleotide flow process 1804a may also include a "chase" process in which a nucleotide flow including only unlabeled nucleotides of type Nucleotide 1 may be flowed. Such a chase process may be followed by a wash flow. The chase process and its accompanying wash flow may take place after the initial nucleotide flow and wash flow 1, or after the cleavage flow and wash flow 2. The next nucleotide flow process 1804b may then begin and proceed in similar fashion. Following completion of processes 1804b, 1804c, and 1804d, the first flow cycle 1804 may be complete. A second flow cycle 1806 may begin. Cycle 1806 may include the same flow processes in the same or different order. Additional cycles may be performed until all or a portion of the template has been sequenced. Detection of incorporated nucleotides via emission detection may be performed after nucleotide flows and initial wash flows and before cleavage flows for each nucleotide flow process (e.g., flow process 1804a may include a detection process between wash flow 1 and cleavage flow, etc.). A template interrogated by such a sequencing process may be immobilized to a support (e.g., as described herein). A plurality of such templates (e.g., at least about 100, 200, 500, 1000, 10000, 100,000, 500,000, 1,000,000, or more templates) may be interrogated contemporaneously in this fashion (e.g., in clonal fashion). In such a system, incorporation of nucleotides may be detected as an average over the plurality of templates, which may permit the use of labeling fractions of less than 100%.

In some cases, for any of the preceding methods, the nucleotide is guanine (G) and the linker decreases quenching between the nucleotide and the dye (e.g., fluorescent) dye.

In some cases, for any of the preceding methods, an optically (e.g., fluorescently) labeled nucleotide comprising a linker provided herein is more efficiently incorporated into a sequencing template than another optically (e.g., fluorescently) labeled nucleotide that comprises the same nucleotide and optical (e.g., fluorescent) dye but does not include the linker. In some cases, for any of the preceding methods, an optically (e.g., fluorescently) labeled nucleotide comprising a linker provided herein is incorporated into a sequencing template with higher fidelity than another optically (e.g., fluorescently) labeled nucleotide that comprises the same nucleotide and optical (e.g., fluorescent) dye but does not include the linker.

For any of the sequencing methods provided herein, the polymerase used may be a Family A polymerase such as Taq, Klenow, or Bst polymerase. Alternatively, for any of the sequencing methods provided herein, the polymerase may be a Family B polymerase such as Vent(exo-) or Therminator™ polymerase.

In an aspect, the present disclosure provides methods for sequencing a nucleic acid molecule using the optically (e.g., fluorescently) labeled nucleotides described herein. A method may comprise providing a plurality of nucleic acid molecules, which plurality of nucleic acid molecules may comprise or be part of a colony or a plurality of colonies. The plurality of nucleic acid molecules may have sequence homology to a template sequence. The method may comprise contacting the plurality of nucleic acid molecules with a solution comprising a plurality of nucleotides (e.g., a solution comprising a plurality of optically labeled nucleotides) under conditions sufficient to incorporate a subset of the plurality of nucleotides into a plurality of growing nucleic acid strands that is complementary to the plurality of nucleic acid molecules. In some instances, at least about 20% of the subset of the plurality of nucleotides are optically (e.g., fluorescently) labeled nucleotides (e.g., as described herein). The method may comprise detecting one or more signals or signal changes from the labeled nucleotides incorporated into the plurality of growing nucleic acid strands, wherein the one or more signals or signal changes are indicative of the labeled nucleotides having incorporated into the plurality of growing nucleic acid strands.

The optically (e.g., fluorescently) labeled nucleotides of the plurality of nucleotides may be non-terminated. In such cases, the growing strands may incorporate one or more consecutive nucleotides during (e.g., a complimentary base to the plurality of nucleotides in solution is not present at a plurality of positions adjacent to the primer hybridized to the nucleic acid molecule). The one or more signals or signal changes detected from the optically (e.g., fluorescently) labeled nucleotides may be indicative of consecutive nucleotides having incorporated into the plurality of growing nucleic acid strands. Methods for determining a number of fluorophores from the detected signals or signal changes are described elsewhere herein.

Alternatively, the optically (e.g., fluorescently) labeled nucleotides may be terminated. In such cases, each growing strand may incorporate no more than one nucleotide per flow cycle until synthesis is terminated. The one or more signals or signal changes detected from the optically (e.g., fluorescently) labeled nucleotides may be indicative of nucleotides having incorporated into the plurality of growing nucleic acid strands. Prior to, during, or subsequent to detection, a terminating group of the labeled nucleotides may be cleaved (e.g., to facilitate sequencing of homopolymers, and/or to reduce potential context and/or quenching issues).

Alternatively or in addition to, the optically (e.g., fluorescently) labeled nucleotides may include a mixture of terminated and non-terminated nucleotides. In such cases, the growing strands may incorporate one or more consecutive nucleotides generating an extended primer. The solution comprising the plurality of terminated and non-terminated nucleotides may then be washed away from the sequencing template. Un-labeled nucleotides of the plurality of nucleotides may comprise nucleotide moieties of the same type as labeled nucleotides of the plurality of nucleotides (e.g., the same canonical nucleotide).

In an aspect, the present disclosure provides compositions comprising one or more fluorescently labeled nucleotides and methods of using the same. A composition may comprise a solution comprising a fluorescently labeled nucleotide (e.g., as described herein). The fluorescently labeled nucleotide may comprise a fluorescent dye that is connected to a nucleotide or nucleotide analog (e.g., as described herein) via a linker (e.g., as described herein). The linker may comprise (i) one or more water soluble groups and (ii) two or more ring systems. At least two of the two or more ring systems may be connected to each other by no more than two $sp^3$ carbon atoms, such as by no $sp^3$ carbon atoms. For example, at least two of the two or more ring systems may be connected to each other by no more than two atoms. For example, at least two of the two or more ring systems may be connected to each other by an $sp^2$ carbon atom. The linker may comprise a non-proteinogenic amino acid comprising a ring system of the two or more ring systems. The fluorescently labeled nucleotide may be configured to emit a fluorescent signal. The fluorescently labeled nucleotide may comprise a plurality of amino acids, such as a plurality of non-proteinogenic (e.g., non-natural) amino acids. For example, the linker may comprise a plurality of hydroxyprolines. At least one water-soluble group of the one or more water-soluble groups may be appended to a ring structure of the two or more ring systems. The one or more water soluble groups may be selected from the group consisting of a pyridinium, an imidazolium, a quaternary ammonium group, a sulfonate, a phosphate, an alcohol, an amine, an imine, a nitrile, an amide, a thiol, a carboxylic acid, a polyether, an aldehyde, a boronic acid, and a boronic ester. The linker may comprise a cleavable group (e.g., an azidomethyl group, a disulfide bond, a hydrocarbyldithiomethyl group, and a 2-nitrobenzyloxy group) that is configured to be cleaved to separate the fluorescent dye from the nucleotide.

The solution (e.g., nucleotide flow) may comprise a plurality of fluorescently labeled nucleotides, each or which may comprise a fluorescent dye of a same type, a linker of a same type, and a nucleotide of a same type. Each linker of each fluorescently labeled nucleotide of the plurality of fluorescently labeled nucleotides may have the same molecular weight (e.g., they might not comprise polymers with a range of molecular weights). The solution may also comprise a plurality of unlabeled nucleotides, in which each nucleotide of the plurality of unlabeled nucleotides is of a same type as each nucleotide of the plurality of fluorescently labeled nucleotides. The ratio of the plurality of fluorescently labeled nucleotides to the plurality of unlabeled nucleotides in the solution may be at least about 1:4 (e.g., the labeling fraction may be at least 20%). For example, the ratio may be at least 1:1 (e.g., the labeling fraction may be at least 50%). Alternatively, the solution may not comprise any unlabeled nucleotides and the labeling fraction may be 100%.

The solution (e.g., nucleotide flow) may be provided to a template nucleic acid molecule coupled to a nucleic acid strand. The template nucleic acid molecule may be immobilized to a support (e.g., as described herein). For example, the template nucleic acid molecule may be immobilized to a support via an adapter. For example, the template nucleic acid molecule may be immobilized to a support via a primer to which it is hybridized. The nucleic acid strand may be at least partially complementary to a portion of the template nucleic acid molecule. The template nucleic acid molecule and nucleic acid strand coupled thereto may be subjected to conditions sufficient to incorporate a fluorescently labeled nucleotide of the solution into the nucleic acid strand coupled to the template nucleic acid molecule. Incorporation of the fluorescently labeled nucleotide may be accomplished using a polymerase enzyme (e.g., as described herein). More than one fluorescently labeled nucleotide of the solution may be incorporated, such as into a homopolymeric region of the template nucleic acid molecule. Alternatively or in addition to, an unlabeled nucleotide may be incorporated (e.g., adjacent to the fluorescently labeled nucleotide), such as into a homopolymeric region of the template nucleic acid molecule. A signal (e.g., a fluorescent signal) may be detected from the fluorescently labeled nucleotide incorporated into the nucleic acid strand. Prior to detection of the signal, a wash solution may be used to used to remove fluorescently labeled nucleotides that are not incorporated into the nucleic acid strand. After detection of the signal, the fluorescently labeled nucleotide incorporated into the nucleic acid strand may be contacted with a cleavage reagent configured to cleave the fluorescent dye from the nucleotide. The cleavage reagent may be configured to cleave the linker to provide the nucleotide attached to a portion of the linker, which portion may comprise a thiol moiety, an aromatic moiety, or a combination thereof. The nucleic acid strand, such as a nucleic acid strand of a plurality of nucleic acid strands coupled to a plurality of template nucleic acid molecules, may be contacted with a chase flow comprising only unlabeled nucleotides of a same nucleotide type (e.g., before or after detection of a signal). The nucleic acid strand coupled to the template nucleic acid molecule may also be contacted with one or more additional wash flows. The nucleic acid strand coupled to the template nucleic acid molecule may be contacted with an additional solution comprising an additional fluorescently labeled nucleotide, such as an additional fluorescently labeled nucleotide including a nucleotide of a different type. The dye of the additional fluorescently labeled nucleotide may be of a same type as the dye of the fluorescently labeled nucleotide. Similarly, the linker of the additional fluorescently labeled nucleotide may be of a same type as the linker of the fluorescently labeled nucleotide.

In another aspect, the present disclosure provides a method comprising providing a fluorescent labeling reagent (e.g., as described herein). The fluorescent labeling reagent may comprise a fluorescent dye and a linker that is connected to the fluorescent dye. The linker may comprise (i) one or more water soluble groups and (ii) two or more ring systems. At least two of the two or more ring systems may be connected to each other by no more than two $sp^3$ carbon atoms, such as by no more than two atoms. For example, at least two of the two or more ring structures may be connected to each other by an $sp^2$ carbon atom. The linker may comprise a non-proteinogenic amino acid comprising a ring system of the two or more ring systems. The fluorescent labeling reagent may be configured to emit a fluorescent signal. The fluorescent labeling reagent may comprise a plurality of amino acids, such as a plurality of non-proteinogenic (e.g., non-natural) amino acids. For example, the linker may comprise a plurality of hydroxyprolines. At least one water-soluble group of the one or more water-soluble groups may be appended to a ring structure of the two or more ring systems. The one or more water soluble groups may be selected from the group consisting of a pyridinium, an imidazolium, a quaternary ammonium group, a sulfonate, a phosphate, an alcohol, an amine, an imine, a nitrile, an amide, a thiol, a carboxylic acid, a polyether, an aldehyde, a boronic acid, and a boronic ester.

A substrate may be contacted with the fluorescent labeling reagent to generate a fluorescently labeled substrate, in which the linker connected to the fluorescent dye is associated with the substrate. The substrate may be a nucleotide or nucleotide analog (e.g., as described herein). Alternatively, the substrate may be a protein, lipid, cell, or antibody. The fluorescently labeled substrate may be configured to emit a fluorescent signal (e.g., upon excitation at an appropriate energy range), which signal may be detected (e.g., using imaging-based detection). The linker may comprise a cleavable group (e.g., an azidomethyl group, a disulfide bond, a hydrocarbyldithiomethyl group, and a 2-nitrobenzyloxy group) that is configured to be cleaved to separate the fluorescent dye from the substrate. The fluorescently labeled substrate may be contacted with a cleavage reagent configured to cleave the fluorescent labeling reagent or a portion thereof from the fluorescently labeled substrate to generate a scarred substrate. The scarred substrate may comprise a thiol moiety, an aromatic moiety, or a combination thereof. Prior to generating the scarred substrate, the fluorescently labeled substrate and a nucleic acid molecule may be subjected to conditions sufficient to incorporate the fluorescently labeled substrate into the nucleic acid molecule. Incorporation may be accomplished using a polymerase enzyme (e.g., as described herein). More than one fluorescently labeled substrate may be incorporated, such as into a homopolymeric region of the nucleic acid molecule. For example, an additional fluorescently labeled substrate may be incorporated into a position adjacent to the position into which the fluorescently labeled substrate is incorporated. Alternatively or in addition to, an unlabeled substrate (e.g., a nucleotide of a same type as the nucleotide of a fluorescently labeled nucleotide) may also be incorporated into the nucleic acid molecule, such as into adjacent positions of the nucleic acid molecule. Incorporation of an additional fluorescently labeled substrate may be done before or after generation of the scarred substrate. Similarly, incorporation of an unlabeled substrate may be done before or after generation of the scarred substrate.

The nucleic acid molecule, such as a nucleic acid molecule of a plurality of nucleic acid molecules, may be contacted with a chase flow comprising only unlabeled substrates of a same type (e.g., before or after detection of a signal from the nucleic acid molecule). The nucleic acid molecule may also be contacted with one or more additional wash flows. The nucleic acid molecule may be contacted with an additional solution comprising an additional fluorescently labeled substrate, such as an additional fluorescently labeled substrate including a nucleotide of a different type. The dye of the additional fluorescently labeled substrate may be of a same type as the dye of the fluorescently labeled substrate. Similarly, the linker of the additional fluorescently labeled substrate may be of a same type as the linker of the fluorescently labeled substrate.

The nucleic acid molecule may be immobilized to a support (e.g., as described herein). For example, the nucleic acid molecule may be immobilized to a support via an adapter. For example, the nucleic acid molecule may be immobilized to a support via a primer to which it is hybridized. The nucleic acid molecule may comprise a first nucleic acid strand that is at least partially complementary to a portion of a second nucleic acid strand. The second nucleic acid strand may comprise a template nucleic acid sequence, or a complement thereof.

The labeled nucleotides of the present disclosure may be used during sequencing operations that involve a high fraction of labeled nucleotides. For example, the present disclosure provides a method comprising contacting a nucleic acid molecule (e.g., a template nucleic acid molecule) with a solution comprising a plurality of nucleotides under conditions sufficient to incorporate a first labeled nucleotide and a second labeled nucleotide of the plurality of nucleotides into a growing strand that is at least partially complementary to the nucleic acid molecule. The first labeled nucleotide and the second labeled nucleotide may be of a same canonical base type. The first nucleotide may comprise a fluorescent dye (e.g., as described herein), which fluorescent dye may be associated with the first nucleotide via a linker (e.g., as described herein). The second nucleotide may comprise the same fluorescent dye (e.g., associated with the second nucleotide via a linker having the same chemical structure of the linker associating the first nucleotide and the fluorescent dye). A fluorescent dye coupled to a nucleotide (e.g., the first and/or second nucleotide) may be cleavable (e.g., upon application of a cleavage reagent). At least about 20% of the plurality of nucleotides may be labeled nucleotides. For example, at least 20% of the plurality of nucleotides may be associated with a fluorescent labeling reagent (e.g., as described herein). For example, at least about 50%, 70%, 80%, 90%, 95%, or 99% of the plurality of nucleotides may be labeled nucleotides. For example, all of the nucleotides of the plurality of nucleotides may be labeled nucleotides (e.g., the labeling fraction may be 100%). One or more signals or signal changes may be detected from the first labeled nucleotide and the second labeled nucleotide (e.g., as described herein). The one or more signals or signal changes may comprise fluorescent signals or signal changes. The one or more signals or signal changes may be indicative of incorporation of the first labeled nucleotide and the second labeled nucleotide. The one or more signals or signal changes may be resolved to determine a sequence of the nucleic acid molecule, or a portion thereof. Resolving the one or more signals or signal changes may comprise determining a number of consecutive nucleotides from the solution that incorporated into the growing strand. The number of consecutive nucleotides may be selected from the group consisting of 2, 3, 4, 5, 6, 7, or 8 nucleotides. Resolving the one or more signals or signal changes may comprise processing a tolerance of the solution. A third nucleotide may also be incorporated into the growing strand (e.g., before or after detection of the one or more signals or signal changes). The third nucleotide may be a nucleotide of the plurality of nucleotides of the solution. Alternatively, the third nucleotide may be provided in a separate solution, such as in a "chase" flow (e.g., as described herein). The third nucleotide may be unlabeled. Alternatively, the third nucleotide may be labeled. The first labeled nucleotide and the third nucleotide may be of a same canonical base type. Alternatively, the first labeled nucleotide and the third nucleotide may be of different canonical base types.

The method may further comprise cleaving the fluorescent dye coupled to the first labeled nucleotide. The fluorescent dye may be cleaved by application of a cleavage reagent configured to cleave a linker associating the first labeled nucleotide and the fluorescent dye. The nucleic acid molecule may be contacted with a second solution comprising a second plurality of nucleotides under conditions sufficient to incorporate a third labeled nucleotide of the second plurality of nucleotides into the growing strand. At least about 20% of the second plurality of nucleotides may be labeled nucleotides (e.g., as described herein). One or more second signals or signal changes may be detected from the third labeled nucleotide (e.g., as described herein). The one or more second signals or signal changes may be resolved to determine a second sequence of the nucleic acid molecule, or a portion thereof. The first labeled nucleotide and the third labeled nucleotide may be different canonical base types (e.g., A, C, U/T, or G). The third labeled nucleotide may comprise the fluorescent dye. The fluorescent dye may be coupled to the third labeled nucleotide via a linker (e.g., as described herein), which linker may have the same chemical structure as the linker connecting the fluorescent dye to the first labeled nucleotide or a different chemical structure.

Alternatively, the method may comprise contacting the nucleic acid molecule with a second solution comprising a second plurality of nucleotides under conditions sufficient to incorporate a third labeled nucleotide of the second plurality of nucleotides into the growing strand. At least about 20% of the second plurality of nucleotides may be labeled nucleotides (e.g., as described herein). One or more second signals or signal changes may be detected from the third labeled nucleotide (e.g., as described herein). The one or more second signals or signal changes may be resolved to determine a second sequence of the nucleic acid molecule, or a portion thereof. The first labeled nucleotide and the third labeled nucleotide may be different canonical base types (e.g., A, C, U/T, or G). The third labeled nucleotide may comprise the fluorescent dye. The fluorescent dye may be coupled to the third labeled nucleotide via a linker (e.g., as described herein), which linker may have the same chemical structure as the linker connecting the fluorescent dye to the first labeled nucleotide or a different chemical structure. Contacting the nucleic acid molecule with the second solution may be performed in absence of cleaving a fluorescent dye from the first labeled nucleotide or the second labeled nucleotide. This process may be repeated one or more times, such as 1, 2, 3, 4, 5, or more times, each with a different solution of nucleotides, in absence of cleaving a fluorescent dye from the first labeled nucleotide or the second labeled nucleotide. One or more of these different solutions of nucleotides may comprise at least 20% labeled nucleotides.

The present disclosure also provides a method comprising contacting a nucleic acid molecule with a solution comprising a plurality of non-terminated nucleotides under conditions sufficient to incorporate a labeled nucleotide and a second nucleotide of the plurality of non-terminated nucleotides into a growing strand that is at least partly complementary to the nucleic acid molecule, or a portion thereof. The labeled nucleotide and the second nucleotide may be of a same canonical base type. Alternatively, the labeled nucleotide and the second nucleotide may be of different canonical base types. The labeled nucleotide may comprise a fluorescent dye (e.g., as described herein), which fluorescent dye may be associated with the labeled nucleotide via a linker (e.g., as described herein). The second nucleotide may be a labeled nucleotide. For example, the second nucleotide may comprise the same fluorescent dye (e.g., associated with the second nucleotide via a linker having the same chemical structure of the linker associating the first nucleotide and the fluorescent dye). Alternatively, the second nucleotide may not be coupled to a fluorescent dye (e.g., the second nucleotide may be unlabeled). A fluorescent dye coupled to a nucleotide (e.g., the first and/or second nucleotide) may be cleavable (e.g., upon application of a cleavage reagent). The plurality of non-terminated nucleotides may comprise nucleotides of a same canonical base type. At least about 20% of said plurality of nucleotides may be labeled nucleotides. For example, at least 20% of the plurality of nucleotides may be associated with a fluorescent labeling reagent (e.g., as described herein). For example, at least about 50%, 70%, 80%, 90%, 95%, or 99% of the plurality of non-terminated nucleotides may be labeled nucleotides. For example, substantially all of the plurality of non-terminated nucleotides may be labeled nucleotides. For example, all of the nucleotides of the plurality of non-terminated nucleotides may be labeled nucleotides (e.g., the labeling fraction may be 100%). One or more signals or signal changes may be detected from the labeled nucleotide (e.g., as described herein). The one or more signals or signal changes may comprise fluorescent signals or signal changes. The one or more signals or signal changes may be indicative of incorporation of the labeled nucleotide. The one or more signals or signal changes may be resolved to determine a sequence of the nucleic acid molecule, or a portion thereof. Resolving the one or more signals or signal changes may comprise determining a number of consecutive nucleotides from the solution that incorporated into the growing strand. The number of consecutive nucleotides may be selected from the group consisting of 2, 3, 4, 5, 6, 7, or 8 nucleotides. Resolving the one or more signals or signal changes may comprise processing a tolerance of the solution. A third nucleotide may also be incorporated into the growing strand (e.g., before or after detection of the one or more signals or signal changes). The third nucleotide may be a nucleotide of the plurality of non-terminated nucleotides of the solution. Alternatively, the third nucleotide may be provided in a separate solution, such as in a "chase" flow (e.g., as described herein). The third nucleotide may be unlabeled. Alternatively, the third nucleotide may be labeled. The labeled nucleotide and the third nucleotide may be of a same canonical base type. Alternatively, the labeled nucleotide and the third nucleotide may be of different canonical base types.

The method may further comprise cleaving the fluorescent dye coupled to the labeled nucleotide. The fluorescent dye may be cleaved by application of a cleavage reagent configured to cleave a linker associating the labeled nucleotide and the fluorescent dye. The nucleic acid molecule may be contacted with a second solution comprising a second plurality of non-terminated nucleotides under conditions sufficient to incorporate a third labeled nucleotide of the second plurality of non-terminated nucleotides into the growing strand. At least about 20% of the second plurality of non-terminated nucleotides may be labeled nucleotides (e.g., as described herein). One or more second signals or signal changes may be detected from the third labeled nucleotide (e.g., as described herein). The one or more second signals or signal changes may be resolved to determine a second sequence of the nucleic acid molecule, or a portion thereof. The first labeled nucleotide and the third labeled nucleotide may be different canonical base types (e.g., A, C, U/T, or G). The third labeled nucleotide may comprise the fluorescent dye. The fluorescent dye may be coupled to the third labeled nucleotide via a linker (e.g., as described herein), which linker may have the same chemical structure as the linker connecting the fluorescent dye to the first labeled nucleotide or a different chemical structure.

Alternatively, the method may comprise contacting the nucleic acid molecule with a second solution comprising a second plurality of non-terminated nucleotides under conditions sufficient to incorporate a third labeled nucleotide of the second plurality of non-terminated nucleotides into the growing strand. At least about 20% of the second plurality of nucleotides may be labeled nucleotides (e.g., as described herein). One or more second signals or signal changes may be detected from the third labeled nucleotide (e.g., as described herein). The one or more second signals or signal changes may be resolved to determine a second sequence of the nucleic acid molecule, or a portion thereof. The first labeled nucleotide and the third labeled nucleotide may be different canonical base types (e.g., A, C, U/T, or G). The third labeled nucleotide may comprise the fluorescent dye. The fluorescent dye may be coupled to the third labeled nucleotide via a linker (e.g., as described herein), which linker may have the same chemical structure as the linker connecting the fluorescent dye to the first labeled nucleotide or a different chemical structure. Contacting the nucleic acid molecule with the second solution may be performed in absence of cleaving a fluorescent dye from the first labeled nucleotide or the second labeled nucleotide. This process may be repeated one or more times, such as 1, 2, 3, 4, 5, or more times, each with a different solution of nucleotides, in absence of cleaving a fluorescent dye from the first labeled nucleotide or the second labeled nucleotide. One or more of these different solutions of nucleotides may comprise at least 20% labeled nucleotides.

Methods for Synthesis of Optical Labeling Reagents

In some cases, the linkers provided herein may be prepared using peptide synthesis chemistry.

For example, a linker comprising a pyridinium moiety may be prepared using peptide synthesis chemistry. Such a method may use four bifunctional reagents to make the linker, namely: (a) $R^1A$, (b) BB, (c) AA, and (d) $AR^2$. Reagent A reacts with B to form a pyridinium group; $R^1$ and $R^2$ are hetero-bifunctional attachment groups. The synthesis begins with the group $R^1A$ (or $R^2A$). Excess BB is added to $R^1A$ to form $R^1A$-BB. The product is precipitated and washed in a less polar solvent (such as ethyl acetate or tetrahydrofuran) to remove excess BB. Excess AA is added with heat in N-methylpyrrolidone (NMP) to produce $R^1A$-BB-AA. The product is precipitated and washed in a less polar solvent. The synthesis proceeds until a linker of a particular length is formed. The group $AR^2$ is appended in the final step.

1) $R^1A$+10BB→$R^1A$-BB (wash away excess BB)
2) $R^1A$-BB+10 AA→$R^1A$-BB-AA (wash away excess AA)
3) $R^1A$-BB-AA+10 BB→$R^1A$-BB-AA-BB (wash away excess BB)
4) $R^1A$-BB-AA-BB+$AR^2$→$R^1A$-BB-AA-BB-$AR^2$ (use terminating reagent)

Figure 2A:
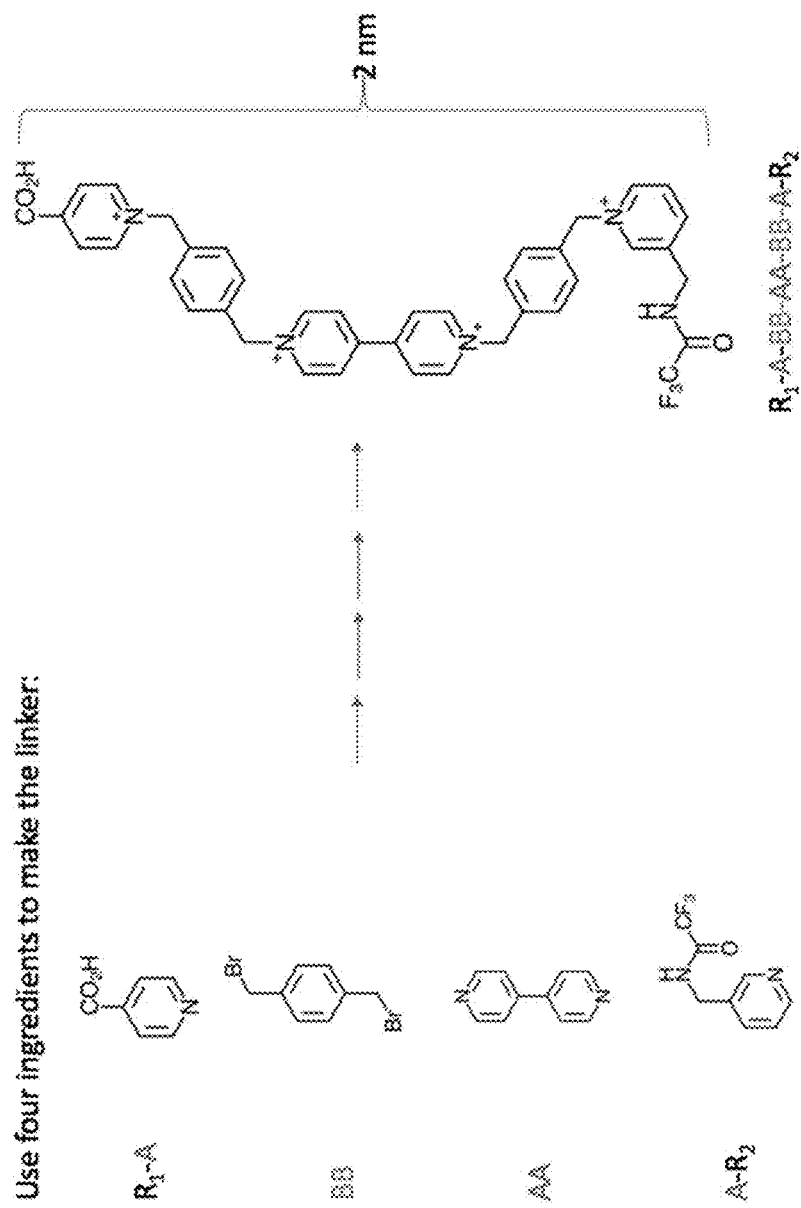
FIG. 2A shows an example of a method for synthesizing a linker of the present disclosure having an effective length of about 2 nanometers.

FIG. 2A shows an example of a method for synthesizing a linker of the present disclosure having an effective length of about 2 nanometers.

Figure 2B:
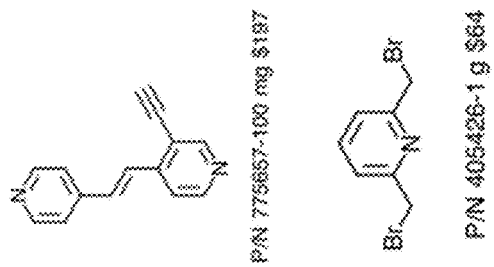
FIG. 2B shows an example of reagents that can be used in the method of FIG. 2A for synthesizing a linker of the present disclosure as well as some trifunctional reagents.
Figure 2B:
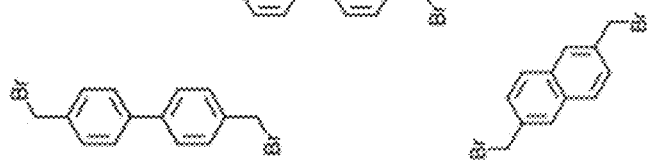
Figure 2B:

FIG. 2B shows examples of reagents that can be used in the method of FIG. 2A for synthesizing a linker of the present disclosure, as well as some trifunctional reagents.

Figure 2C:
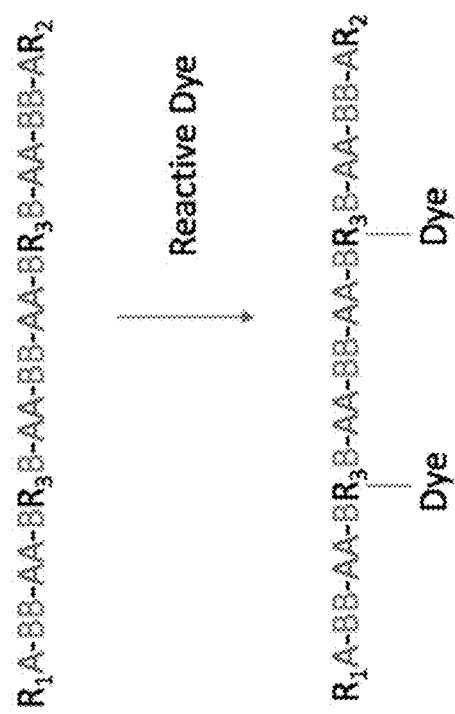
FIG. 2C shows an example of a method for synthesizing a linker of the present disclosure that is polymeric with defined molecular weight and linking groups.

FIG. 2C shows an example of a method for synthesizing a linker of the present disclosure that is polymeric with defined molecular weight and linking groups.

Additional synthetic methods for preparing optical labeling reagents (e.g., as described herein) are described elsewhere and in the Examples below.

Methods for Constructing Labeled Nucleotides

In an aspect, the present disclosure provides methods for constructing labeled nucleotides (e.g., optically labeled nucleotides).

Labeled nucleotides can be constructed using modular chemical building blocks. A nucleotide or nucleotide analog can be derivatized with, e.g., a propargylamino moiety to provide a handle for attachment to a linker or detectable label (e.g., dye). One or more detectable labels, such as one or more dyes, can be attached to a nucleotide or nucleotide analog via a covalent bond. Alternatively or in addition to, one or more detectable labels can be attached to a nucleotide or nucleotide analog via a non-covalent bond. A detectable label may be attached to a nucleotide or nucleotide analog via a linker (e.g., as described herein). A linker may include one or more moieties. For example, a linker may include a first moiety including a disulfide bond within it to facilitate cleaving the linker and releasing the detectable label (e.g., during a sequencing process). Additional linker moieties can be added using sequential peptide bonds. Linker moieties can have various lengths and charges. A linker moiety may include one or more different components, such as one or more different ring systems, and/or a repeating unit (e.g., as described herein). Examples of linkers include, but are not limited to, aminoethyl-SS-propionic acid (epSS), aminoethyl-SS-benzoic acid, aminohexyl-SS-propionic acid, hyp10, and hyp20.

Figure 4:
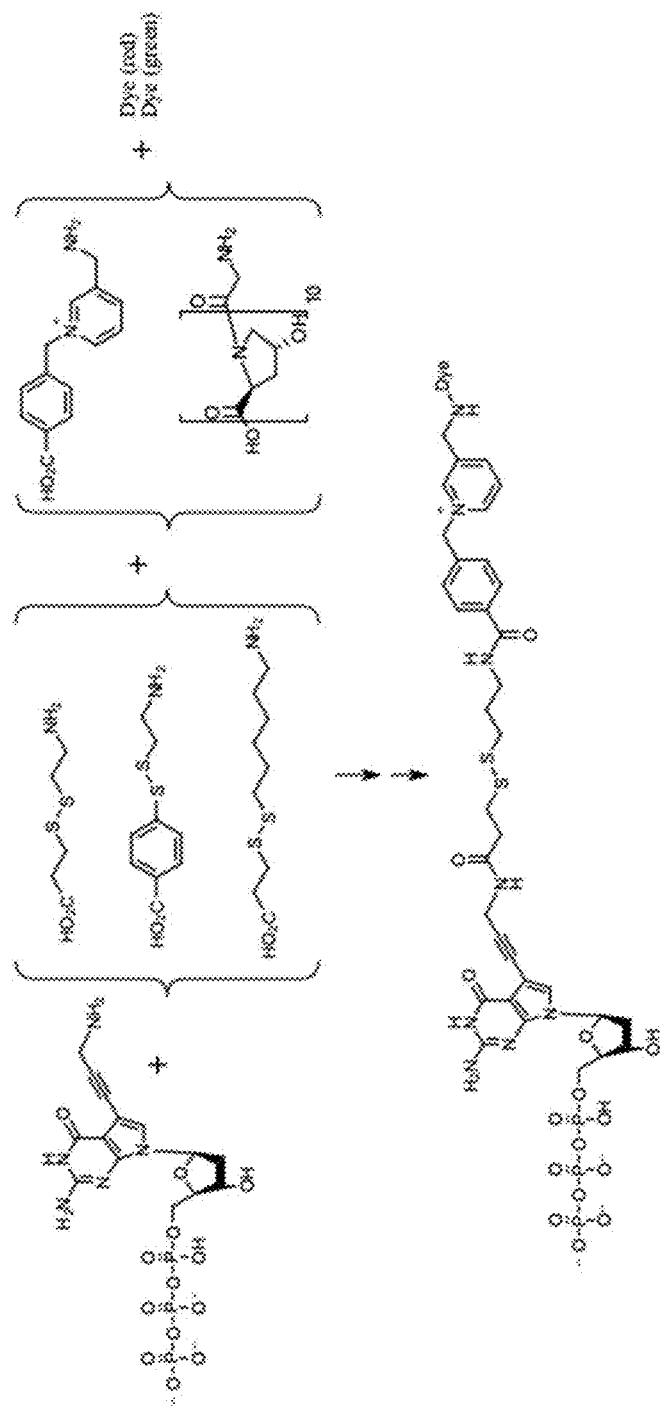
FIG. 4 shows an example of a method for constructing a labeled nucleotide comprising a propargyl-derivatized nucleotide, a linker, and a dye.
Figure 5A:
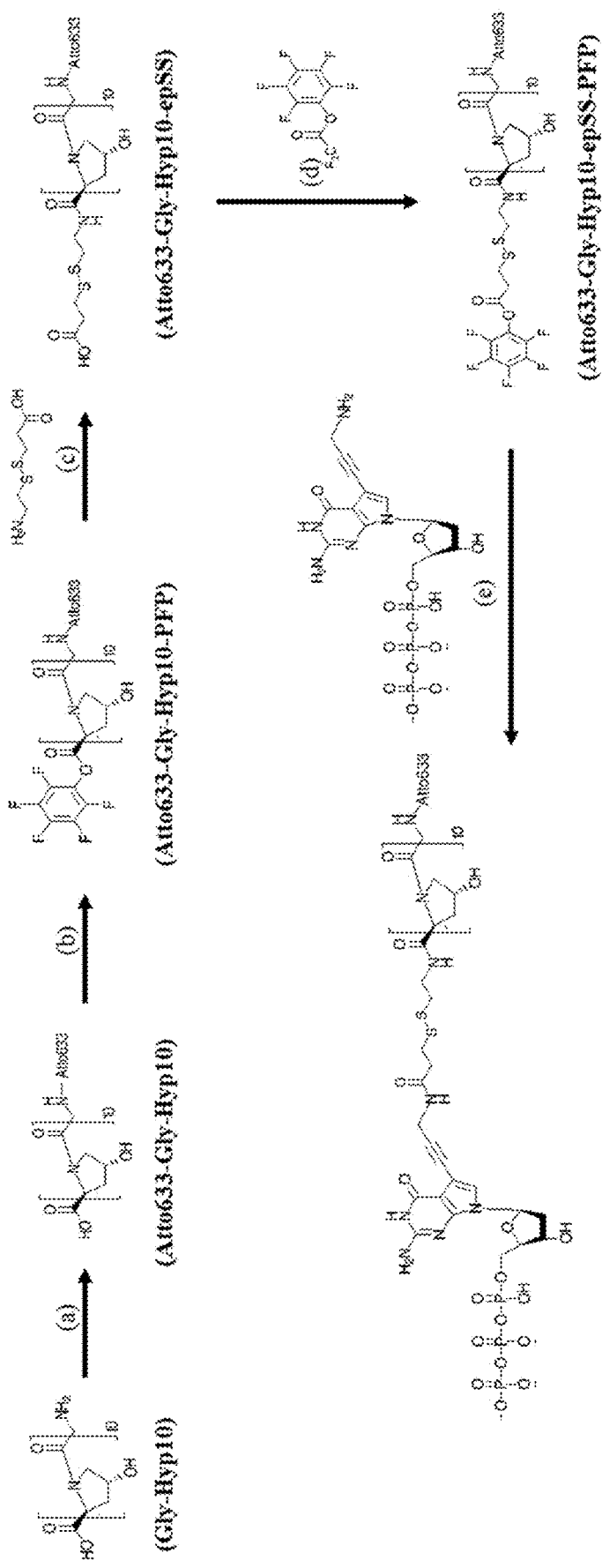
FIGS. 5A and 5B show an example method for preparing a labeled nucleotide comprising a dGTP analog.
Figure 5B:
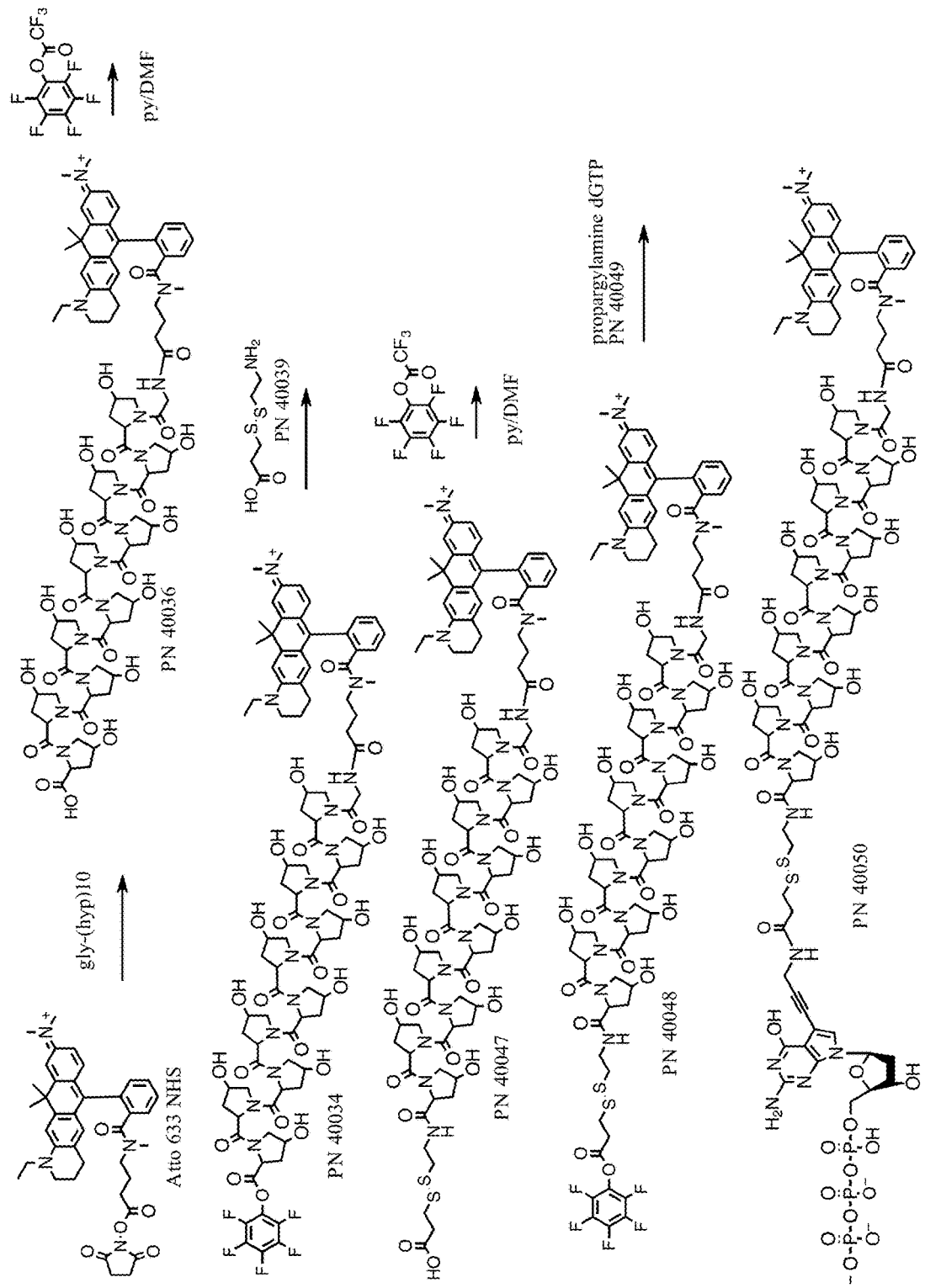

Examples of methods for constructing labeled nucleotides are shown in FIGS. 4, 5A, and 5B. As shown in FIG. 4, a labeled nucleotide may be constructed from a nucleotide, a dye, and one or more linker moieties. The one or more linker moieties together comprise a linker as described herein. A nucleotide functionalized with a propargylamino moiety can be attached to a first linker moiety via a peptide bond. This first linker moiety may comprise a cleavable moiety, such as a disulfide moiety. The first linker moiety can also be attached to one or more additional linker moieties in linear or branching fashions. For example, a second linker moiety may include two or more ring systems, wherein at least two of the two or more ring systems are separated by no more than two sp3 carbon atoms, such as by no more than two atoms. For example, at least two of the two or more ring systems may be connected to each other by an $sp^2$ carbon atom. The linker may comprise a non-proteinogenic amino acid comprising a ring system of the two or more ring systems. For example, the second linker moiety may comprise a two or more hydroxyproline moieties. An amine handle on a linker moiety may be used to attach the linker and a dye, such as a dye that fluoresces in the red or green portions of the visible electromagnetic spectrum. The labeled nucleotide generated in FIG. 4 comprises a modified deoxyadeninosine triphosphate moiety, a linker comprising a first linker moiety including a disulfide moiety and a second linker moiety including at least two ring systems, and a dye.

Construction of a labeled nucleotide can begin from either the nucleotide terminus or the dye terminus. Construction from the dye terminus permits the use of unlabeled, unactivated amino acid moieties, while construction from the nucleotide terminus may require amine-protected, carboxy-activated amino acid moieties.

FIGS. 5A and 5B show an example synthesis of a labeled nucleotide including a propargylamino functionalized dGTP moiety, a first linker moiety including a disulfide group, a second linker moiety that is hyp10, and the dye moiety Atto633. Details of this synthesis are provided in Example 3 below.

A nucleotide or nucleotide analog of a labeled nucleotide may include one or more modifications, such as one or more modifications on the nucleobase. Alternatively, a nucleotide or nucleotide analog of a labeled nucleotide may include one or more modifications not on the nucleobase. Modifications can include, but are not limited to, covalent attachment of one or more linker or label moieties, alkylation, amination, amidation, esterification, hydroxylation, halogenation, sulfurylation, and/or phosphorylation.

A nucleotide or nucleotide analog of a labeled nucleotide may include one or more modifications that are configured prevent subsequent nucleotide additions to a position adjacent to the labeled nucleotide upon its incorporation into a growing nucleic acid strand. For example, the labeled nucleotide may include a terminating or blocking group (e.g., dimethoxytrityl, phosphoramidite, or nitrobenzyl molecules). In some instances, the terminating or blocking group may be cleavable.

Scarred Substrates and Methods of Generating the Same

In an aspect, the present disclosure provides a compound of Formula (I):

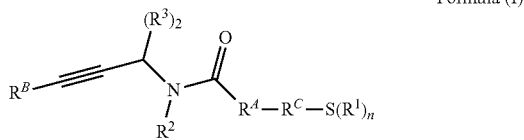

Formula (I)

or a salt or solvate thereof, wherein:

$R^A$ is an optionally substituted 5-12 membered ring system, wherein substituents on $R^A$ are independently selected from $R^4$;

$R^B$ is selected from (i) an optionally substituted monocyclic heterocycle comprising 2 or more heteroatoms and (ii) an optionally substituted bicyclic heterocycle, wherein substituents on $R^B$ are independently selected from $R^5$;

$R^C$ is selected from optionally substituted $C_{1-6}$ alkyl, optionally substituted $C_{2-6}$ alkenyl, and optionally substituted $C_{2-6}$ alkynyl, wherein substituents on $R^1$ are independently selected from $R^6$, or is absent;

$R^1$ is selected from hydrogen, halogen, —OH, —OR$^8$, =O, =S, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^1$ are independently selected from $R^6$;

$R^2$ is selected from hydrogen, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^2$ are independently selected from $R^6$;

each $R^3$ is independently selected from hydrogen, halogen, —CN, —OH, —OR$^8$, —C(=O)R$^8$, —CO$_2$R$^7$, —C(=O)N(R$^7$)$_2$, —N(R$^7$)$_2$, —NRC(=O)R$^7$, —NR$^7$C(=O)N(R$^7$)$_2$, —SR$^7$, —S(=O)R$^8$, —SO$_2$R$^8$, —SO$_2$N(R$^7$)$_2$, —NO$_2$, optionally substituted $C_1$-$C_6$ alkyl, optionally substituted $C_1$-$C_6$ alkenyl, optionally substituted $C_1$-$C_6$ alkynyl, optionally substituted monocyclic carbocycle, and optionally substituted monocyclic heterocycle, wherein optional substituents on $C_1$-$C_6$ alkyl, $C_1$-$C_6$ alkenyl, $C_1$-$C_6$ alkynyl, monocyclic carbocycle, and monocyclic heterocycle are independently selected from $R^6$;

or two $R^3$ are taken together with the atom to which they are attached to form an optionally substituted 3- to 6-membered heterocycle or carbocycle, wherein optional substituents on the 3- to 6-membered heterocycle or carbocycle are independently selected from $R^6$;

$R^4$ is selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)R$^{10}$, —OC(=O)OR$^9$, —NR$^9$SO$_2$R$^9$, —SR$^9$, —S(=O)R$^{10}$, —SO$_2$R$^{10}$, or —SO$_2$N(R$^9$)$_2$, —NO$_2$, optionally substituted $C_1$-$C_6$ alkyl, optionally substituted $C_2$-$C_6$ alkenyl, optionally substituted $C_2$-$C_6$ alkynyl, an optionally substituted $C_3$-$C_{10}$ carbocycle, and an optionally substituted 3-10-membered heterocycle, wherein substituents on $R^4$ are independently selected from $R^6$;

$R^5$ is selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —NR$^9$SO$_2$R$^9$, —SR$^9$, —S(=O)R$^{10}$, —SO$_2$R$^{10}$, or —SO$_2$N(R$^9$)$_2$, —NO$_2$, optionally substituted $C_1$-$C_6$ alkyl, optionally substituted $C_2$-$C_6$ alkenyl, optionally substituted $C_2$-$C_6$ alkynyl, an optionally substituted $C_3$-$C_{10}$ carbocycle, and an optionally substituted 3-10-membered heterocycle, wherein substituents on $R^5$ are independently selected from $R^6$;

each $R^6$ is independently selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —SR$^9$, —S(=O)R$^{10}$, —SO$_2$R$^{10}$, —SO$_2$N(R$^9$)$_2$, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, optionally substituted monophosphate, optionally substituted diphosphate, optionally substituted triphosphate, and 3- to 6-membered heterocycle;

each $R^7$ is independently selected from hydrogen, optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;

or two $R^7$ are taken together with the atom(s) to which they are attached to form an optionally substituted 3- to 6-membered heterocycle, wherein optional substituents on the 3- to 6-membered heterocycle are independently selected from $R^6$;

each $R^8$ is independently selected from optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;

each $R^9$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle;

or two $R^9$ on the same nitrogen atom are taken together with the nitrogen to which they are attached to form a 3- to 6-membered heterocycle;

each $R^{10}$ is independently selected from $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle; and n is selected from 1, 2, 3, 4, and 5.

$R^B$ may be an optionally substituted bicyclic heterocycle. For example, $R^B$ may be an optionally substituted bicyclic heterocycle in which each heteroatom of the bicyclic heterocycle is N. An optionally substituted bicyclic heterocycle may be an optionally substituted purine such as adenine, guanine, or an analog thereof. For example, $R^B$ may have a structure selected from:

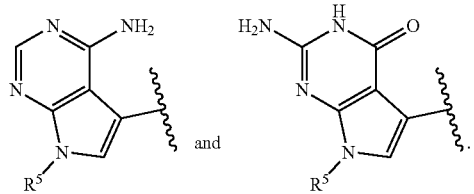

$R^B$ may be an optionally substituted monocyclic heterocycle comprising 2 or more heteroatoms. For example, $R^B$ may be an optionally substituted monocyclic heterocycle in which at least 2 heteroatoms are N. An optionally substituted monocyclic heterocycle may be an optionally substituted pyrimidine such as thymine, uracil, cytosine, or an analog thereof. For example, $R^B$ may have a structure selected from:

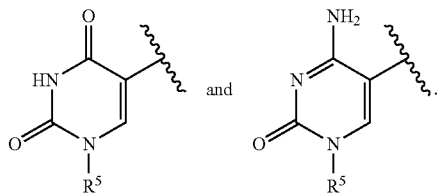

$R^B$ may be a nucleobase or nucleobase analog. For example, $R^B$ may be selected from adenine, guanine, thymine, uracil, cytosine, or an analog thereof.

$R^B$ may be substituted with at least one $R^5$. For example, $R^B$ may be substituted with at least 1, 2, 3, 4, or more $R^5$ moieties. The at least one $R^5$ may be independently selected from an optionally substituted $C_3$-$C_{10}$ carbocycle and an optionally substituted 3-10-membered heterocycle. For example, an $R^5$ may selected from an optionally substituted 5-6 membered heterocycle such as an optionally substituted ribose or deoxyribose. A ribose or deoxyribose may be substituted with a blocking group such as a terminating group. Examples of terminators include, but are not limited to, allyl, dimethoxytrityl, phosphoramidite, or nitrobenzyl moieties. A terminator may be a reversible terminator. Where the compound comprises a nucleotide, a terminator may be block incorporation of a subsequent nucleotide into a nucleic acid molecule following incorporation of the nucleotide. Alternatively, the sugar moiety of the nucleotide of the compound (e.g., ribose or deoxyribose) may not comprise a terminator, such that multiple such compounds could be incorporated into a nucleic acid molecule (e.g., using a polymerase) without a terminator removal step between such incorporations. $R^5$ may be optionally substituted with an optionally substituted mono- or polyphosphate moiety such as a diphosphate or triphosphate moiety.

$R^A$ may be selected from an optionally substituted 5-12 membered carbocyclic ring system. Alternatively, $R^A$ may be selected from an optionally substituted 5-12 membered heterocyclic ring system. $R^A$ may be an aromatic ring system (e.g., a ring system comprising one or more aromatic ring structures). $R^A$ may comprise one or more ring structures. For example, $R^A$ may be a monocycle. For example, $R^A$ may be selected from an optionally substituted 5-8 membered monocyclic ring system. For example, $R^A$ may be an optionally substituted phenyl moiety. Alternatively, $R^A$ may be a bicycle. For example, $R^A$ may be selected from an optionally substituted 5-12 membered bicyclic ring system.

$R^A$ may be substituted with at least one $R^4$. For example, $R^A$ may be substituted with at least 1, 2, 3, 4, or more $R^4$ moieties. Each $R^4$ may be independently selected from halogen, —OH, —$OR^{10}$, —$N(R^9)_2$, —C(=O)$R^9$, —C(=O)$OR^9$, —OC(=O)$R^9$, —C(=O)N($R^9$)$_2$, —$NR^9$C(=O)$R^9$, —$NR^9$C(=O)N($R^9$)$_2$, —OC(=O)N($R^9$)$_2$, —$NR^9$C(=O)$OR^9$, —OC(=O)$OR^9$, and optionally substituted $C_1$-$C_6$ alkyl. For example, each $R^4$ may be independently selected from halogen, —OH, —$OR^{10}$, and optionally substituted $C_1$-$C_6$ alkyl. For example, $R^A$ may be substituted with a halogen. Alternatively or in addition to, $R^A$ may be substituted with —OH. Alternatively or in addition to, $R^A$ may be substituted with —$OR^{10}$. Alternatively or in addition to, $R^A$ may be substituted with optionally substituted $C_1$-$C_6$ alkyl.

$R^2$ may be hydrogen. Alternatively, $R^2$ may be selected from optionally substituted $C_1$-$C_6$ alkyl.

At least one $R^3$ may be hydrogen. For example, each $R^3$ may be hydrogen. Alternatively or in addition to, at least one $R^3$ may be selected from optionally substituted $C_1$-$C_6$ alkyl.

In some cases, n is 1. In other cases, n is at least 2, such as 2, 3, 4, or 5. In an example, n may be 1 and $R^1$ may be hydrogen. In another example, an $R^1$ may be =O. For instance, n may be at least 2 and each $R^1$ may be =O. In another example, n may be at least 3, at least two $R^1$ may be =O, and a third $R^1$ may be —OH.

$R^C$ may be present or absent. For example, $R^C$ may be absent. Alternatively, $R^C$ may be selected from optionally substituted $C_1$-$C_6$ alkyl.

The compound may be a compound of Formula (II):

Formula (II)

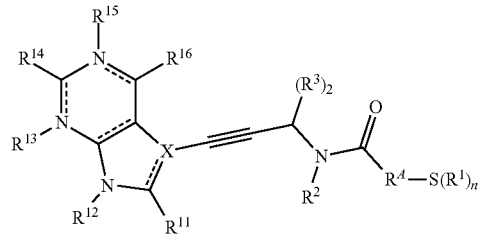

or a salt or solvate thereof, wherein:
dotted lines represent bonds that may be present or absent;
X is selected from C and N;
$R^{11}$ is selected from hydrogen, halogen, —OH, —$OR^8$, —N($R^7$)$_2$, —$SR^7$, =O, and optionally substituted $C_{1-6}$ alkyl;
$R^{12}$ is an optionally substituted 5-6 membered heterocycle;
$R^{13}$ is selected from hydrogen and optionally substituted $C_{1-6}$ alkyl, or is absent;
$R^{14}$ is selected from hydrogen, halogen, —OH, —$OR^8$, —N($R^7$)$_2$, —$SR^7$, =O, and optionally substituted $C_{1-6}$ alkyl;
$R^{15}$ is selected from hydrogen and optionally substituted $C_{1-6}$ alkyl, or is absent; and
$R^{16}$ is selected from hydrogen, halogen, —OH, —$OR^8$, —N($R^7$)$_2$, —$SR^7$, =O, and optionally substituted $C_{1-6}$ alkyl,
wherein optional substituents on $R^{11}$, $R^{13}$, $R^{14}$, $R^{15}$, and $R^{16}$ are selected from $R^{17}$; and each $R^{17}$ is independently selected from halogen, —OH, —OR$^{10}$, —N(R$^9$)$_2$, —C(=O)R$^9$, —C(=O)OR$^9$, —OC(=O)R$^9$, —C(=O)N(R$^9$)$_2$, and —NR$^9$C(=O)R$^9$.

X may be C.

$R^{12}$ may be selected from optionally substituted ribose and deoxyribose. As described above, a ribose or deoxyribose may be substituted with a blocking group such as a terminating group. $R^{12}$ may be optionally substituted with an optionally substituted mono- or polyphosphate moiety such as a diphosphate or triphosphate moiety.

$R^A$ may be an optionally substituted 5-8 membered monocyclic ring system. For example, $R^A$ may be an optionally substituted phenyl moiety.

$R^A$ may be substituted with at least one $R^4$. For example, $R^A$ may be substituted with at least 1, 2, 3, 4, or more $R^4$ moieties. Each $R^4$ may be independently selected from halogen, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, and optionally substituted C$_1$-C$_6$ alkyl. For example, each $R^4$ may be independently selected from halogen, —OH, —OR$^{10}$, and optionally substituted C$_1$-C$_6$ alkyl. For example, $R^4$ may be substituted with a halogen. Alternatively or in addition to, $R^A$ may be substituted with —OH. Alternatively or in addition to, $R^A$ may be substituted with —OR$^{10}$. Alternatively or in addition to, $R^A$ may be substituted with optionally substituted C$_1$-C$_6$ alkyl.

One or more of $R^{11}$, $R^{14}$, and $R^{16}$ may be hydrogen. Alternatively or in addition to, one or more of $R^{11}$, $R^{14}$, and $R^{16}$ may be selected from —N(R$^7$)$_2$.

One or more of $R^{13}$ and $R^{15}$ may be hydrogen. Alternatively or in addition to, one or more of $R^{13}$ and $R^{15}$ may be absent.

$R^2$ may be hydrogen. Alternatively, $R^2$ may be selected from optionally substituted C$_1$-C$_6$ alkyl.

At least one $R^3$ may be hydrogen. For example, each $R^3$ may be hydrogen. Alternatively or in addition to, at least one $R^3$ may be selected from optionally substituted C$_1$-C$_6$ alkyl.

In some cases, n is 1. In other cases, n is at least 2, such as 2, 3, 4, or 5. In an example, n may be 1 and $R^1$ may be hydrogen. In another example, an $R^1$ may be =O. For instance, n may be at least 2 and each $R^1$ may be =O. In another example, n may be at least 3, at least two $R^1$ may be =O, and a third $R^1$ may be —OH.

The compound may be a compound of Formula (III):

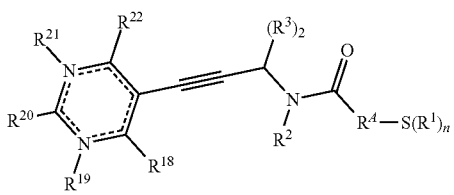

Formula (III)

or a salt or solvate thereof, wherein:
 dotted lines represent bonds that may be present or absent;
 $R^{18}$ is selected from hydrogen, halogen, —OH, —OR$^8$, —N(R$^7$)$_2$, —SR$^7$, =O, and optionally substituted C$_{1-6}$ alkyl;

$R^{19}$ is an optionally substituted 5-6 membered heterocycle;

$R^{20}$ is selected from hydrogen, halogen, —OH, —OR$^8$, —N(R$^7$)$_2$, —SR$^7$, =O, and optionally substituted C$_{1-6}$ alkyl;

$R^{21}$ is selected from hydrogen and optionally substituted C$_{1-6}$ alkyl, or is absent; and $R^{22}$ is selected from hydrogen, halogen, —OH, —OR$^8$, —N(R$^7$)$_2$, —SR$^7$, =O, and optionally substituted C$_{1-6}$ alkyl, wherein optional substituents on $R^{18}$, $R^{20}$, $R^{21}$, and $R^{22}$ are selected from $R^{23}$; and each $R^{23}$ is independently selected from halogen, —OH, —OR$^{10}$, —N(R$^9$)$_2$, —C(=O)R$^9$, —C(=O)OR$^9$, —OC(=O)R$^9$, —C(=O)N(R$^9$)$_2$, and —NR$^9$C(=O)R$^9$.

$R^{19}$ may be selected from optionally substituted ribose and deoxyribose. As described above, a ribose or deoxyribose may be substituted with a blocking group such as a terminating group. $R^{12}$ may be optionally substituted with an optionally substituted mono- or polyphosphate moiety such as a diphosphate or triphosphate moiety.

$R^A$ may be an optionally substituted 5-8 membered monocyclic ring system. For example, $R^A$ may be an optionally substituted phenyl moiety.

$R^A$ may be substituted with at least one $R^4$. For example, $R^A$ may be substituted with at least 1, 2, 3, 4, or more $R^4$ moieties. Each $R^4$ may be independently selected from halogen, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, and optionally substituted C$_1$-C$_6$ alkyl. For example, each $R^4$ may be independently selected from halogen, —OH, —OR$^{10}$, and optionally substituted C$_1$-C$_6$ alkyl. For example, $R^4$ may be substituted with a halogen. Alternatively or in addition to, $R^A$ may be substituted with —OH. Alternatively or in addition to, $R^A$ may be substituted with —OR$^{10}$. Alternatively or in addition to, $R^A$ may be substituted with optionally substituted C$_1$-C$_6$ alkyl.

One or more of $R^{18}$, $R^{20}$, and $R^{22}$ may be hydrogen. Alternatively or in addition to, one or more of $R^{18}$, $R^{20}$, and $R^{22}$ may be selected from —N(R$^7$)$_2$.

$R^2$ may be hydrogen. Alternatively, $R^2$ may be selected from optionally substituted C$_1$-C$_6$ alkyl. $R^{21}$ may be hydrogen. Alternatively, $R^{21}$ may be selected from optionally substituted C$_1$-C$_6$ alkyl. Alternatively, $R^{21}$ may be absent.

At least one $R^3$ may be hydrogen. For example, each $R^3$ may be hydrogen. Alternatively or in addition to, at least one $R^3$ may be selected from optionally substituted C$_1$-C$_6$ alkyl.

In some cases, n is 1. In other cases, n is at least 2, such as 2, 3, 4, or 5. In an example, n may be 1 and $R^1$ may be hydrogen. In another example, an $R^1$ may be =O. For instance, n may be at least 2 and each $R^1$ may be =O. In another example, n may be at least 3, at least two $R^1$ may be =O, and a third $R^1$ may be —OH.

Examples of compounds according to one or more of Formulas (I), (II), and (III) include, but are not limited to, the compounds included in Table 1.

TABLE 1
Compounds according to one or more of Formulas (I), (II), and (III).
| # | Compound |
|---|---|
| 1 | 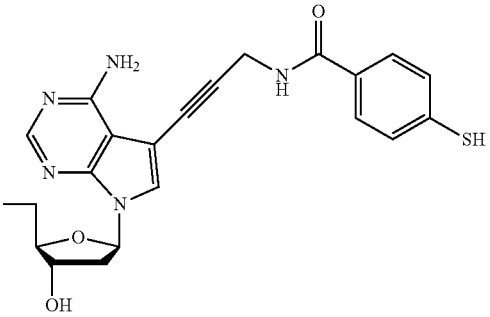 |
| 2 | 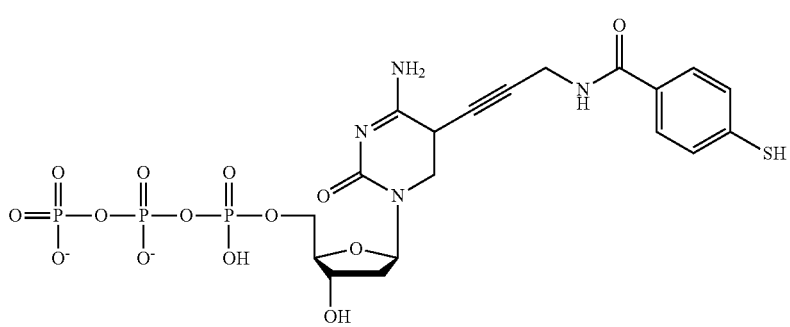 |
| 3 | 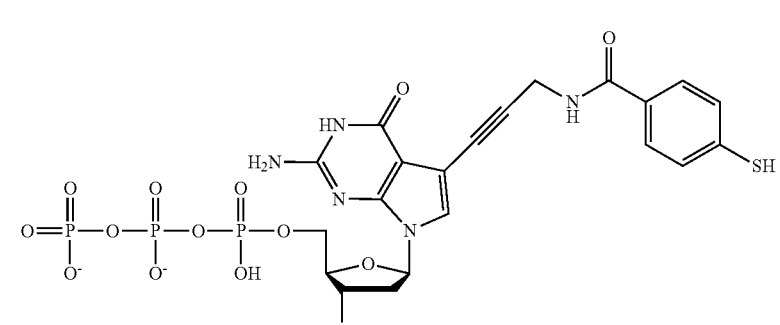 |
| 4 | 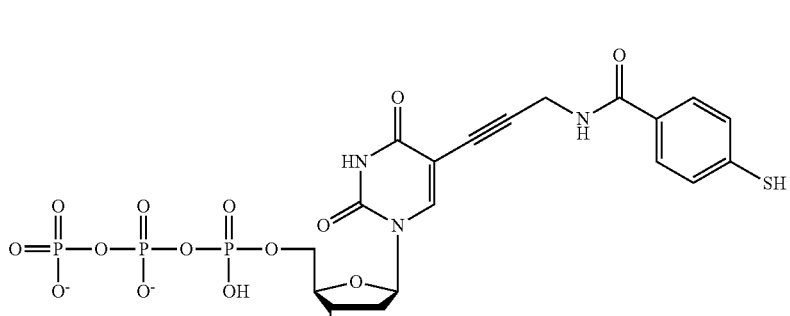 |

TABLE 1-continued

Compounds according to one or more of Formulas (I), (II), and (III).

| # | Compound |
|---|---|
| 5 | (structure: 7-deaza-deoxyadenosine triphosphate with propargyl-amide linker to 4-sulfinyl benzamide) |
| 6 | (structure: 5-substituted deoxycytidine triphosphate with propargyl-amide linker to 4-sulfinyl benzamide) |
| 7 | (structure: 7-deaza-deoxyguanosine triphosphate with propargyl-amide linker to 4-sulfinyl benzamide) |
| 8 | (structure: 5-substituted deoxyuridine triphosphate with propargyl-amide linker to 4-sulfinyl benzamide) |

TABLE 1-continued

Compounds according to one or more of Formulas (I), (II), and (III).

| # | Compound |
|---|---|
| 9 | 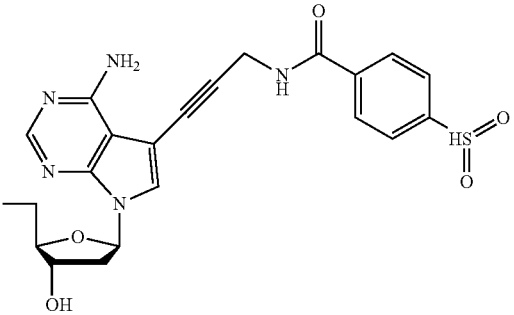 |
| 10 | 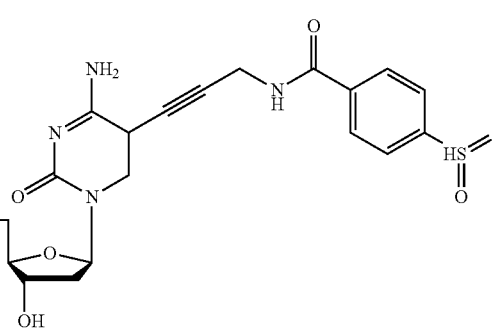 |
| 11 | 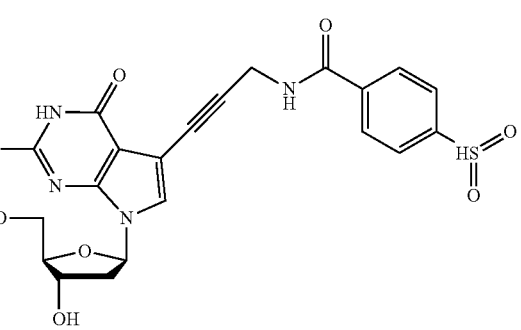 |
| 12 | 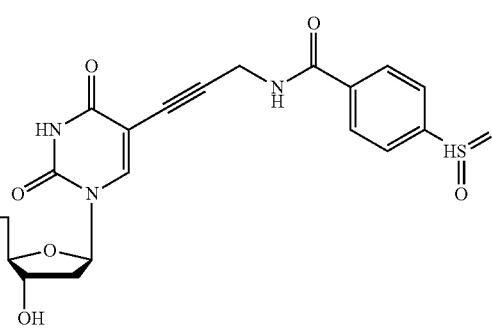 |

A compound according to one or more of Formulas (I), (II), and (III) may be included in a composition. The composition may be a solution, such as an aqueous solution. Such a solution may comprise one or more compounds according to one or more of Formulas (I), (II), and (III). The one or more compounds may be the same or different. For example, the composition may be a solution comprising a plurality of compounds according to one or more of Formulas (I), (II), and (III), all of which may have the same structure.

A compound according to one or more of Formulas (I), (II), and (III) may be included in a nucleic acid molecule. For example, a compound according to one or more of Formulas (I), (II), and (III) may be incorporated into a nucleic acid strand (e.g., a growing nucleic acid strand) coupled to a template nucleic acid molecule, where the nucleic acid strand and/or template nucleic acid molecule is immobilized to a surface.

The present disclosure also provides a method of generating a compound according to one or more of Formulas (I), (II), and (III). The method may comprise providing a labeled substrate comprising a substrate (e.g., a cell, protein, antibody, lipid, or nucleotide or nucleotide analog), a labeling moiety (e.g., a fluorescent dye), and a linker (e.g., as described herein). The linker may couple the labeling moiety to the substrate. The linker may comprise a cleavable group (e.g., as described herein) that is configured to be cleaved to separate the labeling moiety from the substrate. The labeled substrate (e.g., fluorescently labeled substrate) may be contacted with a cleavage reagent configured to cleave the cleavable group of the linker, thereby separating the labeling moiety and the substrate to provide the compound according to one or more of Formulas (I), (II), and (III).

The labeling moiety may comprise a fluorescent label (e.g., fluorescent dye). The linker may comprise a plurality of amino acids, such as a plurality of non-proteinogenic amino acids. The linker may comprise a plurality of hydroxyprolines.

The cleavable group may comprise a disulfide bond. The cleavage reagent may be selected from the group consisting of tris(2-carboxyethyl)phosphine (TCEP), dithiothreitol (DTT), tetrahydropyranyl (THP), ultraviolet (UV) light, and a combination thereof.

The substrate may be a nucleotide or nucleotide analog, such as a nucleotide or nucleotide analog that is incorporated into a polynucleotide.

A labeled substrate may have a structure according to Formula (V):

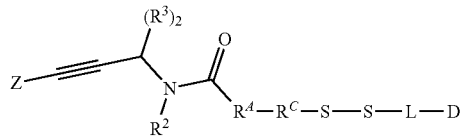

Formula (V)

or a salt thereof, wherein:
- $R^A$ is an optionally substituted 5-12 membered ring system, wherein substituents on $R^A$ are independently selected from $R^4$;
- $R^C$ is selected from optionally substituted $C_{1-6}$ alkyl, optionally substituted $C_{2-6}$ alkenyl, and optionally substituted $C_{2-6}$ alkynyl, wherein substituents on $R^1$ are independently selected from $R^6$, or is absent;
- $R^1$ is selected from hydrogen, halogen, —OH, —OR$^8$, =O, =S, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^1$ are independently selected from $R^6$;
- $R^2$ is selected from hydrogen, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^2$ are independently selected from $R^6$;
- each $R^3$ is independently selected from hydrogen, halogen, —CN, —OH, —OR$^8$, —C(=O)R$^8$, —CO$_2$R$^7$, —C(=O)N(R$^7$)$_2$, —N(R$^7$)$_2$, —NRC(=O)R$^7$, —NR$^7$C(=O)N(R$^7$)$_2$, —SR$^7$, —S(=O)R$^8$, —SO$_2$R$^8$, —SO$_2$N(R$^7$)$_2$, —NO$_2$, optionally substituted $C_1$-$C_6$ alkyl, optionally substituted $C_1$-$C_6$ alkenyl, optionally substituted $C_1$-$C_6$ alkynyl, optionally substituted monocyclic carbocycle, and optionally substituted monocyclic heterocycle, wherein optional substituents on $C_1$-$C_6$ alkyl, $C_1$-$C_6$ alkenyl, $C_1$-$C_6$ alkynyl, monocyclic carbocycle, and monocyclic heterocycle are independently selected from $R^6$;
- or two $R^3$ are taken together with the atom to which they are attached to form an optionally substituted 3- to 6-membered heterocycle or carbocycle, wherein optional substituents on the 3- to 6-membered heterocycle or carbocycle are independently selected from $R^6$;
- $R^4$ is selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —NR$^9$SO$_2$R$^9$, —SR$^9$, —S(=O)R$^{10}$, —SO$_2$R$^{10}$, or —SO$_2$N(R$^9$)$_2$, —NO$_2$, optionally substituted $C_1$-$C_6$ alkyl, optionally substituted $C_2$-$C_6$ alkenyl, optionally substituted $C_2$-$C_6$ alkynyl, an optionally substituted $C_3$-$C_{10}$ carbocycle, and an optionally substituted 3-10-membered heterocycle, wherein substituents on $R^4$ are independently selected from $R^6$;
- each $R^6$ is independently selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —SR$^9$, —S(=O)R$^{10}$, —SO$_2$R$^{10}$, —SO$_2$N(R$^9$)$_2$, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, optionally substituted monophosphate, optionally substituted diphosphate, optionally substituted triphosphate, and 3- to 6-membered heterocycle;
- each $R^7$ is independently selected from hydrogen, optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;
- or two $R^7$ are taken together with the atom(s) to which they are attached to form an optionally substituted 3- to 6-membered heterocycle, wherein optional substituents on the 3- to 6-membered heterocycle are selected from $R^6$;
- each $R^8$ is independently selected from optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;
- each $R^9$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle;
- or two $R^9$ on the same nitrogen atom are taken together with the nitrogen to which they are attached to form a 3- to 6-membered heterocycle;
- each $R^{10}$ is independently selected from $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle;
- n is selected from 1, 2, 3, 4, and 5;
- Z is a substrate selected from a nucleotide or nucleotide analog, cell, protein, lipid, and antibody;
- L is a linker moiety; and
- D is a label moiety.

Z may be a substrate such as a cell, protein, lipid, or antibody. Z may be a nucleotide or nucleotide analog (e.g., as described herein). The nucleotide or nucleotide analog may be incorporated into a polynucleotide (e.g., as described herein). For example, the nucleotide or nucleotide analog may comprise adenine, guanine, cytosine, thymine, uracil, or an analog thereof. The nucleotide or nucleotide analog may be terminated or non-terminated (e.g., as described herein). Z may comprise a plurality of moieties shown in Formula (IV), such as at least 1, 2, 3, or more such moieties.

D may be a label moiety, such as a fluorescent dye (e.g., as described herein).

L may be a linker moiety (e.g., as described herein). As described elsewhere herein, a linker may comprise multiple components, including a cleavable component and another component, such as another component including two or more ring systems. The structure shown in Formula (V) includes a cleavable component. The cleavable component includes a disulfide bond. The other component of the linker may comprise a plurality of amino acids, such as a plurality of non-proteinogenic amino acids (e.g., as described herein). For example, the other component of the linker may comprise a plurality of hydroxyprolines.

$R^A$ may be selected from an optionally substituted 5-12 membered carbocyclic ring system. Alternatively, $R^A$ may be selected from an optionally substituted 5-12 membered heterocyclic ring system. $R^A$ may be an aromatic ring system (e.g., a ring system comprising one or more aromatic ring structures). $R^A$ may comprise one or more ring structures. For example, $R^A$ may be a monocycle. For example, $R^A$ may be selected from an optionally substituted 5-8 membered monocyclic ring system. For example, $R^A$ may be an optionally substituted phenyl moiety. Alternatively, $R^A$ may be a bicycle. For example, $R^A$ may be selected from an optionally substituted 5-12 membered bicyclic ring system.

$R^A$ may be substituted with at least one $R^4$. For example, $R^A$ may be substituted with at least 1, 2, 3, 4, or more $R^4$ moieties. Each $R^4$ may be independently selected from halogen, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, and optionally substituted $C_1$-$C_6$ alkyl. For example, each $R^4$ may be independently selected from halogen, —OH, —OR$^{10}$, and optionally substituted $C_1$-$C_6$ alkyl. For example, $R^4$ may be substituted with a halogen. Alternatively or in addition to, $R^4$ may be substituted with —OH. Alternatively or in addition to, $R^4$ may be substituted with —OR$^{10}$. Alternatively or in addition to, $R^4$ may be substituted with optionally substituted $C_1$-$C_6$ alkyl.

$R^2$ may be hydrogen. Alternatively, $R^2$ may be selected from optionally substituted $C_1$-$C_6$ alkyl.

At least one $R^3$ may be hydrogen. For example, each $R^3$ may be hydrogen. Alternatively or in addition to, at least one $R^3$ may be selected from optionally substituted $C_1$-$C_6$ alkyl.

In some cases, n is 1. In other cases, n is at least 2, such as 2, 3, 4, or 5. In an example, n may be 1 and $R^1$ may be hydrogen. In another example, an $R^1$ may be =O. For instance, n may be at least 2 and each $R^1$ may be =O. In another example, n may be at least 3, at least two $R^1$ may be =O, and a third $R^1$ may be —OH.

$R^C$ may be present or absent. For example, $R^C$ may be absent. Alternatively, $R^C$ may be selected from optionally substituted $C_1$-$C_6$ alkyl.

An example of a labeled substrate according to Formula (V) is shown below:

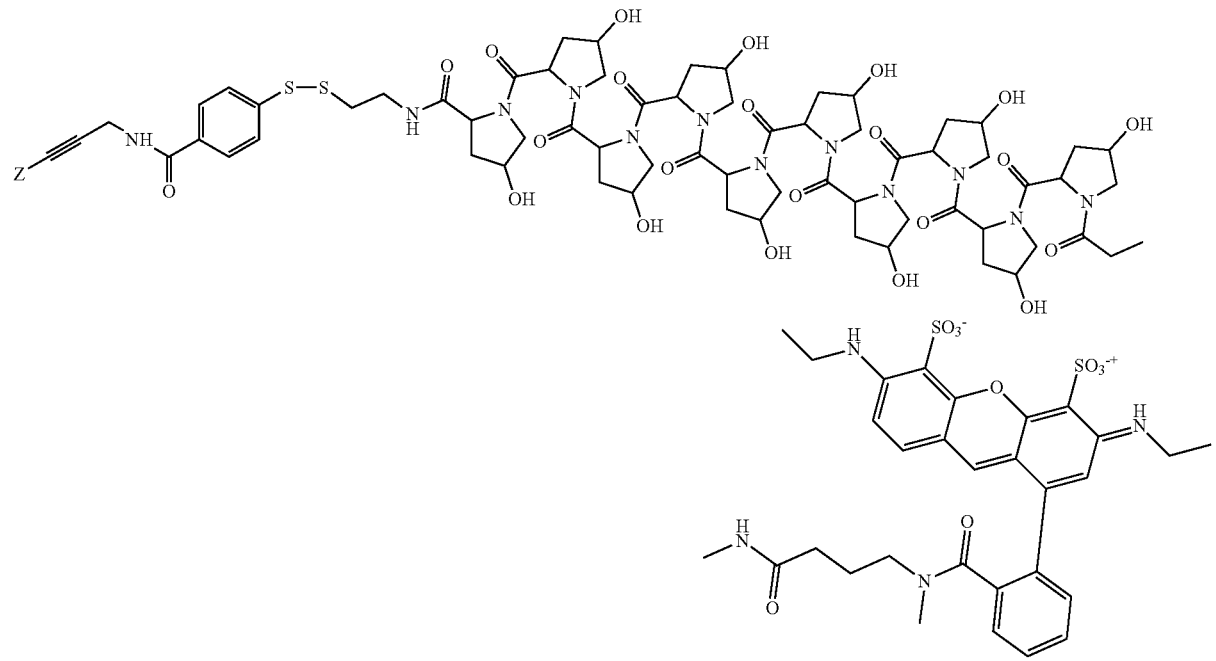

The labeled substrate shown above includes a hyp10 moiety, as described herein.

The present disclosure also provides a modified polynucleotide comprising a compound according to one or more of Formulas (I), (II), and (III). The modified polynucleotide may comprise two or more compounds according to one or more of Formulas (I), (II), and (III). The two or more compounds may have the same or different structures. The two or more compounds may be separated by at least one nucleotide, such as by at least 1, 2, 3, 4, or more nucleotides. The two or more compounds may be included in a same strand of the modified polynucleotide, such as a strand coupled to a template nucleic acid strand.

The present disclosure also provides a method of generating a modified polynucleotide, such as a modified polynucleotide comprising a compound according to one or more of Formulas (I), (II), and (III). The method may comprise providing a precursor of the compound and a template nucleic acid molecule coupled to a nucleic acid strand. The template nucleic acid molecule coupled to the nucleic acid strand may be immobilized to a support. The precursor of the compound and the template nucleic acid molecule may be subjected to conditions sufficient to incorporate the precursor of the compound into the nucleic acid strand coupled to the template nucleic acid molecule. The precursor of the compound incorporated into the nucleic acid strand may be subjected to conditions sufficient to generate the compound from the precursor of the compound.

The precursor of the compound may comprise a linker (e.g., as described herein). The linker of the precursor of the compound may comprise a cleavable group (e.g., as described herein). For example, the linker may comprise a disulfide bond. The cleavable group may be configured to be cleaved to separate a labeling moiety from a substrate. The linker may couple a portion of the precursor of the compound (e.g., a substrate such as a nucleotide or nucleotide analog) to a labeling moiety (e.g., a fluorescent dye, as described herein).

Incorporating the precursor of the compound may be accomplished using a polymerase enzyme, such as a strand-displacement polymerase enzyme (e.g., as described herein).

The template nucleic acid molecule may comprise deoxyribonucleic acid. Alternatively or in addition to, the template nucleic acid molecule may comprise ribonucleic acid.

Subjecting the precursor of the compound to conditions sufficient to generate the compound from the precursor may comprise contacting the precursor of the compound with a cleavage reagent configured to cleave a cleavable group of a linker, thereby generating the compound. This may achieved, e.g., in a solution. The cleavage reagent may be provided in a cleavage flow (e.g., as described herein).

The present disclosure also provides a composition comprising a chemical moiety of Formula (IV):

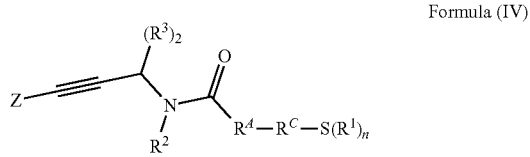

Formula (IV)

or a salt or solvate thereof, wherein:
- $R^A$ is an optionally substituted 5-12 membered ring system, wherein substituents on $R^A$ are independently selected from $R^4$;
- $R^C$ is selected from optionally substituted $C_{1-6}$ alkyl, optionally substituted $C_{2-6}$ alkenyl, and optionally substituted $C_{2-6}$ alkynyl, wherein substituents on $R^1$ are independently selected from $R^6$, or is absent;
- $R^1$ is selected from hydrogen, halogen, —OH, —OR$^8$, =O, =S, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^1$ are independently selected from $R^6$;
- $R^2$ is selected from hydrogen, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^2$ are independently selected from $R^6$;
- each $R^3$ is independently selected from hydrogen, halogen, —CN, —OH, —OR$^8$, —C(=O)R$^8$, —CO$_2$R$^7$, —C(=O)N(R$^7$)$_2$, —N(R$^7$)$_2$, —NRC(=O)R$^7$, —NR$^7$C(=O)N(R$^7$)$_2$, —SR$^7$, —S(=O)R$^8$, —SO$_2$R$^8$, —SO$_2$N(R$^7$)$_2$, —NO$_2$, optionally substituted $C_1$-$C_6$ alkyl, optionally substituted $C_1$-$C_6$ alkenyl, optionally substituted $C_1$-$C_6$ alkynyl, optionally substituted monocyclic carbocycle, and optionally substituted monocyclic heterocycle, wherein optional substituents on $C_1$-$C_6$ alkyl, $C_1$-$C_6$ alkenyl, $C_1$-$C_6$ alkynyl, monocyclic carbocycle, and monocyclic heterocycle are independently selected from $R^6$;
- or two $R^3$ are taken together with the atom to which they are attached to form an optionally substituted 3- to 6-membered heterocycle or carbocycle, wherein optional substituents on the 3- to 6-membered heterocycle or carbocycle are independently selected from $R^6$;
- $R^4$ is selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —NR$^9$SO$_2$R$^9$, —SR$^9$, —S(=O)R$^{10}$, —SO$_2$R$^{10}$, or —SO$_2$N(R$^9$)$_2$, —NO$_2$, optionally substituted $C_1$-$C_6$ alkyl, optionally substituted $C_2$-$C_6$ alkenyl, optionally substituted $C_2$-$C_6$ alkynyl, an optionally substituted $C_3$-$C_{10}$ carbocycle, and an optionally substituted 3-10-membered heterocycle, wherein substituents on $R^4$ are independently selected from $R^6$;
- each $R^6$ is independently selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —SR$^9$, —S(=O)R$^{10}$, —SO$_2$R$^{10}$, —SO$_2$N(R$^9$)$_2$, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, optionally substituted monophosphate, optionally substituted diphosphate, optionally substituted triphosphate, and 3- to 6-membered heterocycle;
- each $R^7$ is independently selected from hydrogen, optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;
- or two $R^7$ are taken together with the atom(s) to which they are attached to form an optionally substituted 3- to 6-membered heterocycle, wherein optional substituents on the 3- to 6-membered heterocycle are independently selected from $R^6$;
- each $R^8$ is independently selected from optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;

each $R^9$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle; or two $R^9$ on the same nitrogen atom are taken together with the nitrogen to which they are attached to form a 3- to 6-membered heterocycle;

each $R^{10}$ is independently selected from $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle;

n is selected from 1, 2, 3, 4, and 5; and

Z is a substrate selected from a nucleotide or nucleotide analog, cell, protein, lipid, and antibody.

Z may be a substrate such as a cell, protein, lipid, or antibody. Z may be a nucleotide or nucleotide analog (e.g., as described herein). The nucleotide or nucleotide analog may be incorporated into a polynucleotide (e.g., as described herein). For example, the nucleotide or nucleotide analog may comprise adenine, guanine, cytosine, thymine, uracil, or an analog thereof. The nucleotide or nucleotide analog may be terminated or non-terminated (e.g., as described herein). Z may comprise a plurality of moieties shown in Formula (IV), such as at least 1, 2, 3, or more such moieties.

$R^A$ may be selected from an optionally substituted 5-12 membered carbocyclic ring system. Alternatively, $R^A$ may be selected from an optionally substituted 5-12 membered heterocyclic ring system. $R^A$ may be an aromatic ring system (e.g., a ring system comprising one or more aromatic ring structures). $R^A$ may comprise one or more ring structures. For example, $R^A$ may be a monocycle. For example, $R^A$ may be selected from an optionally substituted 5-8 membered monocyclic ring system. For example, $R^A$ may be an optionally substituted phenyl moiety. Alternatively, $R^A$ may be a bicycle. For example, $R^A$ may be selected from an optionally substituted 5-12 membered bicyclic ring system.

$R^A$ may be substituted with at least one $R^4$. For example, $R^A$ may be substituted with at least 1, 2, 3, 4, or more $R^4$ moieties. Each $R^4$ may be independently selected from halogen, —OH, —$OR^{10}$, —$N(R^9)_2$, —C(=O)$R^9$, —C(=O)$OR^9$, —OC(=O)$R^9$, —C(=O)N($R^9)_2$, —$NR^9$C(=O)$R^9$, —$NR^9$C(=O)N($R^9)_2$, —OC(=O)N($R^9)_2$, —$NR^9$C(=O)$OR^9$, —OC(=O)$OR^9$, and optionally substituted $C_1$-$C_6$ alkyl. For example, each $R^4$ may be independently selected from halogen, —OH, —$OR^{10}$, and optionally substituted $C_1$-$C_6$ alkyl. For example, $R^A$ may be substituted with a halogen. Alternatively or in addition to, $R^A$ may be substituted with —OH. Alternatively or in addition to, $R^A$ may be substituted with —$OR^{10}$. Alternatively or in addition to, $R^A$ may be substituted with optionally substituted $C_1$-$C_6$ alkyl.

$R^2$ may be hydrogen. Alternatively, $R^2$ may be selected from optionally substituted $C_1$-$C_6$ alkyl.

At least one $R^3$ may be hydrogen. For example, each $R^3$ may be hydrogen. Alternatively or in addition to, at least one $R^3$ may be selected from optionally substituted $C_1$-$C_6$ alkyl.

In some cases, n is 1. In other cases, n is at least 2, such as 2, 3, 4, or 5. In an example, n may be 1 and $R^1$ may be hydrogen. In another example, an may be =O. For instance, n may be at least 2 and each $R^1$ may be =O. In another example, n may be at least 3, at least two $R^1$ may be =O, and a third $R^1$ may be —OH.

$R^C$ may be present or absent. For example, $R^C$ may be absent. Alternatively, $R^C$ may be selected from optionally substituted $C_1$-$C_6$ alkyl.

Examples of chemical moieties according to Formula (IV) include, but are not limited to, the compounds included in Table 2.

TABLE 2

Chemical moieties according to Formula (IV).

| Compound | |
|---|---|
| 13 | [Structure: Z–CH₂–C≡CH–NH–C(=O)–(4-SH-phenyl)] |
| 14 | [Structure: Z–CH₂–C≡CH–NH–C(=O)–(4-S(=O)H-phenyl)] |
| 15 | [Structure: Z–CH₂–C≡CH–NH–C(=O)–(4-S(=O)(=O)H-phenyl), HS group] |
| 16 | [Structure: Z–CH₂–C≡CH–N(CH₃)–C(=O)–(4-SH-phenyl)] |
| 17 | [Structure: Z–CH₂–C≡CH–N(CH₃)–C(=O)–(4-S(=O)H-phenyl)] |
| 18 | [Structure: Z–CH₂–C≡CH–N(CH₃)–C(=O)–(4-S(=O)(=O)H-phenyl), HS group] |
| 19 | [Structure: Z–CH₂–C≡CH–NH–C(=O)–(3-SH-phenyl)] |
| 20 | [Structure: Z–CH₂–C≡CH–NH–C(=O)–(3-S(=O)H-phenyl)] |

TABLE 2-continued
Chemical moieties according to Formula (IV).
| Compound | |
|---|---|
| 21 | 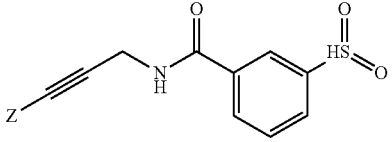 |
| 22 | 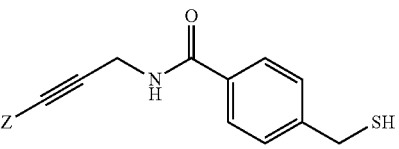 |
| 23 | 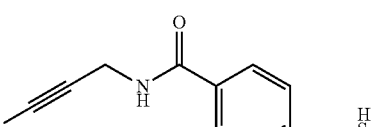 |
| 24 | 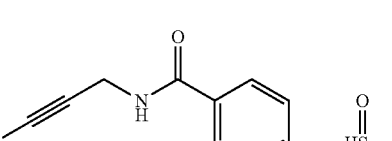 |
| 25 | 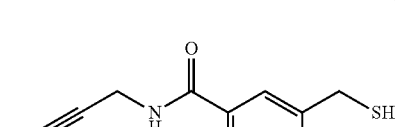 |
| 26 | 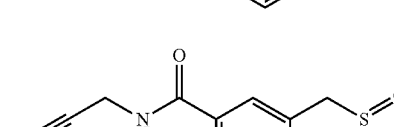 |
| 27 | 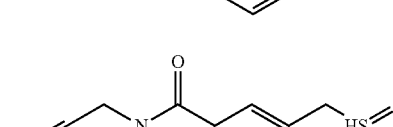 |
| 28 | 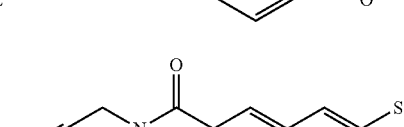 |
| 29 | 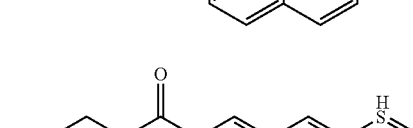 |
| 30 | 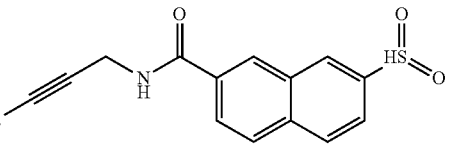 |
| 31 | 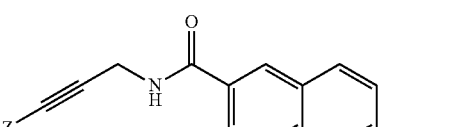 |
| 32 | 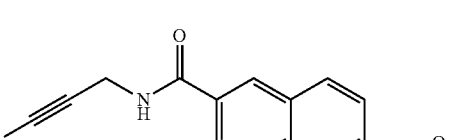 |
| 33 | 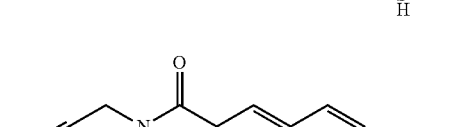 |
| 34 | 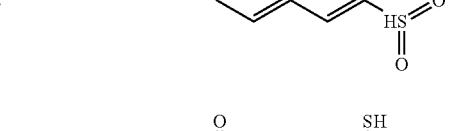 |
| 35 | 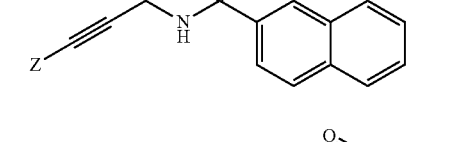 |
| 36 | 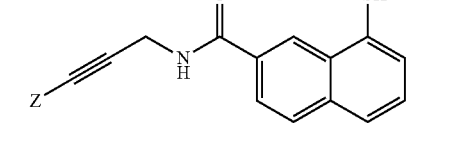 |
| 37 | 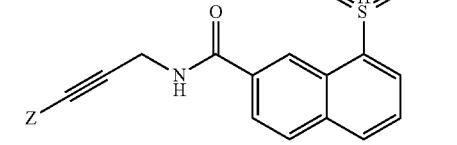 |

TABLE 2-continued

Chemical moieties according to Formula (IV).

| Compound | |
|---|---|
| 38 | (structure) |
| 39 | (structure) |
| 40 | (structure) |
| 41 | (structure) |
| 42 | (structure) |
| 43 | (structure) |
| 44 | (structure) |
| 45 | (structure) |
| 46 | (structure) |
| 47 | (structure) |
| 48 | (structure) |
| 49 | (structure) |
| 50 | (structure) |
| 51 | (structure) |
| 52 | (structure) |

TABLE 2-continued

Chemical moieties according to Formula (IV).

| Compound | |
|---|---|
| 53 | (structure) |
| 54 | (structure) |
| 55 | (structure) |
| 56 | (structure) |
| 57 | (structure) |
| 58 | (structure) |
| 59 | (structure) |
| 60 | (structure) |
| 61 | (structure) |
| 62 | (structure) |
| 63 | (structure) |
| 64 | (structure) |
| 65 | (structure) |
| 66 | (structure) |
| 67 | (structure) |
| 68 | (structure) |
| 69 | (structure) |
| 70 | (structure) |

TABLE 2-continued

Chemical moieties according to Formula (IV).

| Compound | |
|---|---|
| 71 | (structure: Z–propargyl–NH–C(=O)–quinoline–7–S(=O)H) |
| 72 | (structure: Z–propargyl–NH–C(=O)–quinoline–7–S(=O)(=O)H) |
| 73 | (structure: Z–propargyl–NH–C(=O)–quinoline–2–SH) |
| 74 | (structure: Z–propargyl–NH–C(=O)–quinoline–2–S(=O)H) |
| 75 | (structure: Z–propargyl–NH–C(=O)–quinoline–2–S(=O)(=O)H) |
| 76 | (structure: Z–propargyl–NH–C(=O)–quinoline–4–SH) |
| 77 | (structure: Z–propargyl–NH–C(=O)–quinoline–4–S(=O)(=O)H) |
| 78 | (structure: Z–propargyl–NH–C(=O)–quinoline–4–S(=O)(=O)(OH)) |

For the chemical moieties included in Table 2, Z may be, for example, a nucleotide or nucleotide analog, protein, lipid, antibody, or cell. For example, Z may be a nucleotide or nucleotide analog (e.g., as described herein).

The present disclosure also provides a method of generating a composition comprising a chemical moiety of Formula (IV). The method may comprise providing a labeled substrate comprising a substrate (e.g., a cell, protein, antibody, lipid, or nucleotide or nucleotide analog), a labeling moiety (e.g., a fluorescent dye), and a linker (e.g., as described herein). The linker may couple the labeling moiety to the substrate. The linker may comprise a cleavable group (e.g., as described herein) that is configured to be cleaved to separate the labeling moiety from the substrate. The labeled substrate (e.g., fluorescently labeled substrate) may be contacted with a cleavage reagent configured to cleave the cleavable group of the linker, thereby separating the labeling moiety and the substrate to provide the composition comprising a chemical moiety according to Formula (IV).

The labeling moiety may comprise a fluorescent label (e.g., fluorescent dye). The linker may comprise a plurality of amino acids, such as a plurality of non-proteinogenic amino acids. The linker may comprise a plurality of hydroxyprolines.

The cleavable group may comprise a disulfide bond. The cleavage reagent may be selected from the group consisting of tris(2-carboxyethyl)phosphine (TCEP), dithiothreitol (DTT), tetrahydropyranyl (THP), ultraviolet (UV) light, and a combination thereof.

The substrate may be a nucleotide or nucleotide analog, such as a nucleotide or nucleotide analog that is incorporated into a polynucleotide. Alternatively, the substrate may be a protein, lipid, cell, or antibody.

In an aspect, the present disclosure provides a substrate coupled to a scar moiety. A substrate coupled to a scar moiety may be, for example, a protein, cell, lipid, or antibody. A substrate may be a nucleotide or nucleotide analog (e.g., as described herein). A scar moiety may be a moiety comprising a portion or derivative of a cleavable group. For example, a scar moiety may comprise a portion or derivative of a disulfide bond such as a sulfur radical. A sulfur radical may bond to a hydrogen atom to provide a thiol group. A sulfur radical or thiol group may undergo an oxidation process to provide, for example, a sulfoxide, sulfone, sulfonic acid, dithiol, or another moiety. Alternatively or in addition to, a scar moiety may comprise a portion or derivative of an alkylazido (e.g., azidomethyl) moiety such as a nitrogen radical (e.g., a nitrogen radical of a diazene moiety). Alternatively or in addition to, a scar moiety may comprise a portion or derivative of a hydrocarbyldithiomethyl moiety. Alternatively or in addition to, a scar moiety may comprise a portion or derivative of a 2-nitrobenzyloxy moiety. A scar moiety coupled to a substrate may comprise a chemical moiety according to any one of Formulas (I), (II), or (III).

The present disclosure also provides a modified polynucleotide comprising a nucleotide or nucleotide analog having a scar moiety attached thereto. As described above, the scar moiety may be a moiety comprising a portion or derivative of a cleavable group, such as a portion or derivative of a disulfide bond. For example, the modified polynucleotide may comprise a thiol, a sulfoxide, sulfone, sulfonic acid, dithiol, or another moiety derived from a disulfide bond, e.g., upon cleavage of a disulfide bond using a cleavage reagent. The modified polynucleotide may comprise a chemical moiety according to any one of Formulas (I), (II), or (III).

Computer Systems

Figure 3:
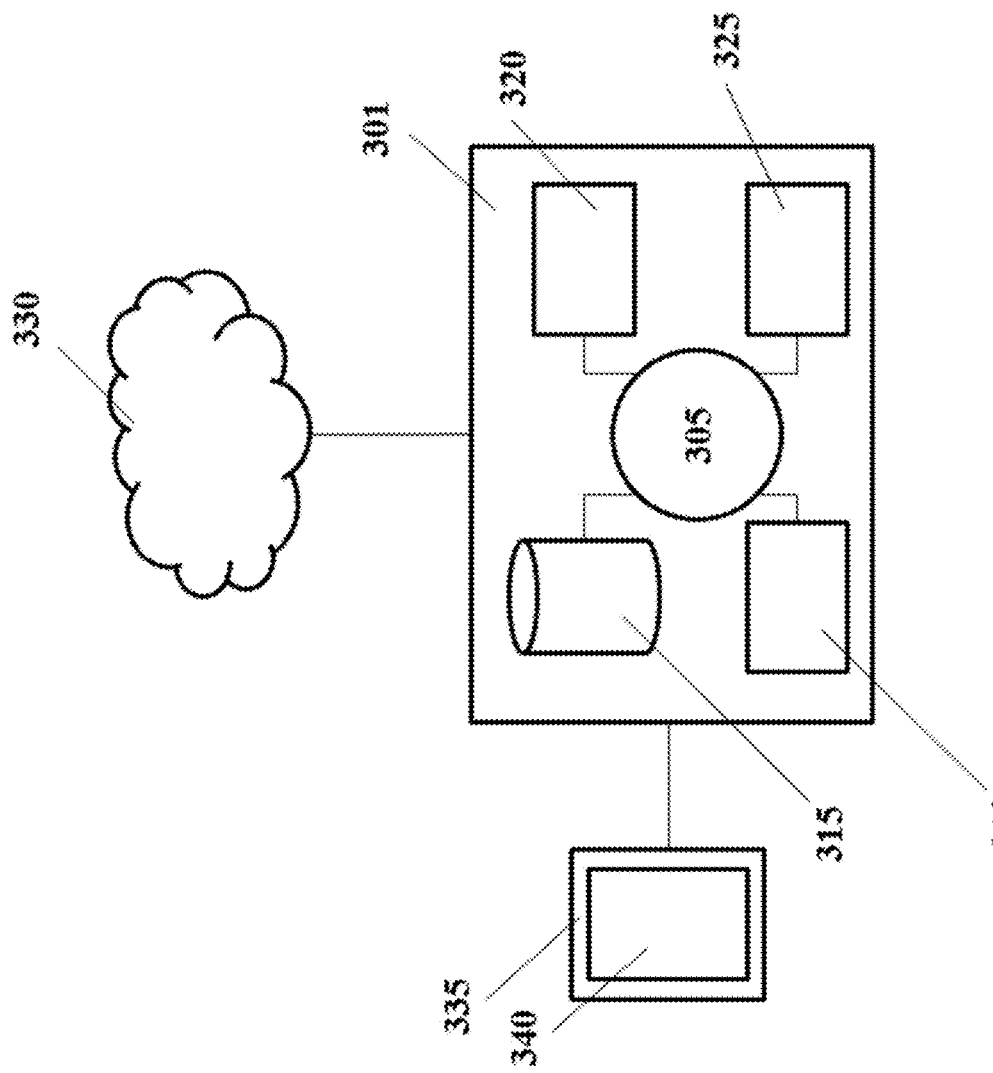
FIG. 3 shows a computer system that is programmed or otherwise configured to implement methods provided herein.

The present disclosure provides computer systems that are programmed to implement methods of the disclosure. FIG. 3 shows a computer system 301 that is programmed or otherwise configured to perform nucleic acid sequencing. The computer system 301 can determine sequence reads based at least in part on intensities of detected optical signals. The computer system 301 can regulate various aspects of the present disclosure, such as, for example, performing nucleic acid sequencing, sequence analysis, and regulating conditions of transient binding and non-transient binding (e.g., incorporation) of nucleotides. The computer system 301 can be an electronic device of a user or a computer system that is remotely located with respect to the electronic device. The electronic device can be a mobile electronic device.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit 315 (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340 for providing, for example, results of nucleic acid sequence and optical signal detection (e.g., sequence reads, intensity maps, etc.). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 305. The algorithm can, for example, implement methods and systems of the present disclosure, such as determine sequence reads based at least in part on intensities of detected optical signals.

EXAMPLES

Example 1: General Synthetic Principles

Certain examples of the following examples illustrate various methods of making linkers and labeled substrates described herein. It is understood that one skilled in the art may be able to make these compounds by similar methods or by combining other methods known to one skilled in the art. It is also understood that one skilled in the art would be able to make other compounds in a similar manner as described below by using the appropriate starting materials and modifying synthetic routes as needed. In general, starting materials and reagents can be obtained from commercial vendors or synthesized according to sources known to those skilled in the art or prepared as described herein.

Unless otherwise noted, reagents and solvents used in synthetic methods described herein are obtained from commercial suppliers. Anhydrous solvents and oven-dried glassware may be used for synthetic transformations sensitive to moisture and/or oxygen. Yields may not be optimized. Reaction times may be approximate and may not be optimized. Materials and instrumentation used in synthetic procedures may be substituted with appropriate alternatives. Column chromatography and thin layer chromatography (TLC) may be performed on reverse-phase silica gel unless otherwise noted. Nuclear magnetic resonance (NMR) and mass spectra may be obtained to characterize reaction products and/or monitor reaction progress.

Example 2: A Structure of a Labeling Reagent

Described herein is an example of a semi-rigid, water-soluble linker of a defined molecular weight that can efficiently accomplish a dye-dye or dye-quencher separation. A semi-rigid structure can be achieved through a series of linked, aromatic or non-aromatic ring systems connected by zero or one linkages with $sp^3$ bonding, and zero or more sp or $sp^2$ bonds. Water-solubility can be achieved with the inclusion (e.g., in each subunit) of at least one of the moieties selected from the group: hydroxyl, pyridinium, imidazolium, sulfonate, amino, thiol, carboxyl, and quaternary ammonium. A linker can be a hetero- or homobi-(or tri-)functional reagent that allows attachment of a dye (e.g., fluorescent dye) at one end and a biological ligand (e.g., a nucleotide) at the other end. An example of a general formula for such a linker is shown below:

$$\left[ R^1 \underset{(CH_n)_q}{\diagup} \overset{R^3}{\underset{\diagdown}{\bigcirc}} \underset{(CH_2)_m}{\diagdown} R^2 \right]_p$$

in which p is a number of repeating units selected from 1-100; each $R^3$ is a water-soluble moiety independently selected from, for example, pyridinium and sulfonate; $R^1$ and $R^2$ are attachment groups such as amino and carboxy moieties; each n is independently 1 or 2; each m is independently selected from 1 and 2; and each q is independently selected from 4-8. In the structure above, m represents the number of $sp^3$ carbons linking ring moieties to one another. A ring moiety may be an aliphatic or an aromatic ring.

Multiple such subunits may be connected to one another. For example, a linker may be represented by the below formula:

$$\left[ R^1 \underset{(CH_n)_q}{\diagup} \overset{R^3}{\underset{\diagdown}{\bigcirc}} \underset{(CH_2)_m}{\diagdown} \right]_p \left[ \underset{(CH_i)_j}{\diagup} \overset{R^4}{\underset{\diagdown}{\bigcirc}} \underset{(CH_2)_k}{\diagdown} R^2 \right]_r$$

in which p and r are each a number of repeating units independently selected from 1-100; each $R^3$ and $R^4$ is a water-soluble moiety independently selected from, for example, pyridinium and sulfonate; $R^1$ and $R^2$ are attachment groups such as amino and carboxy moieties; each n and i is independently 1 or 2; each m and k is independently selected from 1 and 2; and each q and j is independently selected from 4-8. In the structure above, m and k represent the number of sp³ carbons linking ring moieties to one another. A ring moiety may be an aliphatic or an aromatic ring. In some cases, ring moieties in the left portion of the structure are aliphatic and ring moieties in the right portion of the structure are aromatic, or vice versa.

Note that the above structures do not capture all embodiments of the disclosure. For example, the linker does not have to be a polymer of "P-repeating" units. Similarly, the water-soluble functional group can be a constituent component of the ring rather than attached to the ring.

Example 3: Synthesis of dGTP-AP-SS-Hyp10-Atto633

Described herein is a method for constructing the labeled nucleotide dGTP-AP-SS-hyp10-Atto633. FIG. 5A illustrates an example method for the synthesis of a fluorescently labeled dGTP reagent. FIG. 5B illustrates the same synthesis with the full structures of the dye and linker. The method involves formation of a covalent linkage between Gly-Hyp10 and the fluorophore Atto633 (process (a)), esterification to couple Atto633-Gly-Hyp10 with pentafluorophenol (process (b)), substitution with the linker molecule epSS (process(c)), esterification to form Atto633-Gly-Hyp10-epSS-PFP (process (d)), and substitution with dGTP to provide the fluorescently labeled nucleotide (process (e)). Details of the synthesis are provided below.

Preparation of Atto633-Gly-Hyp10. (FIG. 5 process (a)) A stock solution of Gly-Hyp10 (also referred to herein as "hyp10") in bicarbonate is prepared by dissolving 25 milligrams (mg) of the 11 amino acid peptide in 500 microliters (μL) of 0.2 molar (M) sodium bicarbonate in a 1.5 milliliter (mL) Eppendorf tube. 7 mg of Atto633-NHS is weighed into another Eppendorf tube and dissolved in 200 μL of dimethylformamide (DMF). A volume of 300 μL of the peptide solution is added to the solution containing Atto633-NHS. The resulting solution is mixed and heated to 50° C. for 20 minutes (min). The extent of the reaction is followed with reverse-phase thin layer chromatography (TLC). A 1 μL aliquot of the reaction solution is removed and dissolved in 40 μL water and spotted on reverse phase TLC. A co-spot with Atto633 acid is included, and Atto633 is also run alone. The plate is eluted with a 2:1 solution of acetonitrile 0.1M triethylammonium acetate (TEAA). Atto633 acid and Atto633-NHS both have an $R_f$ of zero, while Gly-Hyp10 has an $R_f$ of 0.4. The product is purified by injecting the solution onto a C18 reverse phase column using the gradient 20%→50% acetonitrile vs. 0.1M TEAA over 16 minutes at 2.5 mL/min. The desired product is the major product, Atto633-Gly-Hyp10, eluting at 15.2 minutes. The fractions containing the desired material are collected in Eppendorf tubes and dried, yielding a blue solid. A major peak was observed on ESI mass spec: m/z calculated for $C_{87}H_{115}N_{14}O_{24}^+$, $[M]^+=1739.8$; found: 1740.6.

Preparation of Atto633-Gly-Hyp10-PFP. (FIG. 5 process (b)) Atto633-Gly-Hyp10 is suspended in 100 μL DMF in a 1.5 mL Eppendorf tube. Pyridine (20 μL) and pentafluorophenyl trifluoroacetate (PFP-TFA, 20 μL) are added to the tube. The reaction mixture is warmed to 50° C. in a heat block for 20 min. The reaction is monitored by removing 1 μL aliquots and adding to 1 mL of dilute HCl (0.4%). When the reaction is complete the aqueous solution is colorless. After 10 min the dilute HCl solution is light blue. Additional PFP-TFA (30 μL) is added. After another 100 min at 50° C. a retest of precipitation gives a colorless solution. The remaining reaction mixture is precipitated into 1 mL dilute HCl in 20 μL portions. 20 μL is added to 1 mL dilute HCl, the tube spun down, and aqueous solution discarded. The process is repeated until all of the product is precipitated. The residue is thoroughly dried. After drying, the solid is washed twice with 1 mL methyl tert-butyl ether (MTBE). The product is a dark blue powder. The product gives a major peak on electrospray ionization (ESI)-mass spectrometry (MS): m/z calculated for $C_{93}H_{115}F_5N_{14}O_{24}^{2+}$, $[M+H]^{2+}=1906.8/2=953.4$; found: 953.4.

Preparation of Atto633-Gly-Hyp10-epSS. (FIG. 5 process (c)) Atto633-Gly-Hyp10-PFP (1.6 micromoles (μmol)) is dissolved in 100 μL DMF in an Eppendorf tube. A solution of aminoethyl-SS-propionic acid (Broadpharm; 6 mg in 200 μL 0.1 M bicarbonate) is mixed with the Atto633-gly-hyp10-PFP and heated to 50° C. in a heat block for 20 min. Atto633-Gly-Hyp10-epSS is purified from the resulting reaction mixture by reverse phase HPLC using a gradient of 20%-50% acetonitrile over 16 min. Atto633-Gly-Hyp10 elutes at 15 min and Atto633-Gly-Hyp10-epSS elutes at 15.6 min. The fractions containing the product, Atto633-Gly-Hyp10-epSS, are combined and dried. The product has a major peak on ESI-MS: m/z calculated for $C_{92}H_{124}N_{15}O_{25}S_2^+$, $[M]^+=1902.8$; Found: 1902.6.

Preparation of Atto633-Gly-Hyp10-epSS-PFP. (FIG. 5 process (d)) Atto633-Gly-Hyp10-epSS is dissolved in 100 μL DMF in an Eppendorf tube. Pyridine (20 μL) and PFP-TFA (20 μL) are added and the mixture is heated to 50° C. in a heat block for 20 min. A test aliquot (1 μL) in dilute HCl gives a colorless solution and a blue precipitate. The reaction is precipitated in 20 μL aliquots in 1 mL dilute HCl, the tube spun down, and the aqueous solution discarded. The process is repeated until all of the PFP ester is precipitated. The residue is thoroughly dried under vacuum and washed with MTBE.

Preparation of dGTP-AP-SS-Atto633. (FIG. 5 process (e)) A solution of aminopropargyl dGTP (Trilink; 1 μmol in 100 μL of 0.2 M bicarbonate) is added to 50 μL of a DMF solution comprising Atto633-gly-hyp10-epSS-PFP. The mixture is heated to 50° C. for 10 min. The product, dGTP-AP-epSS-Atto633, is purified by reverse-phase HPLC using a gradient of 20%→50% acetonitrile 16 min. The product elutes at 15.3 min. Preparative HPLC provides 0.65 μmol. The product gives a major peak on ESI-MS: m/z calculated for $C_{106}H_{139}N_{20}O_{37}P_3S_2^{2-}$, $[M-H]^{2-}$, 1220.4; found: 1220.6.

While synthesis of dGTP-Atto633-Gly-Hyp0-epSS-PFP is described, a skilled practitioner will recognize that other fluorescently labeled nucleotides can be produced in a similar manner using appropriate starting materials.

Example 4: Synthesis of dCTP-epSS-Atto633 dCTP-SS12-Atto633 can be prepared in manner similar to the method outlined in Example 3. Briefly, Atto633-epSS is prepared (FIG. 6 process (a)) by mixing a 200 μL DMF solution comprising 11 mg Atto633-NHS with a 200 μL aqueous solution comprising 0.2M sodium bicarbonate and 24 mg epSS, heating the resulting mixture to 50° C. for 15 min, purifying Atto633-epSS from the mixture by reverse phase HPLC using a gradient of 40%→60% acetonitrile vs. 0.1 M TEAA over 16 min at 4.5 mL/min, and confirming the product identity with ESI-MS. The product elutes at 7.3 min and the free dye elutes at 6.4 min. The yield is about 80%. The product gives a major peak on ESI-MS: calculated for $C_{40}H_{51}N_4O_4S_2^+$, $[M]+=715.3$; Found $[M]+=715.3$.

Figure 6:
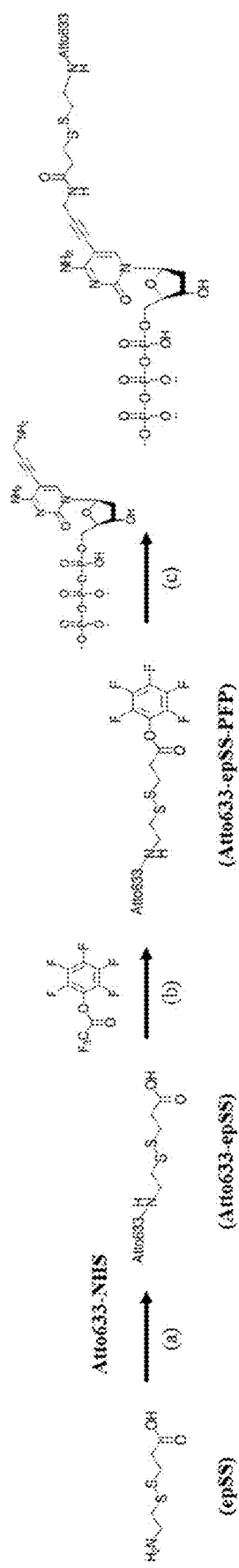
FIG. 6 shows an example method for the preparing a labeled nucleotide comprising dCTP.

Atto633-epSS is then converted to Atto-epSS-PFP (FIG. 6 process (b)) by mixing a solution of Atto633-epSS dissolved in 100 μL DMF, 20 μL pyridine, and 20 μL PFP-TFA; heating the solution at 50° C. for 5 min before adding an additional 20-40 μL PFP-TFA; heating back to 50° C. for 5 min; and precipitating the product in 1 mL of dilute HCl. The product is washed with an additional 1 mL of dilute HCl and the supernatant removed by pipette and evaporation, yielding a blue solid.

dCTP-epSS-Atto633 is formed by reacting Atto-epSS-PFP with aminopropargyl dCTP (AP-dCTP) (FIG. 6 process (c)). AP-dCTP stock solution (Trilink; 1 μmol) is added to a 100 μL DMF solution comprising 0.2 M sodium bicarbonate and combined with a solution of Atto-epSS-PFP dissolved in 100 μL DMF. The mixture is left to sit overnight. dCTP-epSS-Atto633 is purified from the mixture on a C18 reverse phase column using the gradient 20%→100% acetonitrile vs. 0.1 M TEAA over 16 minutes at 2.5 mL/min. The product elutes at 10.7 min. The fractions including the product are collected and dried. The product gives a major peak on ESI-MS: Calculated m/z for $C_{52}H_{66}N_8O_{16}P_3S_2^-$, $[M]^-=1215.3$; found: 1215.5.

Example 5: Preparation of Dye-Labeled Nucleotides

A set of dye-labeled nucleotides designed for excitation at about 530 nm is prepared. Excitation at 530 nm may be achieved using a green laser, which may be readily available, high-powered, and stable. There are many commercially available fluorescent dyes with excitation at or near 530 nm that are inexpensive and have a variety of properties (hydrophobic, hydrophilic, positively charged, negatively charged). Synthetic routes to such dyes may be shorter and cheaper than those for longer wavelength dyes. Moreover, certain green dyes may have significantly less self-quenching than red dyes, potentially allowing for the use of higher labeling fractions (e.g., as described herein).

A viable reagent set for use in, e.g., a sequencing application consists of each of four canonical nucleotides or analogs thereof with cleavable green dyes that perform well in sequencing. An optimal set may be prepared by varying each component of a labeled nucleotide structure to obtain an array of candidate labeled nucleotides with varying properties. The resultant nucleotides are evaluated (e.g., as described below), and certain labeled nucleotides are optimized for concentration and labeling fraction (the ratio of labeled to unlabeled nucleotide in a flow).

Figure 7:
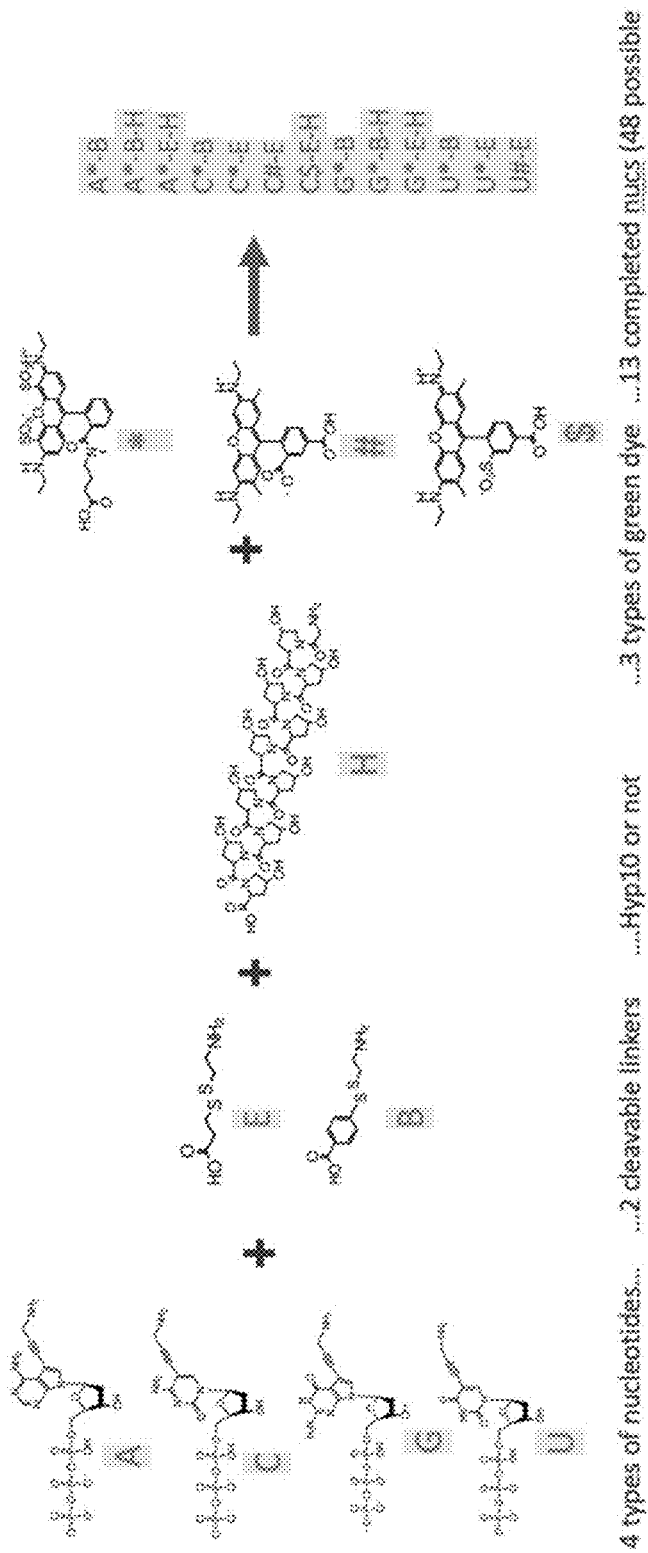
FIG. 7 shows components used to construct dye-labeled nucleotides for excitation at about 530 nm.

FIG. 7 shows a variety of components used in the construction of candidate labeled nucleotides. Each of four propargylamino functionalized nucleotides (A, C, G, and U) can be modified with one of two cleavable linkers, E and B; a hydroxyproline linker (hyp10) or not; and one of three fluorescent dyes, *, #, and $. Using these components, there are 48 possible nucleotide variations. The labeled nucleotides may be prepared according to the synthetic route and principles described herein. An example synthesis of the G*-B-H labeled nucleotide is described in Example 6.

Example 6: Synthesis of G*-B-H Labeled Nucleotide

Figure 8:
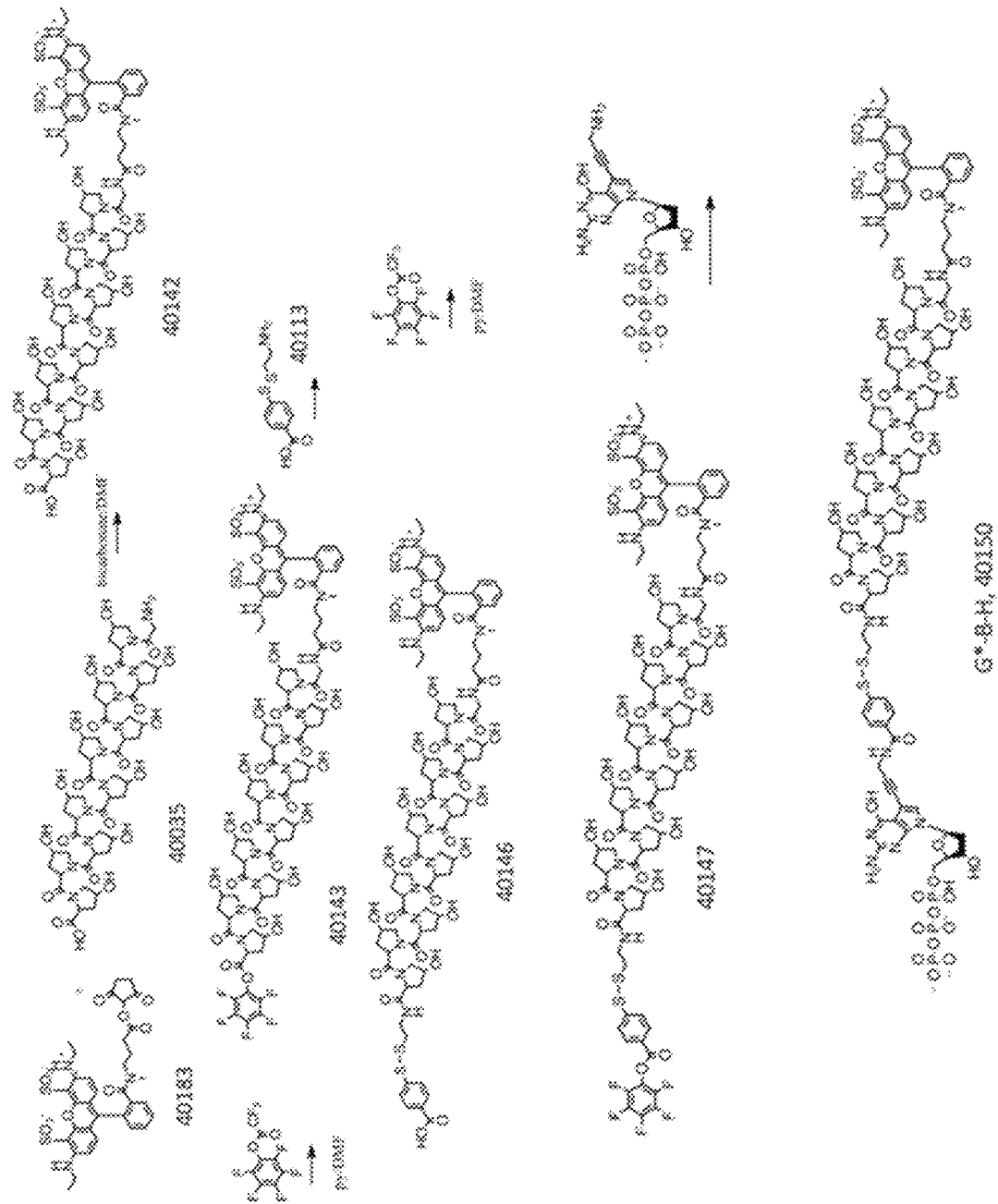
FIG. 8 shows an example method for preparing a labeled nucleotide comprising a guanine analog.

A synthetic method for preparing G*-B-H (see Example 5) is shown in FIG. 8. Similar methods may be used to prepare other labeled nucleotides described in Example 5 and elsewhere herein. As the components used include amino acids, there are multiple routes to the final product. Synthetic considerations include the tendency for hydrolysis of the triphosphate (to the diphosphate and monophosphates) under heat or acidic conditions, the tendency for disulfide to decompose in the presence of triethylamine and ammonia, preventing the use of acid-labile protecting groups, and preventing the use of trifluoroacetamide or FMOC protecting groups.

Preparation of PN 40142. A solution of Atto 532 succinimidyl ester (Atto-tec, PN 40183; 5 mg=4.6 μmol) in 100 μL of DMF is mixed with gly-hyp-hyp-hyp-hyp-hyp-hyp-hyp-hyp-hyp-hyp (custom synthesis from Genscript, PN 40035; 8.5 mg=7 μmol) in 170 μL 0.1 M bicarbonate in a 1.5 mL Eppendorf tube. The reaction is purified on a Phenomenex reverse phase C18 semi-prep column (Gemini 5 μM C18, 250×10 mm) using a gradient of 10%→40% acetonitrile vs. 0.1 M triethylammonium acetate over 16 minutes. The fractions containing product 40142 are combined and concentrated to dryness. The yield is determined by diluting a fraction and measuring the optical density (OD) at 633 nm and using an extinction coefficient for the dye of 130,000 $cm^{-1}M^{-1}$. The yield is 50%. The structure is confirmed by mass spectrometry in negative ion mode: m/z calculated for $C_{81}H_{103}N_{14}O_{31}S_2^-$, 1831.6; found: 1831.8.

Preparation of PN 40143. PN 40142 (4 μmol) is suspended in 100 μL DMF in a 1.5 mL eppendorf tube. Pyridine (20 μL) and pentafluorophenyl trifluoroacetate (20 μL) are added to the DMF solution and heated to 50° C. for five minutes. A portion (1 μL) of the reaction mixture is precipitated into 0.4% HCl; the aqueous solution remains colorless, indicating complete conversion to the active, pentafluorophenyl ester. The remainder of the reaction is precipitated into the dilute acidic solution and the aqueous solution pipetted off. The residue is washed with hexane and dried to a highly colored solid (PN 40143)

Preparation of PN 40146. PN 40143 is dissolved in 100 μL DMF and mixed with disulfide PN 40113 (5 mg, 20 μmol) in DMF. Diisopropylethylamine (5 μL) is added to the mixture. The mixture is purified on reverse phase HPLC using a gradient of 20%→50% acetonitrile vs. 0.1 M TEAA over 16 minutes. Two dye-colored fractions are obtained at 8.8 min and 9.5 min. The fraction at 9.5 min is identified by mass spectrometry to be the desired product: m/z calculated for $C_{90}H_{111}N_{15}O_{32}S_4^{2-}$, $[M-H]^{2-}$, 1020.84; found: 1021.1.

Preparation of PN 40147. PN 40146 is suspended in 100 μL DMF in a 1.5 mL eppendorf tube. Pyridine (20 μL) and pentafluorophenyl trifluoroacetate (20 μL) are added to the DMF solution and heated to 50° C. for five minutes. A portion (1 μL) of the reaction mixture is precipitated into 0.4% HCl; the aqueous solution remains colorless, indicating complete conversion to the active, pentafluorophenyl ester. The remainder of the reaction is precipitated into the dilute acidic solution and the aqueous solution pipetted off. The residue is washed with hexane and dried to a highly colored solid (PN 40147)

Preparation of PN 40150. PN 40147 is dissolved in 50 μL DMF in a 1.5 mL eppendorf tube. A solution of 0.5 μmol 7-deaza-7-propargylamino-2'-deoxyguanosine-5'-triphosphate in 50 μL 1 M bicarbonate is prepared and added to the tube. After remaining overnight at 4° C. the product is purified on HPLC; the fraction at 12 min using a 20%-50% acetonitrile vs. 0.1 M TEAA gradient over 16 minutes contains the desired product: m/z calculated for $C_{104}H_{129}N_{20}O_{44}P_3S_4^{2-}$, $[M-H]^{2-}$, 1291.33; found: 1292.4.

Example 7: Evaluation of Dye-Labeled Nucleotides

Figure 9:
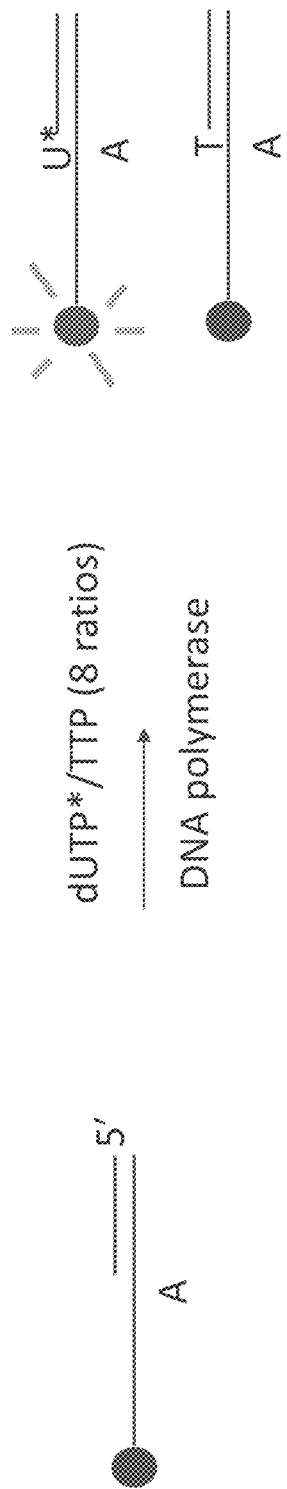
FIG. 9 shows a schematic of a bead-based assay for evaluating labeled nucleotides.

A bead-based assay is used to evaluate dye-labeled nucleotides of Example 5. A streptavidin bead is prepared with a 5'-biotinylated template strand annealed to a primer strand. The primer strand is designed so that the next cognate base incorporated by a DNA polymerase is a thymidine. A DNA polymerase is bound to the bead complex. Various mixtures containing different ratios of the dye-labeled nucleotide (dUTP*) and the natural base (TTP) is then presented to the beads. After washing away excess reagent, the fluorescence of the beads is read on a flow cytometer using the PE channel (excitation=488 nm, emission=580 nm). A schematic of this assay is shown in FIG. 9.

Figure 10:
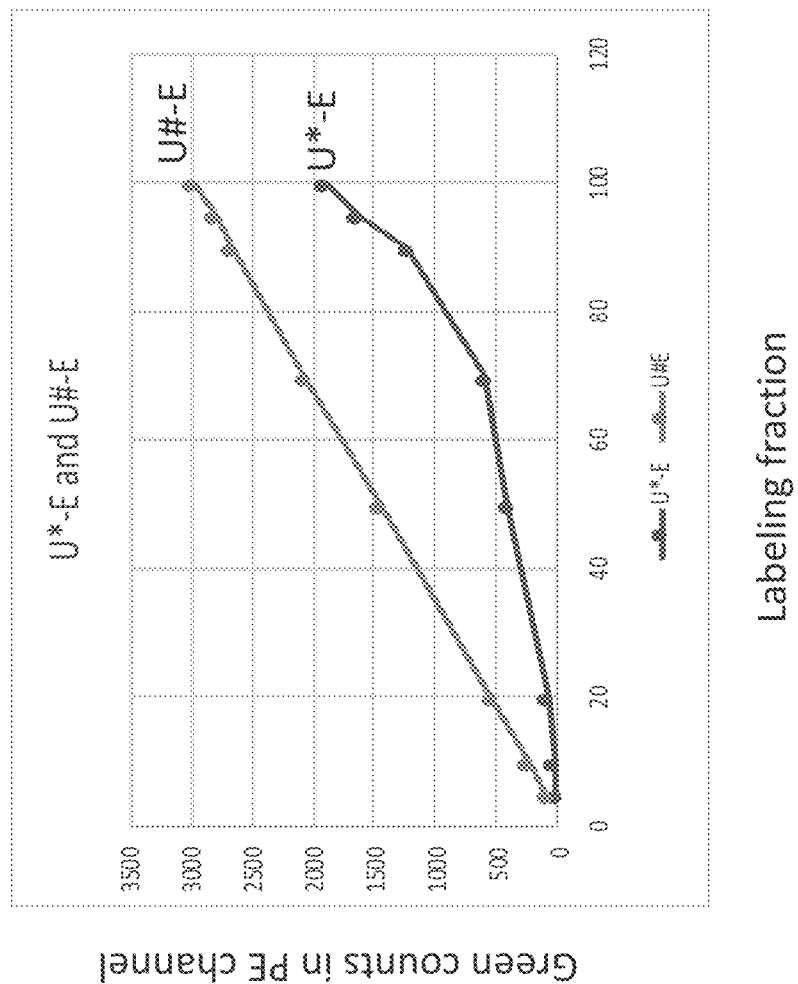
FIG. 10 shows results of a bead-based assay for different labeled dUTPs.

The results of the bead assay for different labeled dUTPs is shown in FIG. 10. The total concentration of the sum of the nucleotides is maintained at 2 µM; a labeling fraction of 10% means 0.2 µM of dUTP* and 1.8 µM of TTP. The behavior for the two nucleotides is noticeably different: U #-E has a "tolerance" of about one, meaning that there is no difference in incorporation of the dye-labeled vs the natural nucleotide over all the ratios tested; i.e., a 50% labeling fraction results in 50% of the beads getting labeled. U*-E, on the other hand, has a negative tolerance, meaning that at every ratio it falls below the line drawn between zero and the signal at 100% labeled. A negative tolerance suggests that the dye-label makes the nucleotide a worse substrate than the natural substrate. This result is consistent with the observation that negatively charged dyes such as Atto532 (the dye denoted by U*-E) inhibit incorporation by many polymerases while dyes such as 5-carboxyrhodamine-6G (the dye denoted by U #-E) are zwitterionic and are known to be good substrates.

Figure 11:
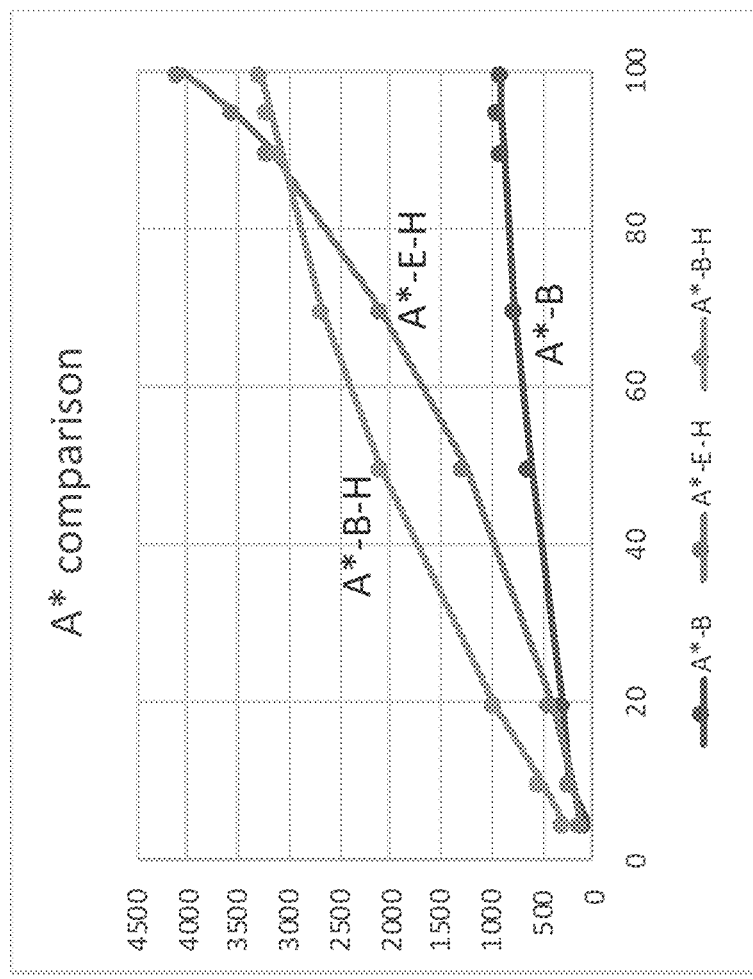
FIG. 11 shows results of a bead-based assay for different labeled dATPs.
Figure 12:
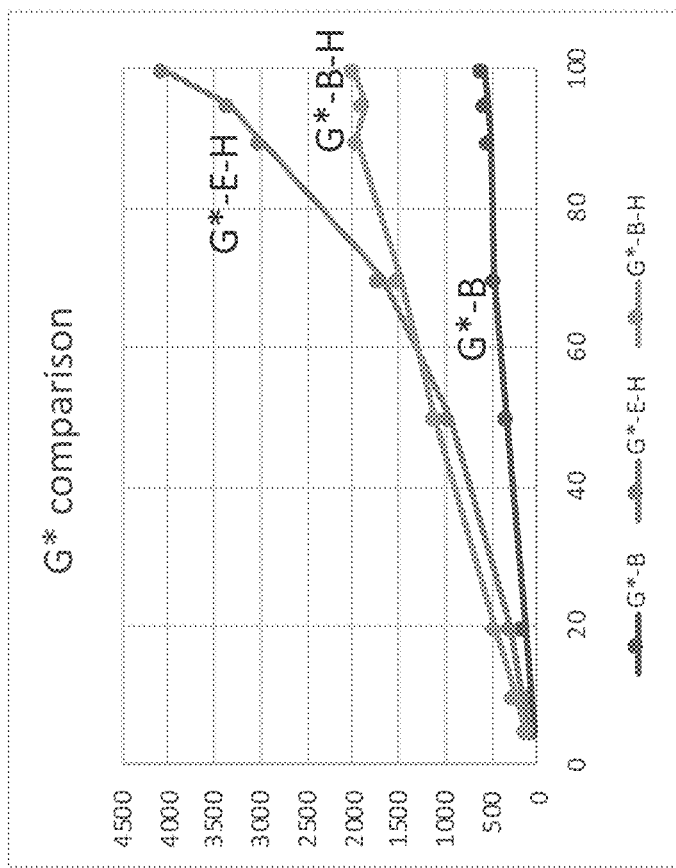
FIG. 12 shows results of a bead-based assay for different labeled dGTPs.

Additional labeled nuclotides are evaluated using a similar assay. FIG. 11 shows the result of the bead assay for labeled dATPs. FIG. 12 shows the result of the bead assay for labeled dGTPs. For labeled dATPs, very low fluorescence is observed at 100% labeling for A*-B compared to A*-B-H and A*-E-H. This indicates that the hydroxyproline linker (H) relieves quenching of the dye by the nucleotide. A similar result is observed for labeled dGTPs. This result is expected for labeled dGTP, as G quenching via photoinduced electron transfer is well known. A quenching effect from the disulfide linker, B, may also contribute to the lower fluorescence observed for labeled dATPs and dGTPs.

Example 8: Sequencing Using Dye-Labeled Nucleotides

A nucleic acid sequencing assay may be used to evaluate dye-labeled nucleotides (e.g., as described herein). An example procedure is shown in FIG. 18.

Sequencing may be performed using an instrument outfitted with a light emitting device (LED) and/or a laser. Each nucleotide evaluated may include a dye that is configured for excitement and emission over similar wavelengths (e.g., all red or all green emission). One or more different nucleotide types may be coupled to different dyes. Sequencing performance may be evaluated based on base calling quality, phase lag, phase lead, and homopolymer completion.

Beads with amplified templates are primed, immobilized on a support, and incubated with a tight-binding DNA polymerase. Beads are then subjected to multiple cycles of sequencing. Each sequencing cycle may comprise incubation with U*/T (a fixed ratio of dye-labeled and natural TTP), a "chase" process (TTP alone), imaging, and a cleavage process (10 mM tris(hydroxypropyl)phosphine (THP)) to release the dye. Each process may have a wash process in between. This process may be repeated for A, C, and G-including nucleotides or nucleotide analogs. This sequencing procedure may effectively identify homopolymeric regions of at least 2, 3, 4, 5, 6, 7, 8, or more nucleotides.

Sequencing is also evaluated for an all hyp-linker set in which dye-labeled nucleotides including each canonical nucleotide include the hyp10 or hyp20 linker. This evaluation is performed to identify a set where higher fractions may be used with minimal quenching. Higher quenching may lead to higher scarring (e.g., as described herein), which may reduce incorporation efficiency by a polymerase enzyme. However, family B enzymes such as PolD may perform well with scars. Sequencing may be evaluated with 2.5% and 20% labeling fractions with a dye such as Atto633.

Figure 19:
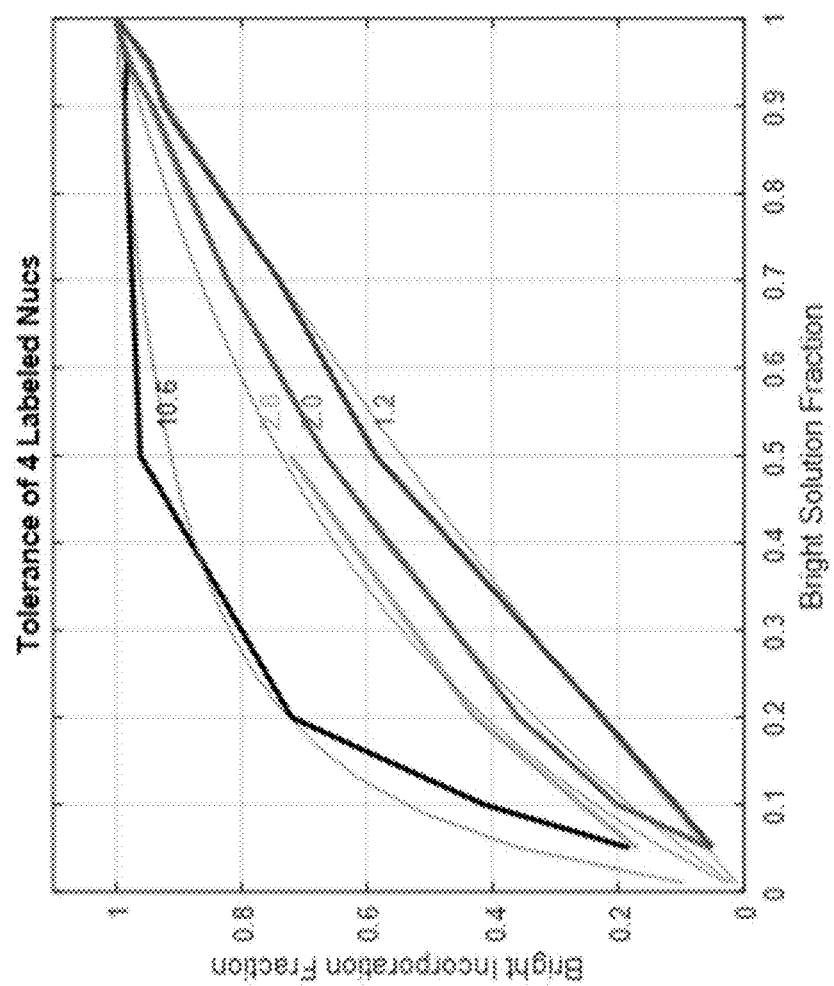
FIG. 19 shows tolerances of different labeled nucleotides.

Sequencing may be used to evaluate the tolerance for various labeled nucleotides. FIG. 19 shows normalized bead data for nucleotides labeled with a red-emitting dye. Bright solution fraction ($b_f$) is plotted against bright incorporation fraction ($b_i$). The curves are fitted to the following equation:

$$b_i = \frac{tol(b_f/d_f)}{1+tol(b_f/d_f)}$$

in which $d_f$ is the dark solution fraction. In FIG. 19, the calculated tolerances are 10.6 for G*, 2.8 for A*, 2.0 for U*, and 1.2 for C*. The positive tolerance numbers indicate that at 50% labeling fraction, more than 50% is labeled. Reagents with a tolerance of 1 may have the least "context" in sequencing. Reagents with a very negative tolerance (e.g., tolerance<<1) may have issues with uniform incorporation across a plurality of templates coupled to a support because they must be used at such low concentrations that they may fall below saturation and be consumed at an uneven rate.

Example 9: Dye-Labeled Nucleotides Including Guanine or Analogs Thereof

Nucleotides including guanine or analogs thereof may perform more poorly in sequencing applications (e.g., as described herein) in base-calling accuracy. This may be related to photoinduced electron transfer from the nucleobase to a dye linked to the nucleobase, which may quench signal emitted by the dye and thus less dynamic range of signal. Accordingly, various dye-labeled nucleotides including guanine or analogs thereof are prepared and evaluated as provided herein. Examples of such dye-labeled nucleotides include:

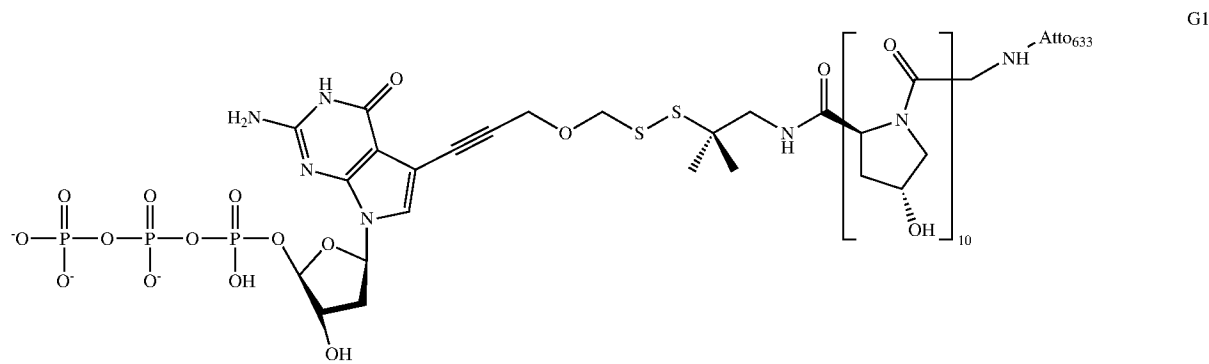

G1

-continued
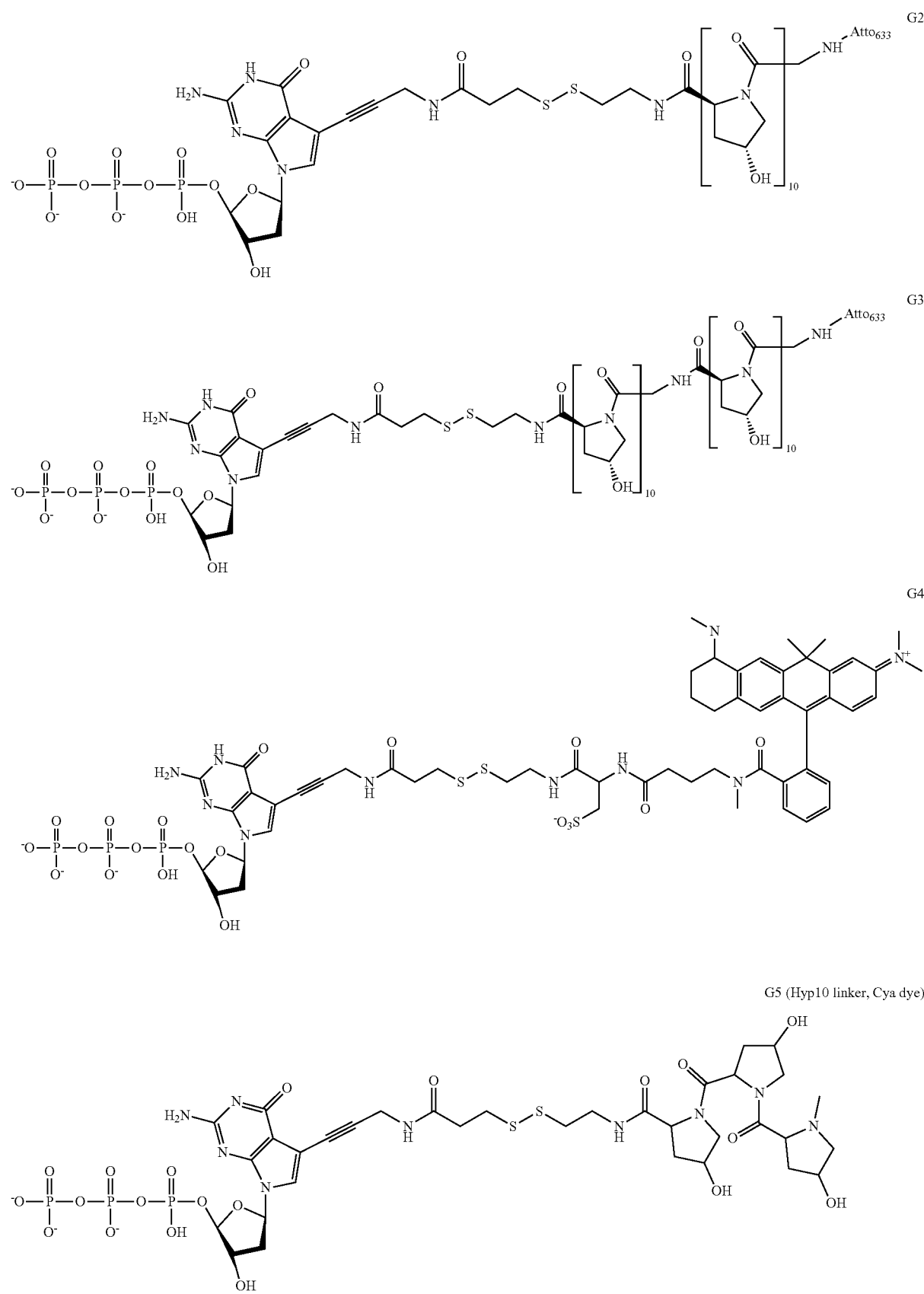

-continued

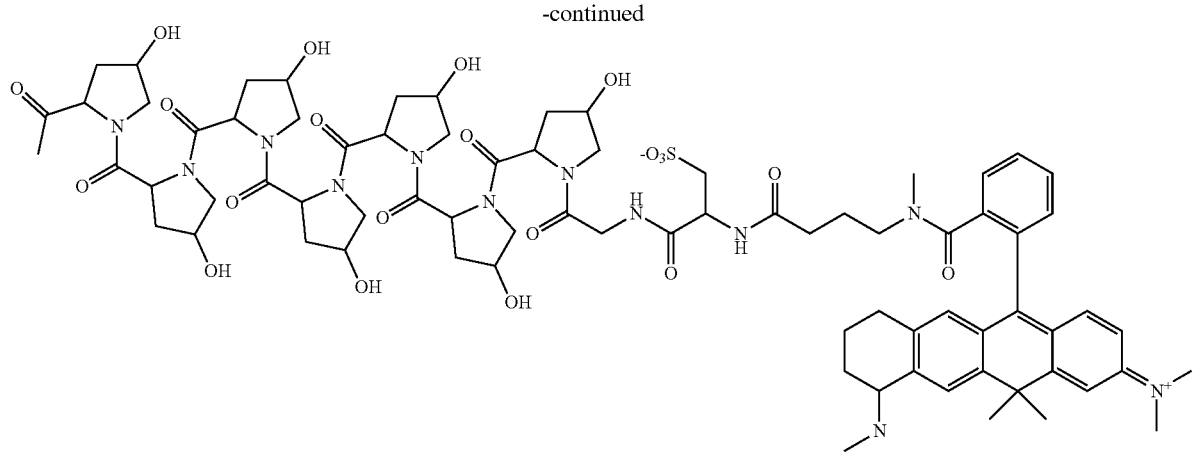

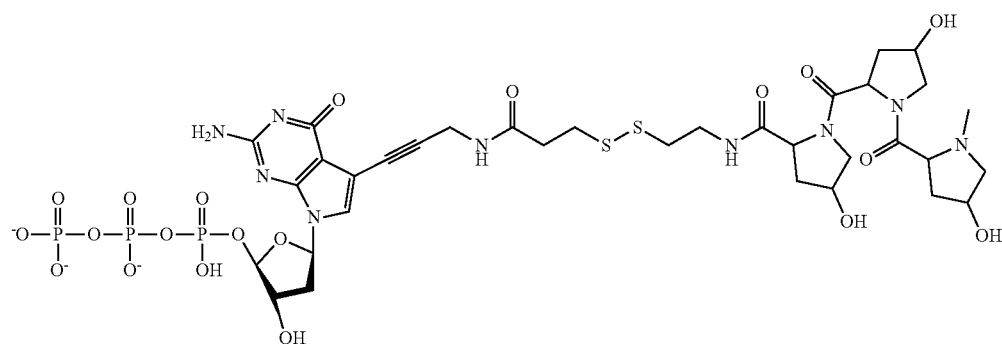

G6 (Hyp10 linker, Cya2 dye)

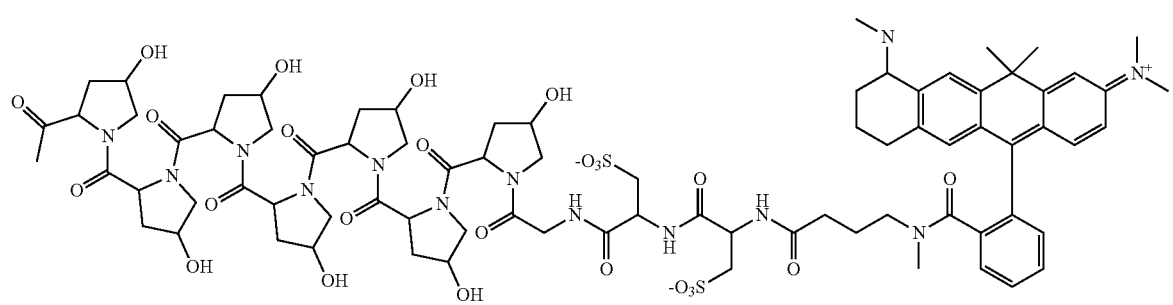

Figure 13A:
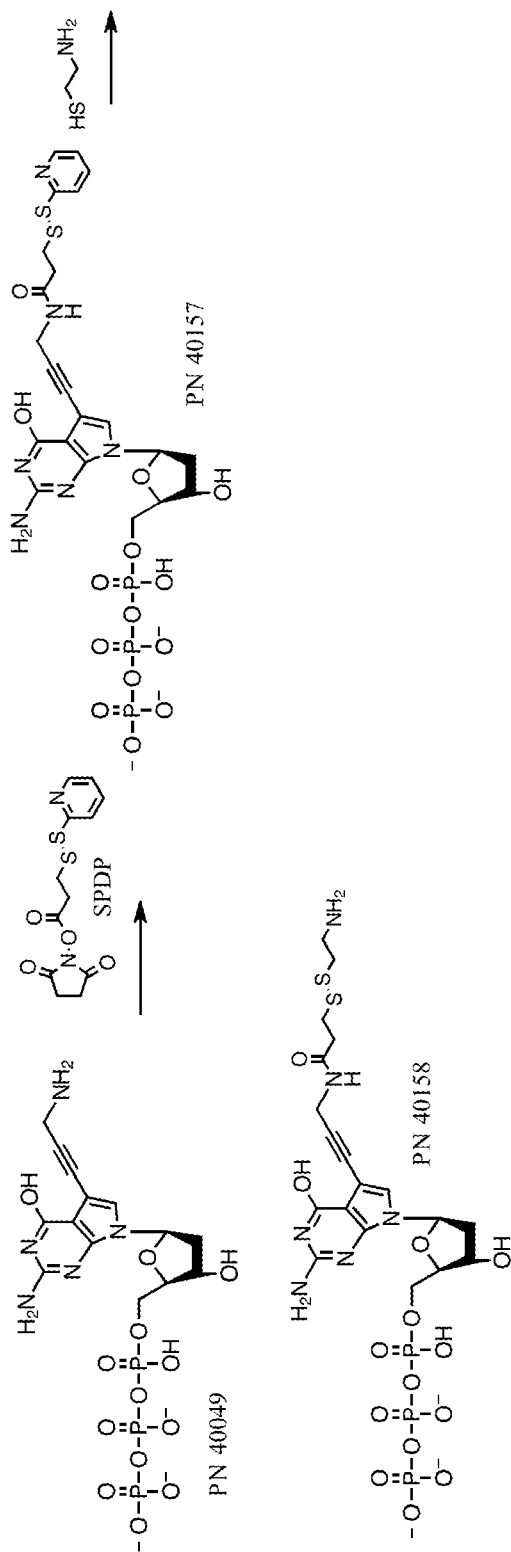
FIGS. 13A-13C show an example method for preparing a labeled nucleotide comprising a guanine analog.
Figure 13B:
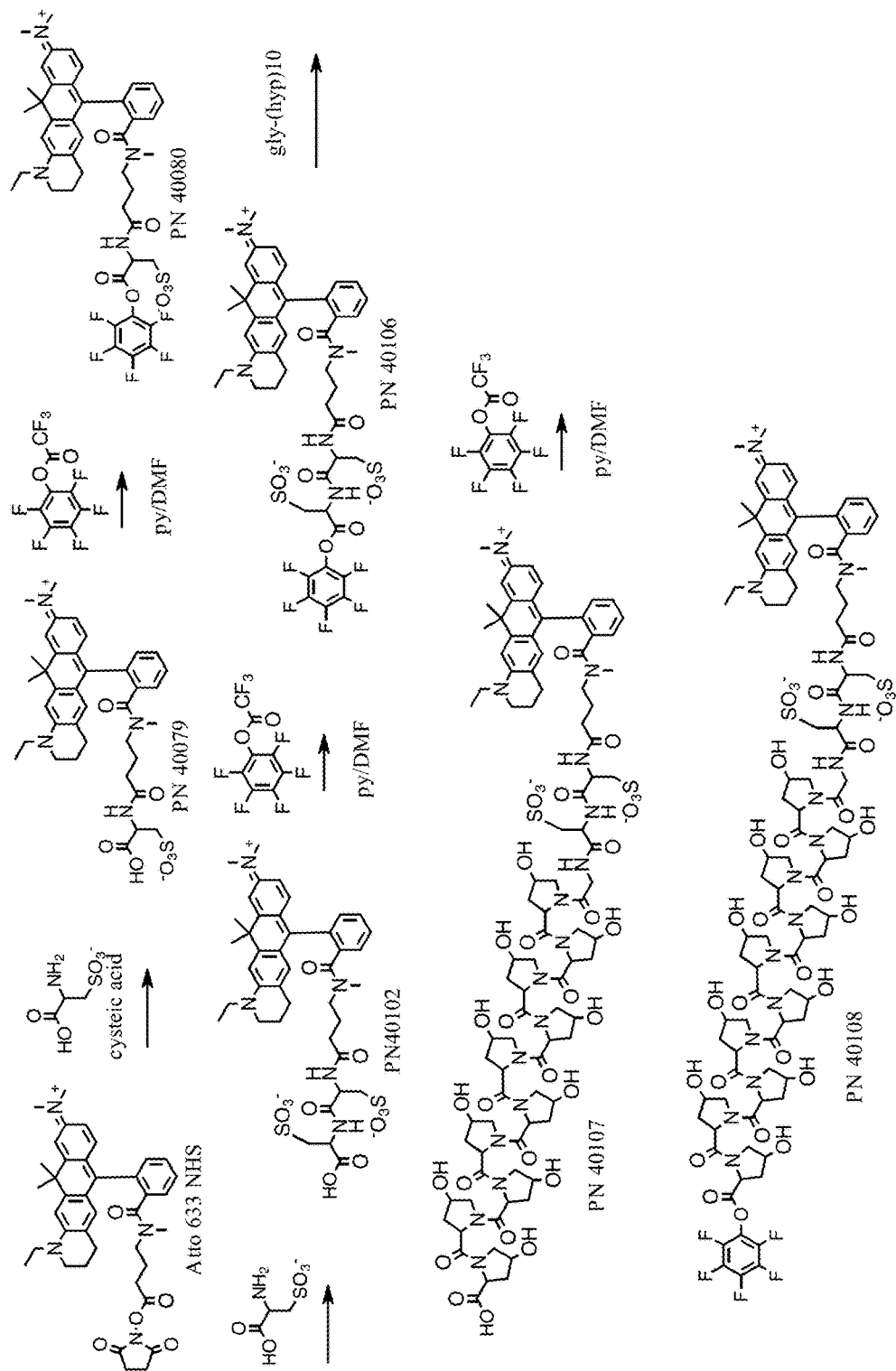
Figure 13C:
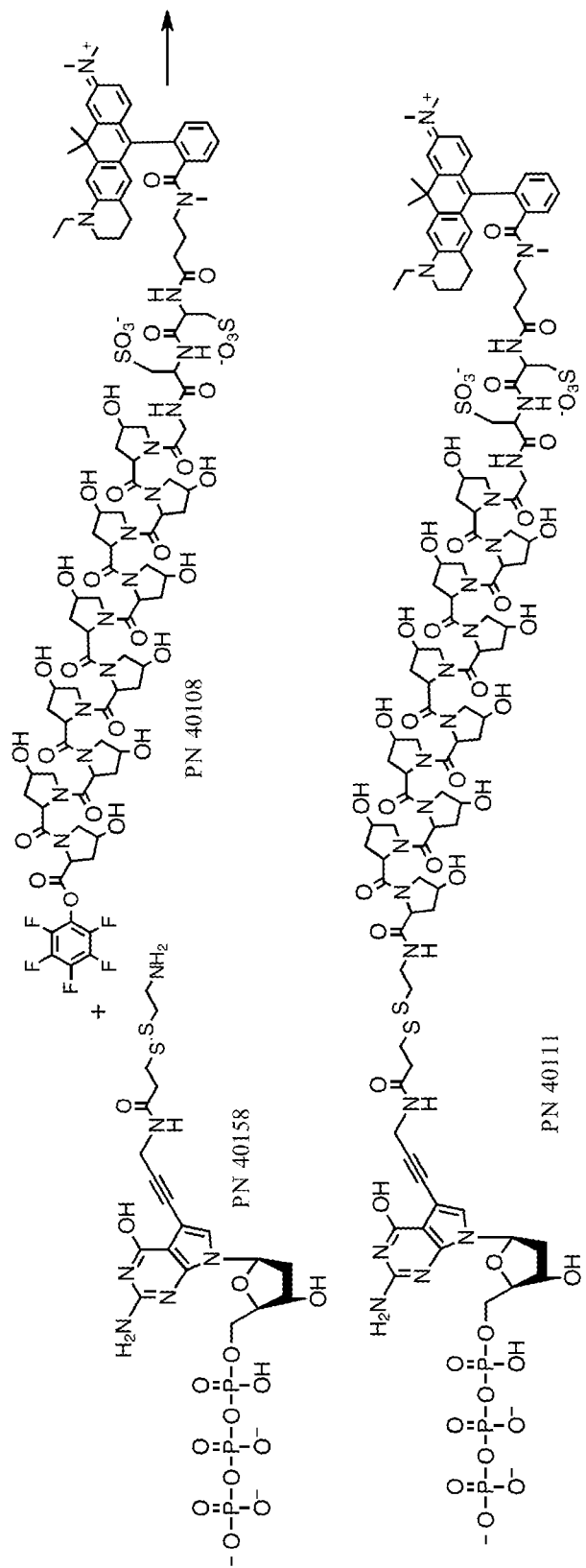

Several of the structures shown above include the hyp10 linker which includes the sequence Gly-Hyp-Hyp-Hyp-Hyp-Hyp-Hyp-Hyp-Hyp-Hyp-Hyp from the N-terminal end. G4, which lacked the hyp10 linker, is highly quenched. The remaining dye-labeled nucleotides are evaluated in a sequencing assay, as described herein. Of the structures shown, G6 provides the highest accuracy. A synthetic route for preparation of G6 is shown in FIGS. 13A-13C.

Example 10: Preparation of Dye-Labeled Nucleotides

A dye-labeled nucleotide may include one or more amino acids. As described above, diamines and diacids may be used to construct amino acids. A dye-labeled nucleotide may include two or more of a given amino acid as a repeating unit. An example of a dye-labeled nucleotide including two repeating units of an amino acid is shown below:

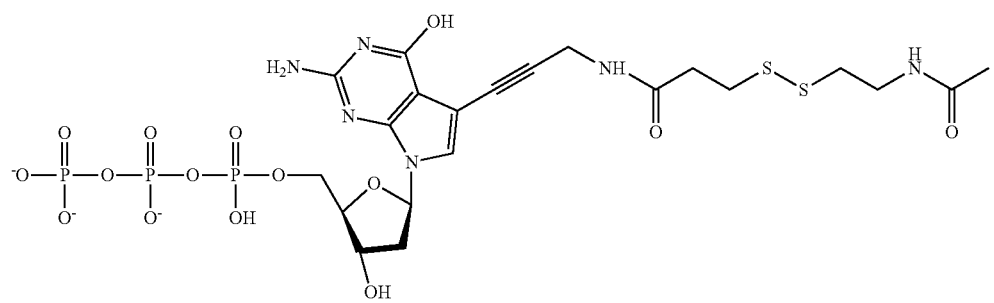

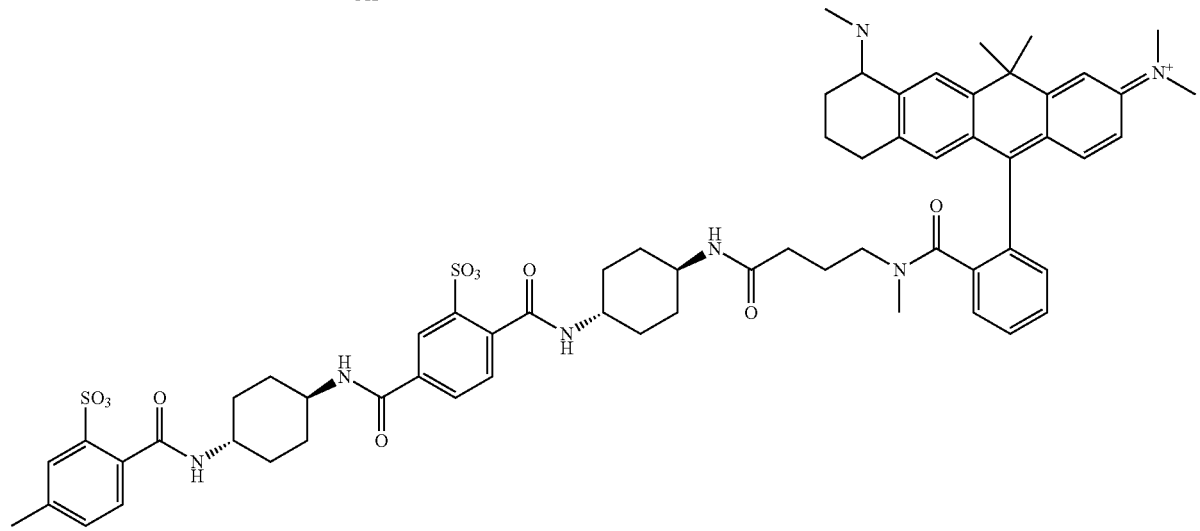

Figure 14A:
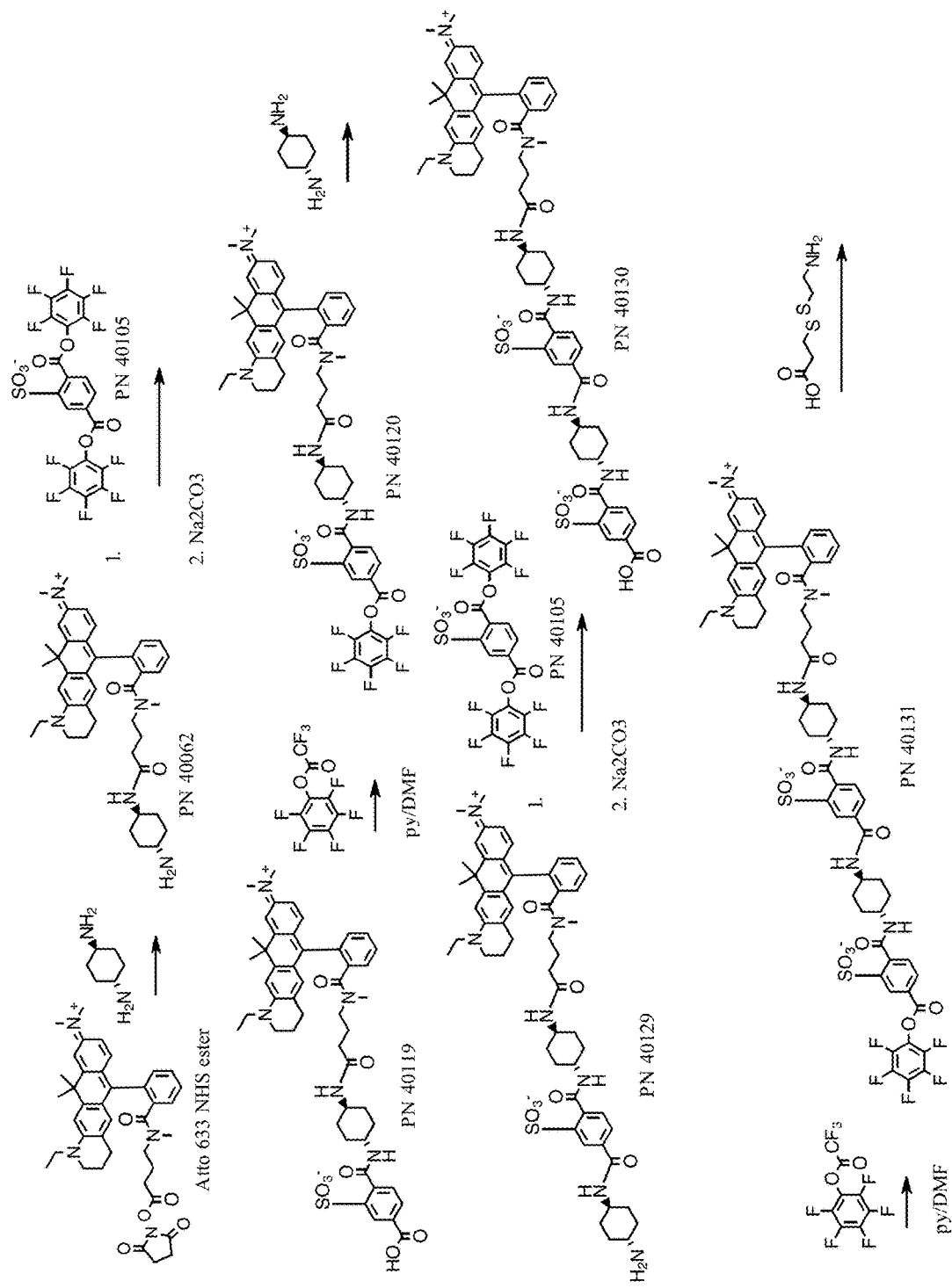
FIGS. 14A and 14B show an example method for preparing a labeled nucleotide comprising repeating units of an amino acid.
Figure 14B:
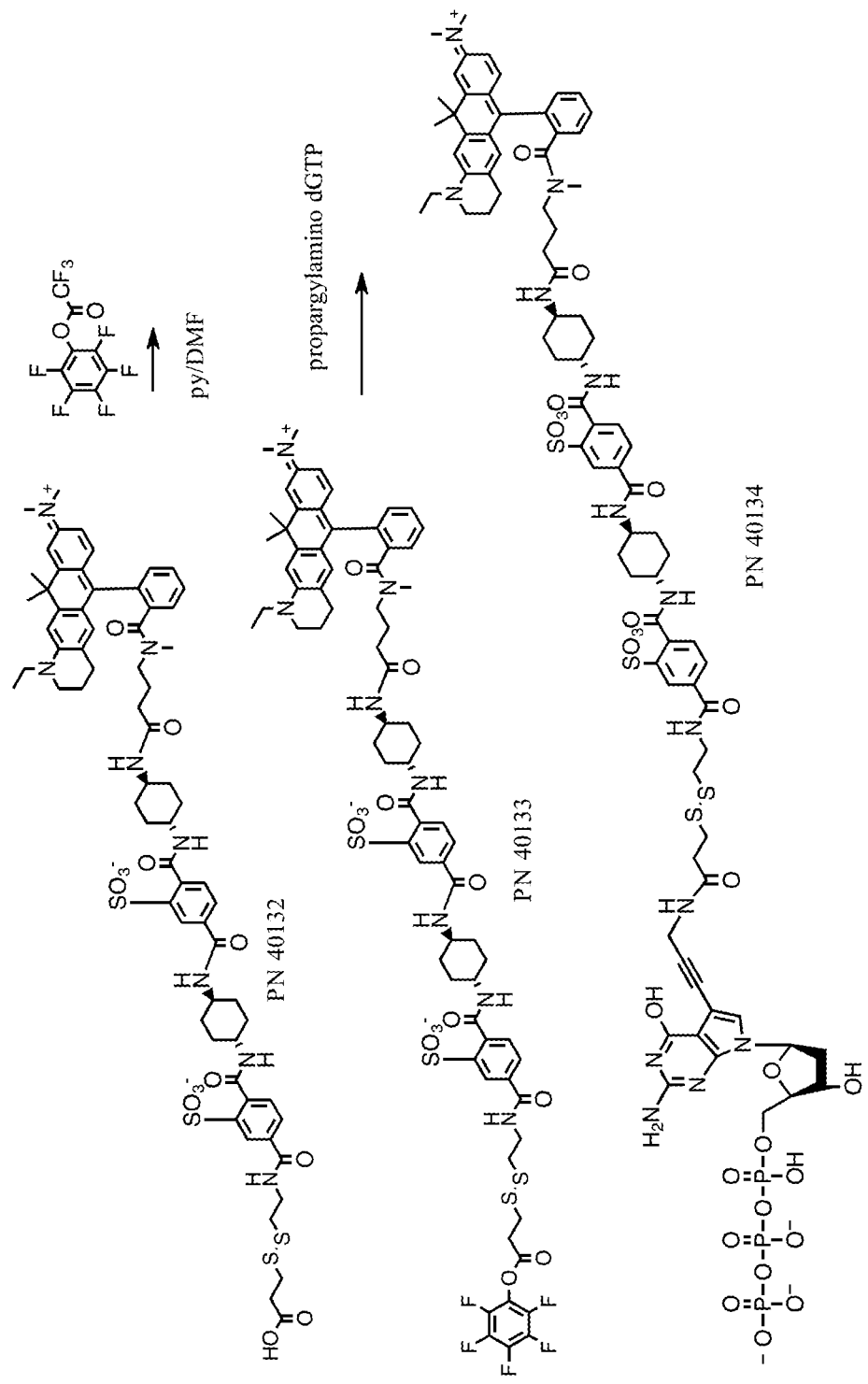

FIGS. 14A and 14B show a synthetic route for preparation of the dye-labeled nucleotide shown above. The composition of each intermediate is confirmed by mass spectrometry. The dye-labeled nucleotide is evaluated in a bead assay, as described in Example 7. The linker provides a G* that is less bright than G*s with polyhydroxyproline linkers, but is more efficient in reducing quenching than a G* without a linker.

Example 11: Evaluation of Quenching

The dye-labeled nucleotides provided herein may improve quenching between nucleobases and the dyes to which they are attached and/or between dyes in a nucleic acid molecule (e.g., a growing nucleic acid strand), such as in a homopolymeric region of a nucleic acid molecule. Quenching may be evaluated in an enzyme-independent manner.

Figure 15:
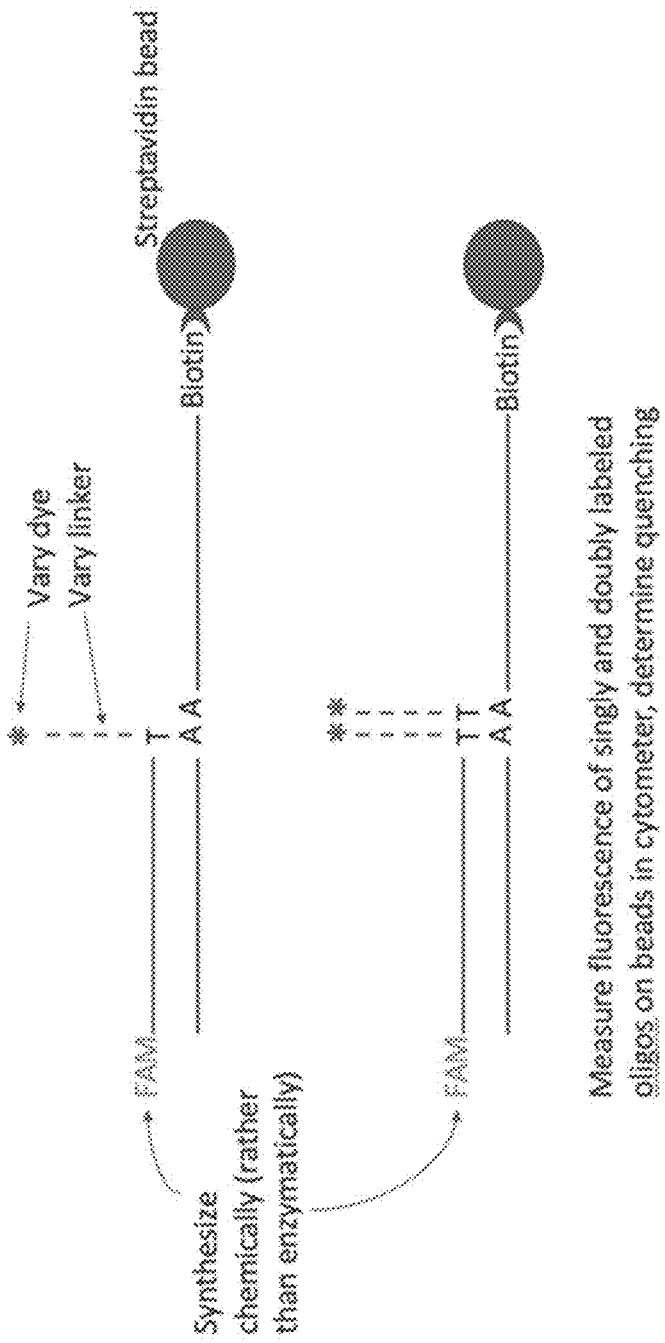
FIG. 15 shows a schematic of an assay for evaluating quenching.

FIG. 15 shows a schematic for evaluating quenching. Synthetic oligos are constructed with one or two "linker arm nucleotides". Linker arm nucleotides are thymidine analogs with a linker arm containing a primary amine. The oligonucleotide containing the linker arm nucleotide can be labeled with linkers and dyes and HPLC purified. The advantage of using the bead-labeled assay is that exact quantitation of the reagents is not necessary; a large excess can be used in each step and the beads washed, ensuring that only stoichiometric amounts of oligonucleotides are bound to the template. Each dye-linker is put on both oligonucleotides. The beads are measured on the flow cytometer in the APC (red) channel. The percent quenching is determined by the formula: % quenching=$100\times(1-Fl_{bis}/(2*Fl_{mono}))$.

Figure 16:
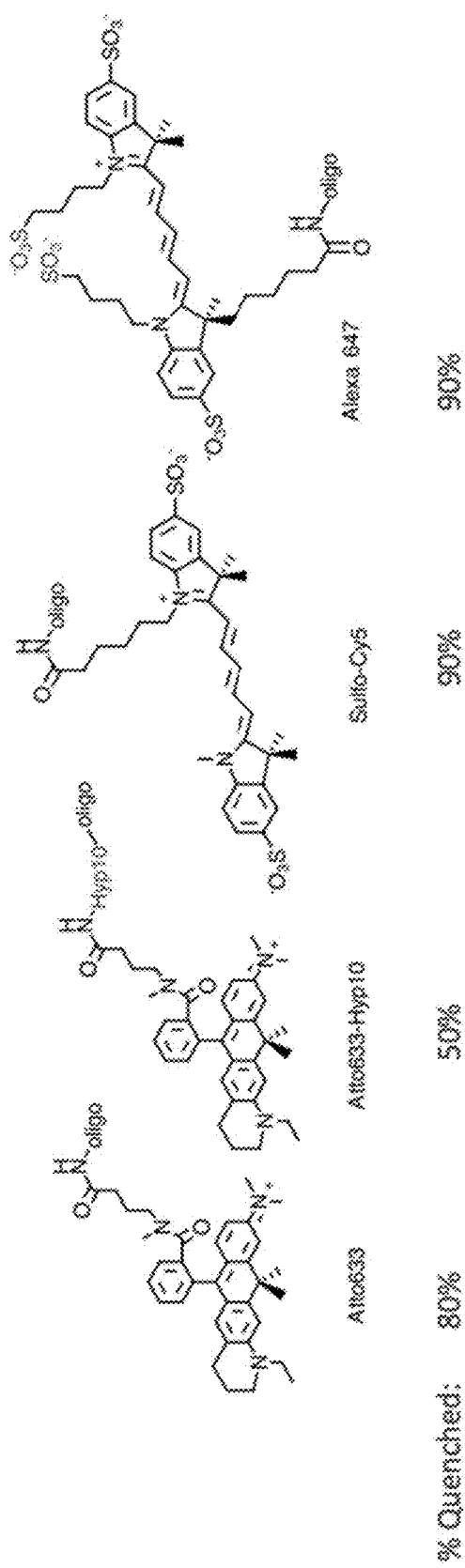
FIG. 16 shows quenching results for red dye linkers.
Figure 17:
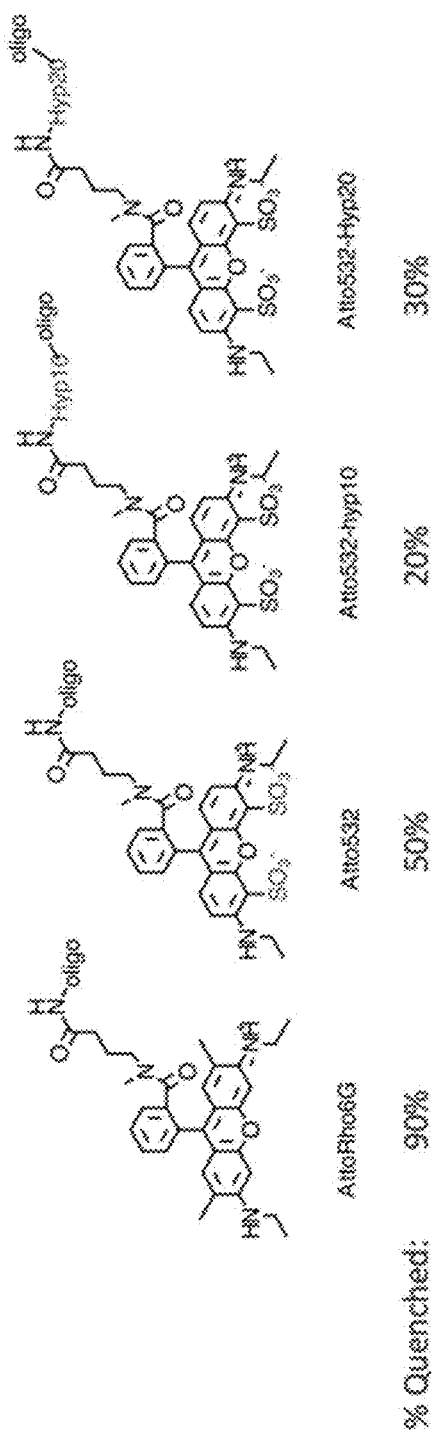
FIG. 17 shows quenching results for green dye linkers.

FIGS. 16 and 17 show quenching results for red dye linkers (FIG. 16) and green dye linkers (FIG. 17). The results show that the nature of the dye affects quenching. Negative charge (see Atto532 vs AttoRho6G) can improve quenching but if the dye is extremely large and flat (see Cy5, Alexa 647) quenching may not be improved. The hyp10 or hyp20 linkers improve quenching. As shown in FIG. 16, hyp10 improves quenching with Atto633, and cyanine dyes quench even with four sulfonic acid groups. As shown in FIG. 17, sulfonic acid groups on Atto532 improve quenching, and the combination of Atto532 and hyp10 also improves quenching.

Example 12: Interrogation of Homopolymers

Figure 20A:
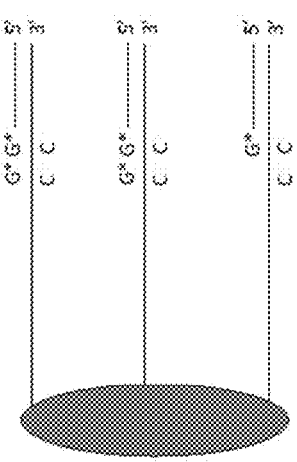
FIGS. 20A and 20B show examples of constructs including homopolymeric regions.
Figure 20B:
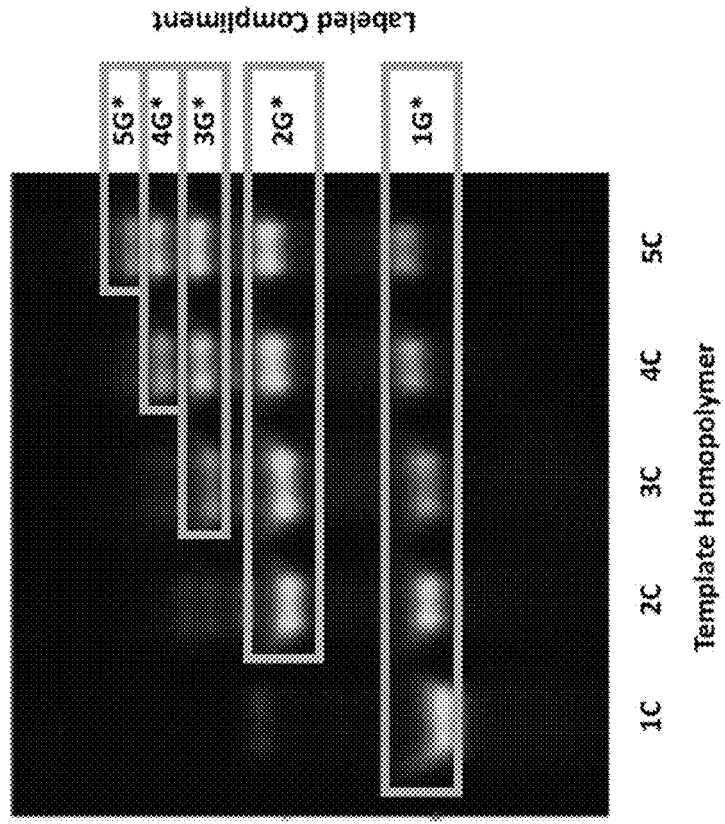
Figure 20C:
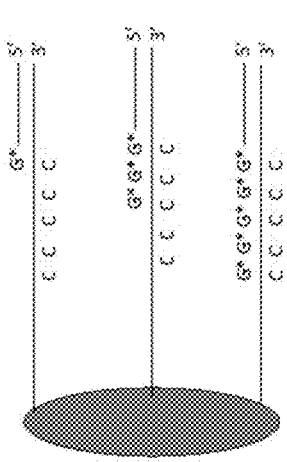
FIG. 20C shows signals detected from sequencing a template having a homopolymeric region using labeled nucleotides.

A nucleic acid template is provided that has various lengths of a homopolymer region comprising cytosines (1C, 2C, 3C, 4C, 5C). The template is contacted with guanosine-containing nucleotides labeled with Atto532 fluorophore (e.g., as described herein; denoted herein as G*). The labeled nucleotides may be provided in a solution as a nucleotide flow (e.g., as described herein). The nucleotide flow may include 100% labeled nucleotides (e.g., the nucleotide flow may include only labeled nucleotides and no unlabeled nucleotides) or may include both labeled and unlabeled nucleotides (e.g., as described herein). The labeled and, where present, unlabeled nucleotides may not be terminated so that multiple nucleotides can be incorporated into as many positions in succession as there appear cytosines in the template. An enzyme (e.g., a polymerase enzyme, such as Bst 3.0) may be used to incorporate labeled and/or unlabeled nucleotides into an extended primer using the nucleic acid having a polycytosine sequence as a template. A plurality of copies of the template may be immobilized to a bead or other support (e.g., as described herein). This procedure is schematically illustrated in FIGS. 20A and 20B.

In some cases, the labeled nucleotide incorporates into as many positions in succession as there appear cytosine in the template. In other cases, less than all potential G* are incorporated. Where unlabeled nucleotides are included in the nucleotide flow, both unlabeled and labeled nucleotides may be incorporated. For example, for a template including a homopolymeric region including three cytosines, the incorporated nucleotides may have the sequence GGG, GG*G, GGG*, G*GG, G*G*G, G*GG*, GG*G*, or G*G*G*, where G* indicates a labeled nucleotide and G indicates an unlabeled nucleotide. The sequence of the incorporated nucleotides may vary based on, for example, the labeling fraction of the nucleotide flow (e.g., the ratio of labeled to unlabeled nucleotides in the flow) and the optical (e.g., fluorescent) labeling reagent used to label the nucleotides.

Labeled polynucleotide products are separated on a Bio-rad denaturing acrylamide gel and imaged using blue and green LEDs to detect incorporated labeled nucleotides. As shown in FIG. 20C, 1, 2, 3, 4, and 5 consecutive cytosines can be detected using this method.

Example 13: Sequencing by Synthesis Using a High Fraction of Labeled Nucleotides A template nucleic acid having a length of at least 30 nucleotides is sequenced using the procedures and labeled nucleotides described herein. The template to be sequenced may be immobilized to a support (e.g., as described herein). The template is subjected to a sequencing by synthesis reaction, in which the template is sequentially contacted with solutions (e.g., nucleotide flows) comprising PolD polymerase (New England Biolabs) and a plurality of nucleotides of a single canonical type (e.g., T, A, C, or G). In each nucleotide flow, approximately 20% of the nucleotide population is labeled with Atto633 as described herein above to provide a labeling fraction of about 20%. The remaining nucleotides are unlabeled. Nucleotides included in nucleotide flows are not terminated to allow efficient sequencing of homopolymeric regions of the template. After contacting the template with a first nucleotide flow including nucleotides of a first canonical type, the template is contacted with a wash flow to remove unincorporated nucleotides. A fluorescent image is collected. The linker of the fluorescent labeling reagent associated with incorporated labeled nucleotides is contacted with a cleavage flow comprising a cleavage reagent configured to cleave a cleavable group of the linker to separate the fluorescent dye (e.g., Atto633) of the fluorescent labeling reagent from the incorporated nucleotide. An additional wash flow may be used to remove the cleavage flow. In some cases, a chase flow including unlabeled nucleotides of the first canonical type may follow the initial nucleotide flow and precede or follow the imaging process. The process is repeated for the second, third, and fourth nucleotide types in succession, and then the entire cycle is repeated.

Figure 21A:
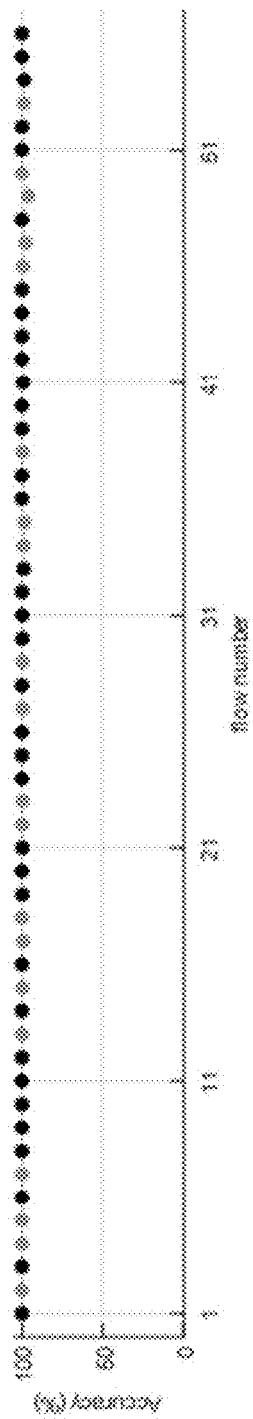
FIG. 21A shows example results of a sequencing analysis utilizing populations of nucleotides comprising 20% fluorophore labeled dNTPs.
Figure 21B:
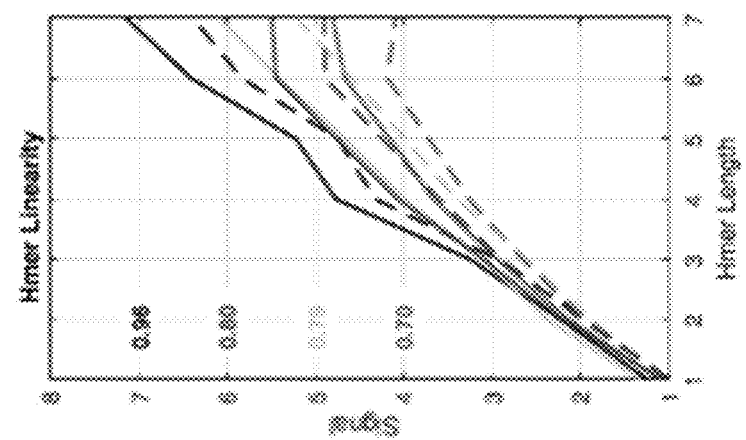
FIG. 21B shows fluorescence signal intensity as a function of homopolymer length.

FIG. 21A shows the results of application of this method to a sample template. A black circle indicates that a nucleotide was incorporated and a gray circle indicates that no nucleotide was incorporated in a particular flow cycle. As shown in the figure, the incorporation of one or more nucleotides in a flow cycle can be determined with a high degree of accuracy. Furthermore, as is shown in FIG. 21B, the relationship between signal intensity and labeled nucleotide homopolymer length may be substantially linear across a plurality of templates (e.g., as described herein). For example, the signal intensity may be proportional to the length of a homopolymeric region of the template. This proportionality indicates that quenching effects have been substantially overcome. In FIG. 21B, the slope for G is 0.96, for C is 0.80, for A is 079, and for T is 0.70. The dotted line indicates the actual signal, while the solid line indicates the signal after correction for phasing.

Example 14: Sequencing by Synthesis Using 100% Labeled Nucleotides

Figure 22:
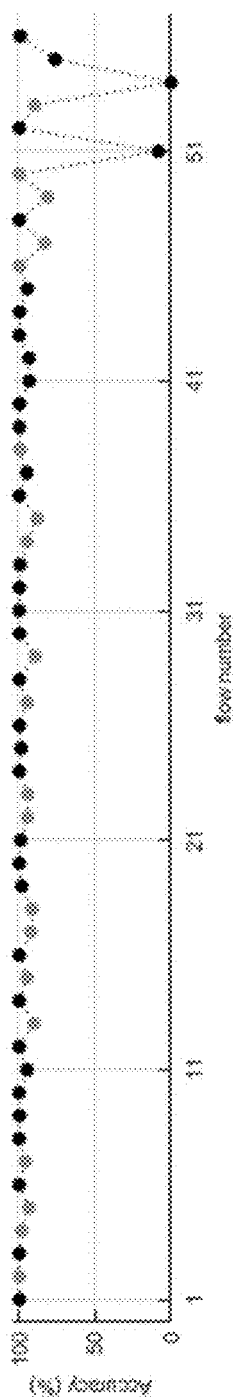
FIG. 22 shows example results of a sequencing analysis utilizing populations of nucleotides comprising 100% fluorophore labeled dNTPs.

A template nucleic acid having a length of at least 30 nucleotides is sequenced as described in Example 13, but with solutions in which 100% of the nucleotides are labeled. In FIG. 22, black circles indicate that a base was incorporated in a given flow cycle, while gray circles indicate that a base was not incorporated in a given flow cycle. As can be seen from FIG. 22, the sequencing method can be used to detect base incorporation through 50 flow cycles.

Example 15: Labeled Proteins

A protein is labeled with a plurality of optical (e.g., fluorescent) labeling reagents (e.g., as described herein). For example, the protein may be labeled with three or more optical labeling reagents. The optical labeling reagents associated with the protein may all comprise a fluorescent dye of the same type. The optical labeling reagents associated with the protein may all comprise a linker of the same type. The protein may be an antibody, such as a monoclonal antibody.

The protein is used to label a cell. The cell may be a component of sample, which sample may comprise a plurality of cells. The cells of the sample may be analyzed and sorted using flow cytometry. Flow cytometric analysis may identify the cell as being labeled with the protein associated with the plurality of optical labeling reagents. In some cases, a plurality of cells of a sample may be labeled with optical labeling reagents (e.g., as described herein). For example, cells comprising a particular cell surface feature (e.g., an antigen) configured to associate with a protein (e.g., a protein labeled with a plurality of optical labeling reagents, such as an antibody labeled with a plurality of optical labeling reagents) may be labeled with labeled proteins and analyzed and/or sorted using flow cytometry. Analyzed and/or sorted cells may be subjected to further downstream analysis and processing, including, for example, nucleic acid sequencing, staining, imaging, function assays, immunoassays, isolation/expansion, additional labeling, immunoprecipitation, etc.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A composition comprising a compound of Formula (I):

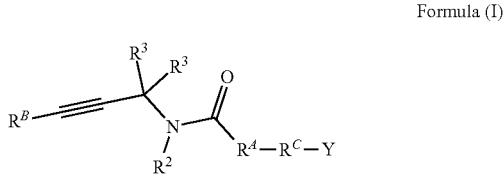

Formula (I)

or a salt or solvate thereof, wherein:
- $R^A$ is an optionally substituted 5-12 membered ring system, wherein substituents on $R^A$ are independently selected from $R^4$;
- $R^B$ comprises a nucleotide, a nucleotide analog, or a nucleoside, wherein each of the nucleotide, the nucleotide analog, and the nucleoside comprises a nucleobase, wherein the alkyne of Formula (I) is covalently linked to the nucleobase, wherein $R^B$ is optionally substituted with $R^5$;
- $R^C$ is selected from optionally substituted $C_{1-6}$ alkyl, optionally substituted $C_{2-6}$ alkenyl, and optionally substituted $C_{2-6}$ alkynyl, or $R^C$ is absent, wherein substituents on $R^C$ are independently selected from $R^6$;
- Y is —SH, —S(=O)H, —S(=O)$_2$H, or —S(=O)(OH);
- $R^2$ is selected from hydrogen, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, and optionally substituted 3-6-membered heterocycloalkyl, wherein substituents on $R^2$ are independently selected from $R^6$;
- each $R^3$ is independently selected from hydrogen, halogen, —CN, —OH, —OR$^8$, —C(=O)R$^8$, —CO$_2$R$^7$, —C(=O)N(R$^7$)$_2$, —N(R$^7$)$_2$, —NR$^7$C(=O)R$^7$, —NR$^7$C(=O)N(R$^7$)$_2$, —SR$^7$, —S(=O)R$^8$, —SO$_2$R$^8$, —SO$_2$N(R$^7$)$_2$, —NO$_2$, optionally substituted $C_1$-$C_6$ alkyl, optionally substituted $C_1$-$C_6$ alkenyl, optionally substituted $C_1$-$C_6$ alkynyl, optionally substituted monocyclic carbocycle, and optionally substituted monocyclic heterocycle, wherein optional substituents on $C_1$-$C_6$ alkyl, $C_1$-$C_6$ alkenyl, $C_1$-$C_6$ alkynyl, monocyclic carbocycle, and monocyclic heterocycle are independently selected from $R^6$;
- or two $R^3$ are taken together with the atom to which they are attached to form an optionally substituted 3- to 6-membered heterocycle or carbocycle, wherein optional substituents on the 3- to 6-membered heterocycle or carbocycle are independently selected from $R^6$;
- $R^4$ is selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —NR$^9$SO$_2$R$^9$, —SR$^9$, —S(=O)R$^{10}$, —SO$_2$R$^{10}$, —SO$_2$N(R$^9$)$_2$, —NO$_2$, optionally substituted $C_1$-$C_6$ alkyl, optionally substituted $C_2$-$C_6$ alkenyl, optionally substituted $C_2$-$C_6$ alkynyl, an optionally substituted $C_3$-$C_{10}$ carbocycle, and an optionally substituted 3-10-membered heterocycle, wherein substituents on $R^4$ are independently selected from $R^6$;
- $R^5$ is selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —NR$^9$SO$_2$R$^9$, —SR$^9$, —S(=O)R$^{10}$, —SO$_2$R$^{10}$, —SO$_2$N(R$^9$)$_2$, —NO$_2$, optionally substituted $C_1$-$C_6$ alkyl, optionally substituted $C_2$-$C_6$ alkenyl, optionally substituted $C_2$-$C_6$ alkynyl, an optionally substituted $C_3$-$C_{10}$ carbocycle, and an optionally substituted 3-10-membered heterocycle, wherein substituents on $R^5$ are independently selected from $R^6$;
- each $R^6$ is independently selected from halogen, =O, =S, —CN, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, —SR$^9$, —S(=O)R$^{10}$, —SO$_2$R$^{10}$, —SO$_2$N(R$^9$)$_2$, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, optionally substituted monophosphate, optionally substituted diphosphate, optionally substituted triphosphate, and 3- to 6-membered heterocycle;
- each $R^7$ is independently selected from hydrogen, optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;
- or two $R^7$ are taken together with the atom(s) to which they are attached to form an optionally substituted 3- to 6-membered heterocycle, wherein optional substituents on the 3- to 6-membered heterocycle are independently selected from $R^6$;
- each $R^8$ is independently selected from optionally substituted $C_1$-$C_6$ alkyl, optionally substituted $C_3$-$C_6$ carbocycle, and optionally substituted 3-6-membered heterocycle, wherein optional substituents on the $C_1$-$C_6$ alkyl, $C_3$-$C_6$ carbocycle, and 3-6-membered heterocycle are independently selected from $R^6$;
- each $R^9$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle;
- or two $R^9$ on the same nitrogen atom are taken together with the nitrogen to which they are attached to form a 3- to 6-membered heterocycle;
- each $R^{10}$ is independently selected from $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle.

2. The composition of claim 1, wherein the heteroatoms of $R^B$ are each N.

3. The composition of claim 2, wherein $R^B$ is an optionally substituted pyrimidine, an optionally substituted 7H-pyrrolo[2,3-d]pyrimidine, or an optionally substituted purine.

4. The composition of claim 3, wherein $R^B$ is substituted with at least one $R^5$ selected from an optionally substituted $C_3$-$C_{10}$ carbocycle and an optionally substituted 3-10-membered heterocycle.

5. The composition of claim 3, wherein $R^B$ comprises a blocked or terminated nucleotide or nucleotide analogue.

6. The composition of claim 1, wherein $R^A$ is an optionally substituted 5-12 membered carbocyclic ring system.

7. The composition of claim 1, wherein $R^A$ is an optionally substituted 5-12 membered heterocyclic ring system.

8. The composition of claim 1, wherein the carbonyl in Formula (I) is connected to a carbon of $R^A$.

9. The composition of claim 1, wherein $R^A$ is an optionally substituted 5-12 membered bicyclic ring system.

10. The composition of claim 1, wherein $R^A$ is substituted with at least 1 $R^4$ moiety.

11. The composition of claim 1, wherein two $R^3$ are taken together with the atom to which they are attached to form an optionally substituted 3- to 6-membered heterocycle or carbocycle, wherein optional substituents on the 3- to 6-membered heterocycle or carbocycle are independently selected from $R^6$.

12. The composition of claim 1, wherein each $R^4$ is independently selected from halogen, —OH, —OR$^{10}$, —N(R$^9$)$_2$, —C(=O)R$^9$, —C(=O)OR$^9$, —OC(=O)R$^9$, —C(=O)N(R$^9$)$_2$, —NR$^9$C(=O)R$^9$, —NR$^9$C(=O)N(R$^9$)$_2$, —OC(=O)N(R$^9$)$_2$, —NR$^9$C(=O)OR$^9$, —OC(=O)OR$^9$, and optionally substituted $C_1$-$C_6$ alkyl.

13. The composition of claim 1, wherein Y is —SH.

14. The composition of claim 1, wherein $R^C$ is absent.

15. The composition of claim 1, wherein Y is —S(=O)H.

16. The composition of claim 1, wherein Y is —S(=O)(OH).

17. The composition of claim 1, wherein Y is —S(=O)$_2$H.

18. The composition of claim 1, wherein $R^A$ is a non-aromatic optionally substituted 5-12 membered ring system.

19. The composition of claim 1, wherein the carbonyl and Y in Formula (I) are not on adjacent atoms of $R^A$ when $R^C$ is absent.

20. The composition of claim 1, wherein the composition comprises an aqueous solution.

\* \* \* \* \*